US009163277B2

(12) United States Patent
Yamana et al.

(10) Patent No.: US 9,163,277 B2
(45) Date of Patent: *Oct. 20, 2015

(54) MICROFLUIDIC DEVICE

(71) Applicant: Formulatrix, Inc., Waltham, MA (US)

(72) Inventors: Kabir James Yamana, Cambridge, MA (US); Sean Yamana-Hayes, Cambridge, MA (US)

(73) Assignee: Formulatrix, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/803,208

(22) Filed: Mar. 14, 2013

(65) Prior Publication Data
US 2014/0272981 A1    Sep. 18, 2014

(51) Int. Cl.
*G01N 21/75* (2006.01)
*C12Q 1/68* (2006.01)

(52) U.S. Cl.
CPC ............. *C12Q 1/6806* (2013.01); *G01N 21/75* (2013.01)

(58) Field of Classification Search
CPC ....................................... G01N 21/75
USPC ........................................ 422/417
See application file for complete search history.

(56) References Cited

U.S. PATENT DOCUMENTS

| | | | |
|---|---|---|---|
| 4,632,244 A * | 12/1986 | Landau ..................... | 206/219 |
| 5,229,297 A * | 7/1993 | Schnipelsky et al. ........... | 436/94 |
| 5,508,197 A | 4/1996 | Hansen et al. | |
| 6,251,343 B1 | 6/2001 | Dubrow et al. | |
| 6,268,131 B1 | 7/2001 | Kang et al. | |
| 6,408,878 B2 | 6/2002 | Unger et al. | |
| 6,503,757 B1 | 1/2003 | Chow | |
| 6,645,432 B1 | 11/2003 | Anderson et al. | |
| 6,719,868 B1 | 4/2004 | Schueller et al. | |
| 6,793,753 B2 | 9/2004 | Unger et al. | |
| 6,929,030 B2 | 8/2005 | Unger et al. | |
| 7,195,670 B2 | 3/2007 | Hansen et al. | |
| 7,216,671 B2 | 5/2007 | Unger et al. | |
| 7,307,802 B2 | 12/2007 | Unger et al. | |
| 7,318,912 B2 | 1/2008 | Pezzuto et al. | |
| 7,323,143 B2 | 1/2008 | Anderson et al. | |
| 7,476,363 B2 | 1/2009 | Unger et al. | |
| 7,479,186 B2 | 1/2009 | Quake et al. | |
| 7,494,555 B2 | 2/2009 | Unger et al. | |
| 7,588,672 B2 | 9/2009 | Unger et al. | |
| 7,601,270 B1 | 10/2009 | Unger et al. | |
| 7,604,965 B2 | 10/2009 | McBride et al. | |
| 7,666,361 B2 | 2/2010 | McBride et al. | |
| 7,691,333 B2 | 4/2010 | McBride et al. | |
| 7,704,735 B2 | 4/2010 | Facer et al. | |
| 7,749,737 B2 | 7/2010 | McBride et al. | |
| 7,766,055 B2 | 8/2010 | Unger et al. | |
| 7,815,868 B1 | 10/2010 | Jones et al. | |
| 7,837,946 B2 | 11/2010 | McBride et al. | |
| 7,867,454 B2 | 1/2011 | Goodsaid et al. | |
| 7,867,763 B2 | 1/2011 | Facer et al. | |
| 7,906,072 B2 | 3/2011 | Unger et al. | |
| 8,048,378 B2 | 11/2011 | Unger et al. | |

FOREIGN PATENT DOCUMENTS

| | | |
|---|---|---|
| EP | 0 488 769 A2 | 6/1992 |
| EP | 1 065 378 A3 | 5/2001 |
| EP | 1 195 523 A2 | 4/2002 |
| WO | WO 01/01025 A2 | 1/2001 |
| WO | WO 02/43615 A2 | 6/2002 |

\* cited by examiner

*Primary Examiner* — Ardin Marschel
(74) *Attorney, Agent, or Firm* — Wolf, Greenfield & Sacks, P.C.

(57) ABSTRACT

Microfluidic devices of the present disclosure relate to quick and inexpensive microfluidic manipulation/handling. A number of channels may be provided for supply of fluid ingredients to a number of cavities. A separating material may provide fluid separation between a number of cavities, such as corresponding cavities of a reaction chamber. Once the cavities are supplied with fluid ingredient, channels connecting the cavities may be sealed off; that is, the cavities may be subject to fluid isolation. In some embodiments, a sealing material may be compressed so as to deform into the channels obstructing fluid flow. The separating material may be manipulated so that the initial fluid separation between cavities is removed. Removal of this fluid separation subsequently permits mixing of fluid ingredient(s) contained within previously separated cavities. In some embodiments, the fluid separation may be removed by heating or dissolving portions of the separating material. When appropriate, contents within reaction chambers may be subject to further processing (e.g., thermal cycling, various analyzes).

23 Claims, 43 Drawing Sheets

MICROFLUIDIC DEVICE

FIELD

Aspects of the present disclosure relate generally to methods and apparatuses for microfluidic handling.

DISCUSSION OF RELATED ART

Modern laboratory experiments often require multiple sets of reagents to be combined according to every possible permutation. An example of such an experiment is polymerase chain reaction (PCR). PCR typically utilizes a DNA sample, a DNA primer that complements the DNA sample at specific gene locations, and a "master mix" solution that contains DNA polymerase and various reagents (e.g., nucleotides) that facilitate the activities of the polymerase.

PCR also typically involves thermal cycling. When exposed to a relatively high temperature (e.g., greater than 90 C), double helix molecules of a DNA sample are separated into single strands. At a relatively lower temperature (e.g., 50-70 C), DNA primers attach at target sites to single strands of the DNA sample. At an intermediate range of temperature (e.g., 70-80 C), the polymerase facilitates elongation of DNA fragments formed from the initial attachment of primers to the single-stranded DNA molecules. The double-stranded DNA products of one PCR cycle can then be split at the relatively high temperature range and bound to new primer strands, doubling the amount of DNA in every cycle until the reagents are exhausted. Thus, the concentration of a DNA sample containing a target DNA sequence, when subject to PCR, may increase exponentially.

PCR is often used for combinatorial analysis of multiple DNA sample solutions and multiple primers. For example, ten different samples being tested for the presence of five different genes will require fifty different reactions. Because primers are often specially fabricated for each target gene, the use of such primers can be expensive. Further, existing microfluidic systems that combine multiple groups of reagents together are typically complicated in design and manufacturing. As a result, combining such reagents to test each permutation is conventionally done via hand pipetting or with a robotic system, and can be both costly and time consuming.

Digital PCR is a type of PCR analysis that involves dividing a DNA sample into a large number of separate aliquots, and amplifying the aliquots to determine whether a molecule of target DNA was present within the aliquot. Based on the number of aliquots that have undergone exponential growth, the original concentration of DNA prior to dilution may be determined. Conventional systems that employ digital PCR are generally expensive and complex.

Thus, there is a need for simpler, less expensive microfluidic systems that retain the robustness of more expensive systems while minimizing the cost per reaction.

SUMMARY

The inventors have appreciated that a microfluidic device that provides the ability to facilitate multiple combinations of small volume reagents, in a controlled yet inexpensive manner, would be advantageous, particularly in scientific settings (e.g., PCR detection, combinatorial PCR). The inventors have further appreciated that it would be beneficial to develop a quick and cost effective system for dividing a fluid ingredient evenly into a large array of separate chambers and subjecting each of the chambers to fluid isolation from one another (e.g., for digital PCR).

The present disclosure relates to microfluidic devices and their methods of use and construction. Such devices may be used to accommodate multiple series of combinatorial and/or high-throughput chemical/biological reactions more easily than existing techniques/methods.

In an embodiment, a microfluidic device is provided. The device includes a first layer defining a first cavity; a first channel arranged to provide fluid entry to the first cavity; a second layer defining a second cavity; a second channel arranged to provide fluid entry to the second cavity; and at least one separating material providing fluid separation between the first cavity and the second cavity, wherein compression of the first and second layers relative to one another causes sealing of the first channel and the second channel resulting in obstruction of the first cavity and the second cavity from further fluid entry, and wherein manipulation of the at least one separating material causes removal of the fluid separation allowing for fluid communication between the first cavity and second cavity.

In another embodiment, a method of microfluidic handling is provided. The method includes filling a first cavity defined by a first layer with fluid through a channel; filling a second cavity defined by a second layer with fluid through a channel; providing a fluid separation between the first cavity and the second cavity; compressing the first and second layers relative to one another to cause sealing of the channels resulting in obstruction of the first cavity and the second cavity from further fluid entry; and removing the fluid separation and allowing for fluid communication between the first cavity and second cavity.

In yet another embodiment, a microfluidic device is provided. The device includes a first layer defining a first cavity; a first channel arranged to provide fluid entry to the first cavity; a second layer defining a second cavity; a second channel arranged to provide fluid entry to the second cavity; and at least one separating material providing fluid separation between the first cavity and the second cavity, wherein the first and second channels are adapted to be sealed resulting in obstruction of the first cavity and the second cavity from further fluid entry, and wherein heating or dissolving of the at least one separating material causes removal of the fluid separation allowing for fluid communication between the first cavity and second cavity.

In another embodiment, a method of microfluidic handling is provided. The method includes filling a first cavity defined by a first layer with fluid through a channel; filling a second cavity defined by a second layer with fluid through a channel; providing at least one separating material as a fluid separation between the first cavity and the second cavity; sealing the channels of the first and second layers resulting in obstruction of the first cavity and the second cavity from further fluid entry; and heating or dissolving the at least one separating material to remove the fluid separation and allowing for fluid communication between the first cavity and second cavity.

In yet another embodiment, a microfluidic device is provided. The device includes a first layer defining a plurality of cavities; a plurality of channels arranged to provide fluid entry to the plurality of cavities; a second layer disposed adjacent to the first layer; and wherein compression of the first and second layers relative to one another causes sealing of the plurality of channels resulting in obstruction of the plurality of cavities from further fluid entry.

In another embodiment, a microfluidic device is provided. The microfluidic device includes a first layer defining at least one channel; a second layer having a plurality of protrusions disposed adjacent to the at least one channel; and a sealing material disposed adjacent to the at least one channel, wherein the plurality of protrusions are adapted to force at least a portion of the sealing material into the at least one channel upon application of pressure toward the at least one channel, causing partitioning of the at least one channel into a plurality of separate cavities.

In another embodiment, a method of microfluidic handling is provided. The method includes supplying a fluid to at least one channel defined by a first layer, the at least one channel disposed adjacent to a sealing material and a second layer having a plurality of protrusions; pressing the plurality of protrusions toward the at least one channel; and forcing at least a portion of the sealing material into the at least one channel to partition the at least one channel into a plurality of separate cavities containing the fluid.

Advantages, novel features, and objects of the invention will become apparent from the following detailed description of the invention when considered in conjunction with the accompanying drawings, which are schematic and which are not intended to be drawn to scale. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

The accompanying drawings are not intended to be drawn to scale. In the drawings, each identical or nearly identical component that is illustrated in various figures is represented by a like numeral. Various embodiments of the invention will now be described, by way of example, with reference to the accompanying drawings.

DETAILED DESCRIPTION

Figure 1:
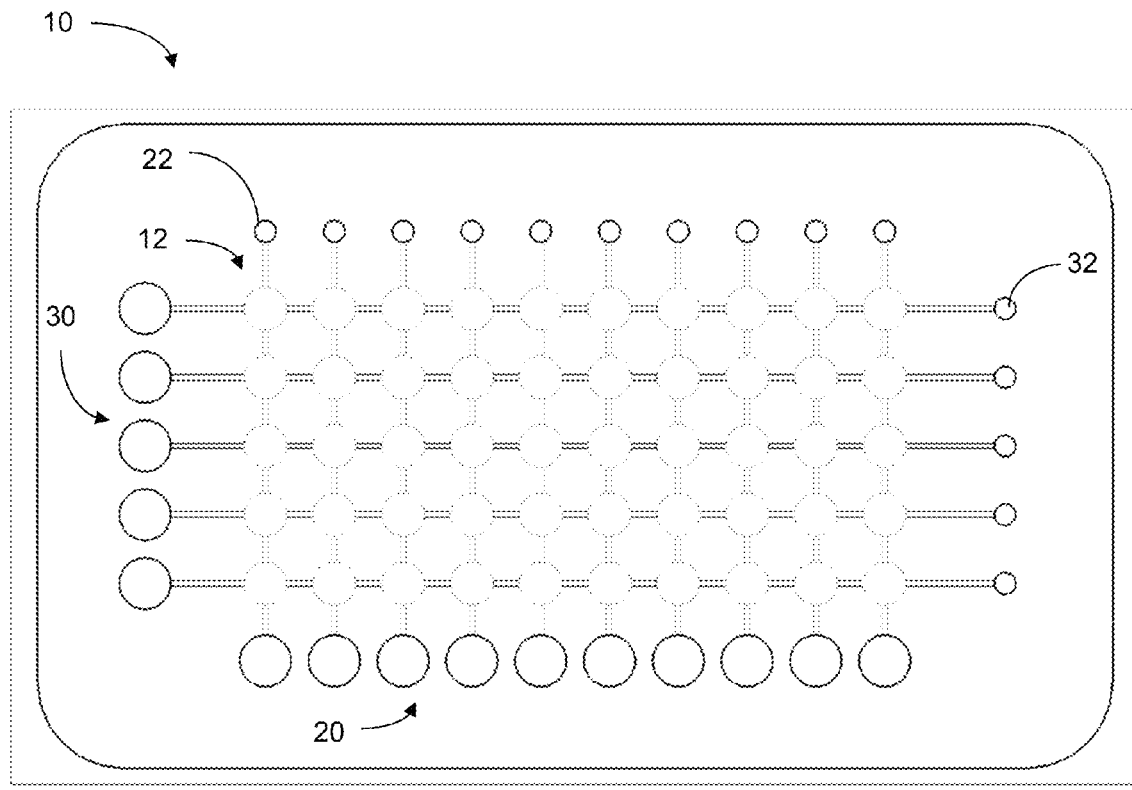
FIG. 1 shows a top view of a microfluidic device in accordance with some embodiments.

The present disclosure relates to microfluidic devices that provide for multiple combinations to be made of a number of groups of fluid ingredients, inexpensively and efficiently. For instance, in a laboratory setting, a user faced with multiple groups of reagents that are to be combined in every possible permutation for combinatorial analysis (e.g., PCR detection) may easily implement embodiments of microfluidic devices discussed herein to achieve this goal.

The present disclosure also relates to microfluidic devices that allow for a fluid ingredient to be divided evenly into separate volumes (e.g., through partitioned cavities). Those separate volumes may be fluidly isolated from one another in a quick and easy manner.

In some embodiments, when in use, a microfluidic device may perform a combinatorial analysis between different groups of fluid reagents (e.g., a group of DNA samples and a group of DNA primers). Such a combinatorial analysis may be performed via an array of chambers where each chamber includes at least two cavities that are, initially, fluidly separated. For instance, a plurality of first cavities of one layer may be separated by a separating material from a plurality of second cavities of another layer. The plurality of first cavities may be appropriately filled with fluid from a first group of fluid source reservoirs (e.g., DNA samples). The plurality of second cavities may also be appropriately filled with fluid from a second group of fluid source reservoirs (e.g., DNA primers).

Accordingly, the device may facilitate every combination between the different groups of fluid reagents (e.g., DNA samples and DNA primers). Once respective cavities are suitably filled, each cavity of each chamber is fluidly isolated from one another. Subsequently, the fluid separation between corresponding cavities of each chamber is removed, allowing fluids located within corresponding cavities to mix. Upon mixing, various conditions leading to appropriate reactions (e.g., PCR, biological reactions, chemical reactions, etc.) may be implemented.

Microfluidic devices of the present disclosure may include a number of layers where each layer defines a number of cavities. A number of channels may be arranged to provide fluid entry to the cavities. In some embodiments, certain layers may define both the cavities and the channels. In some embodiments, separate layers may define separate cavities and channels. Further, in some cases, a separating material may provide fluid separation between a number of the cavities, such as cavities that correspond to a reaction chamber.

When the cavities are adequately supplied with appropriate fluid ingredient(s), the channels that initially provide fluid connection between the cavities may be sealed so as to prevent further fluid entry into the cavities. In some embodiments, the layers of the device may be compressed relative to one another (e.g., due to external clamping, probing or rolling of the device) so as to cause the channels to seal. For example, such compression may cause a sealing material to be deformed into the space defined by the channel.

In situations where a separating material divides corresponding cavities of a reaction chamber and it is desired for the contents within those cavities to mix, the separating material may be suitably manipulated so that the fluid separation between cavities is removed. Such removal allows for mixing of the respective fluid ingredients of the corresponding cavities. In some embodiments, portions of the separating material may be heated or dissolved so that the fluid separation between corresponding cavities of a chamber is removed.

Microfluidic devices described herein may include an array of reaction chambers. Initially, each chamber may include one or more fluid separation(s) (e.g., a separating material such as a film, a membrane, etc.) between a number of cavities. In some embodiments, a separating material is disposed between layers that define cavities and/or channels, allowing for fluid enclosure within the cavities and channels. The separating material may further divide reaction chambers of the device into corresponding cavities, preventing fluid from otherwise flowing between the corresponding cavities of each chamber. Thus, while the cavities of each chamber may be individually filled with a fluid ingredient, the fluid ingredients located within each of the corresponding cavities of the chamber are unable to be mixed as long as the fluid separation is present to divide the cavities.

Before removal of the fluid separation between corresponding cavities of the same chamber, if removal occurs at all, neighboring cavities (e.g., cavities defined by an appropriate layer of the device) may be fluidly isolated (e.g., sealed or obstructed from further fluid entry) from one another. Such fluid isolation may occur through deformation (e.g., plastic deformation) of a suitable sealing material into channels that would otherwise provide fluid connection between the cavities.

In some embodiments, the separating material itself may be the sealing material that is deformed so as to cause each of the cavities of the device to be fluidly isolated from one another. For instance, appropriate portions of the separating material, which also act as a sealing material, may deform into channels causing a seal to obstruct fluid from flowing between neighboring cavities connected by the channels. The separating material may be further deformed so as to create an opening between corresponding cavities of each reaction chamber. Once an opening is created between corresponding cavities of a chamber, the chamber is no longer under fluid separation and, as a result, the contents located within each of the corresponding cavities can be combined.

Aspects of the present disclosure provide for arrangement(s) and/or technique(s) for making the process of combining different groups of reagents into separate reaction chambers quick and efficient. Aspects presented herein also provide for even division or partitioning of a fluid ingredient into small volumes and along with fluid isolation of those small volumes. It can be appreciated that microfluidic devices described herein may include any suitable number of layers, components, separating materials, sealing materials, adhesives, etc., in any appropriate arrangement or configuration, and that particular examples of the present disclosure are not intended to be limiting.

Figure 3A:
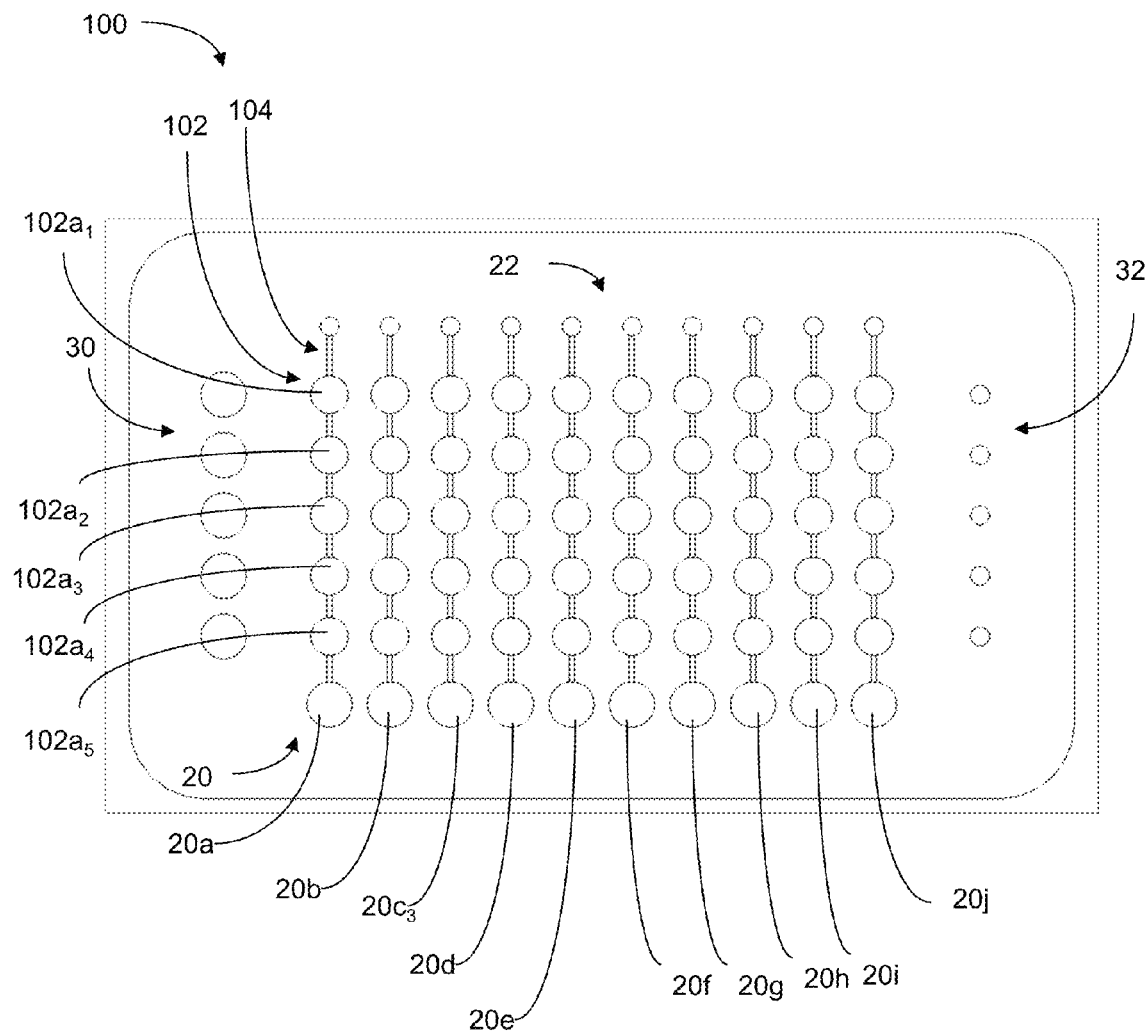
FIGS. 3A-3C depict different layers of the microfluidic device of FIG. 1.
Figure 3B:
Figure 3C:
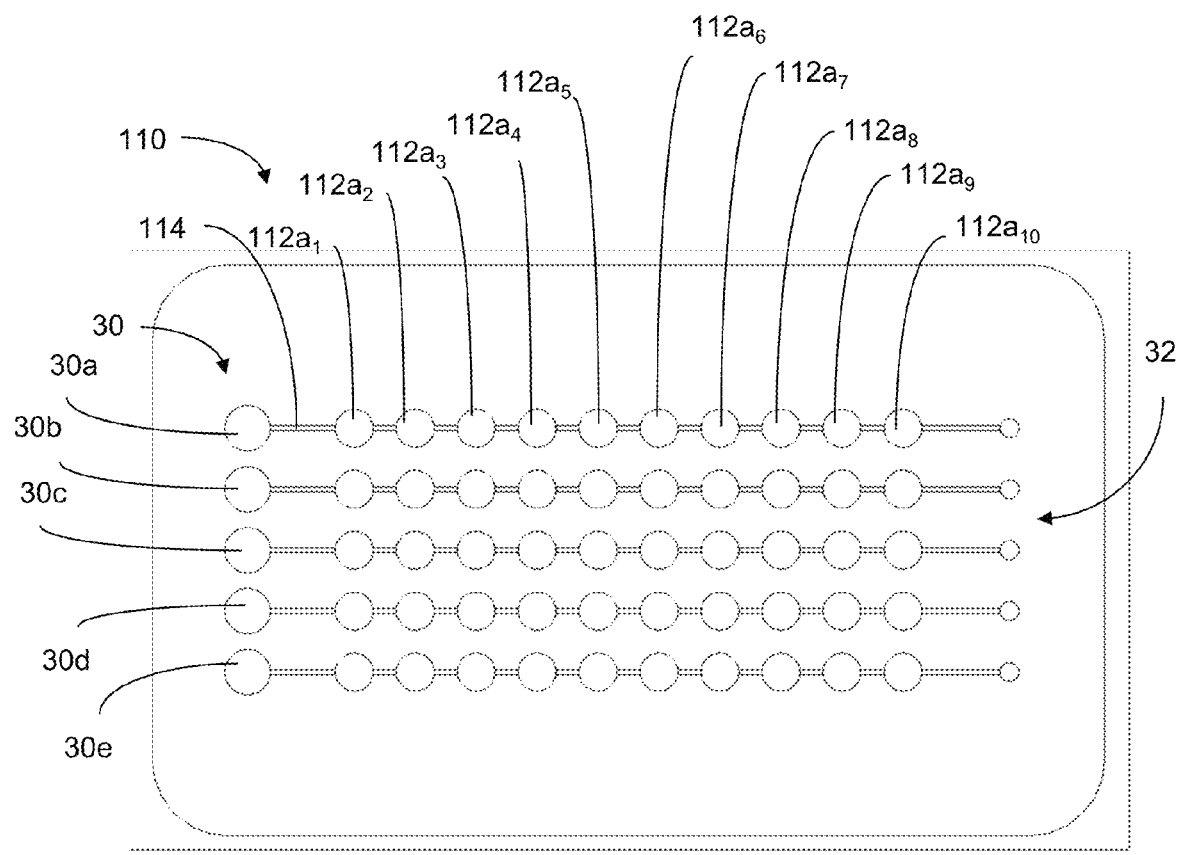

FIG. 1 depicts an embodiment of a microfluidic device 10 having an array of chambers 12 where each chamber is divided into corresponding cavities 102, 112 (separate cavities 102, 112 are further illustrated in FIGS. 3A and 3C). Inlets 20, 30 and vents 22, 32 provide for appropriate filling of fluid ingredients into respective groups of cavities, as described in more detail further below, for subsequent reaction.

Figure 2:
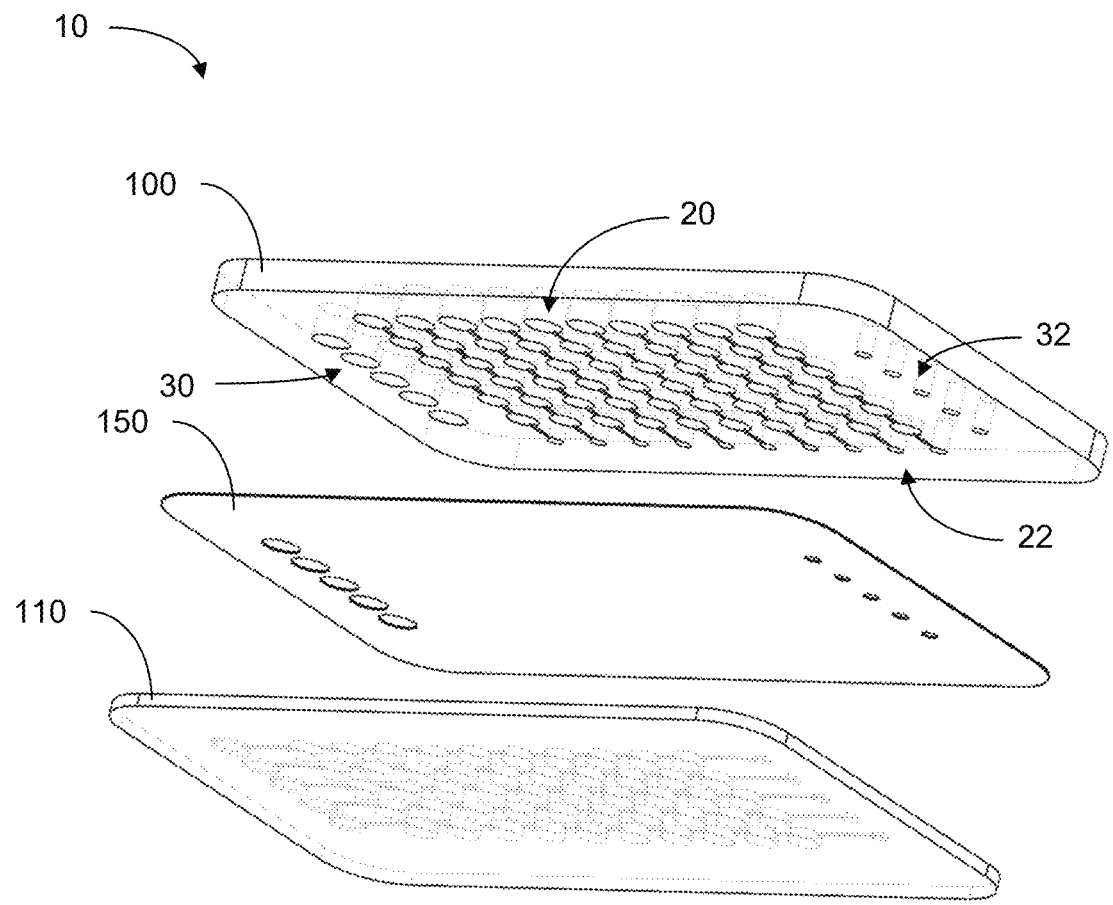
FIG. 2 illustrates an exploded perspective view of the microfluidic device of FIG. 1.

FIG. 2 depicts an exploded view of this embodiment showing the microfluidic device 10 to include a first layer 100, a second layer 110 and an intermediate layer 150 disposed in between the first and second layers. The intermediate layer 150 acts as a separating material that provides fluid separation between corresponding cavities that make up each chamber. As discussed further below, the intermediate layer 150 can also act as a sealing material for fluidly isolating each of the cavities from one another.

FIG. 3A depicts the first layer 100 which defines a number of cavities 102 that are divided into subsets of cavities. Each subset of cavities includes a respective inlet 20, for supply of a fluid ingredient to each of the cavities, and vent 22, for exhaust of excess fluid (e.g., air, ingredient(s), etc.) when appropriate. Illustrated in FIG. 3A, ten different fluid source reservoirs are provided as respective inlets for filling each of the subsets of cavities. That is, the first layer has ten inlets 20a, 20b, 20c, 20d, 20e, 20f, 20g, 20h, 20i, 20j where each inlet is in fluid connection with five cavities 102 and vents 22. Respective inlets 20, cavities 102 and vents of a subset are, in turn, connected to one another via a plurality of channels 104.

For example, a fluid ingredient may be supplied through inlet 20a to each cavity of the subset of cavities $102a_1$, $102a_2$, $102a_3$, $102a_4$, $102a_5$ via a channel 104, which allows the cavities $102a_1$, $102a_2$, $102a_3$, $102a_4$, $102a_5$ to be in fluid communication during filling. Accordingly, different fluid ingredients may be supplied to each subset of cavities corresponding to the inlets 20a, 20b, 20c, 20d, 20e, 20f, 20g, 20h, 20i, 20j. Inlets 30 and corresponding vents 32 are also provided in first layer 100 so as to reach through to the second layer 110 for providing suitable fluid lines to supply cavities within the second layer.

As provided herein, channels 104 may include any part of the passageway through which fluid may flow, for example, between an inlet 20 and a vent 22, or between two or more of the cavities 102. Thus, a single channel may be considered to include multiple cavities by virtue of the cavities being in fluid communication. For example, a channel 104 may include each of cavities $102a_1$, $102a_2$, $102a_3$, $102a_4$, $102a_5$ which are in fluid communication.

FIG. 3B shows an intermediate layer 150 that includes a separating material having holes that form part of the inlets 30 and vents 32 leading to second layer 110. That is, the holes of the intermediate layer 150 allow for fluid connection between respective fluid source reservoirs that are provided as inlets 30 originating at the first layer 100 and respective cavities 112 and channels 114 of the second layer. Accordingly, in this embodiment, fluid ingredient may be supplied through the first layer 100 to fill appropriate cavities 112 and channels 114 of the second layer 110. Further, the vents 32 may allow excess fluid from the second layer to escape through the first layer.

FIG. 3C depicts the second layer 110 which, similar to the first layer 100, defines a number of cavities 112 divided into subsets of cavities. Each subset of cavities includes a respective inlet 30 and vent 32 so that fluid ingredients may be appropriately supplied to each of the cavities. As shown in FIG. 3C, the second layer has five inlets 30a, 30b, 30c, 30d, 30e where each inlet is in fluid communication with ten cavities 112 and vents 32 which are each, in turn, connected to one another via respective channels 114.

For instance, a fluid ingredient may be supplied through inlet 30a to each cavity of a subset of cavities $112a_1$, $112a_2$, $112a_3$, $112a_4$, $112a_5$, $112a_6$, $112a_7$, $112a_8$, $112a_9$, $112a_{10}$ via channel 114. During filling, the channel 114 provides fluid connection between each of the cavities $112a_1$, $112a_2$, $112a_3$, $112a_4$, $112a_5$, $112a_6$, $112a_7$, $112a_8$, $112a_9$, $112a_{10}$. It follows that different fluid ingredients may be supplied to each subset of cavities corresponding to the inlets 30a, 30b, 30c, 30d, 30e.

Similarly to that described above with respect to channels 104, channels 114 may include any part of the passageway through which fluid may flow, for example, between an inlet 30 and a vent 32, or between two or more of the cavities 112. For instance, a channel 114 may include each of cavities $112a_1$, $112a_2$, $112a_3$, $112a_4$, $112a_5$, $112a_6$, $112a_7$, $112a_8$, $112a_9$, $112a_{10}$ which are in fluid communication.

It can be appreciated that the above embodiment is presented by way of example only and is not meant to limit the present disclosure. For example, microfluidic devices described herein may include any suitable configuration of layers and components that provide for an appropriate arrangement of cavities and/or channels that may facilitate separate reactions in the cavities, or chambers that include one or more cavities.

In some embodiments, certain regions of the intermediate layer 150 or the entire layer itself accommodate adherence or attachment of the first and second layers together. For example, the layer may include one or more materials (e.g., adhesive, adhesive on a backing, etc.) that facilitate bonding between the layers. In some embodiments, a different layer and/or material not explicitly shown in the figures is used to adhere various layers together.

In some embodiments, portions of the intermediate layer 150 may form a barrier on one side (e.g., the bottom) of the first layer 100 so as to appropriately enclose the cavities 102 and channels 104. Conversely, portions of the intermediate layer 150 may form a barrier on one side (e.g., the top) of the second layer 110 so as to provide suitable enclosure for the cavities 112 and channels 114. Accordingly, the intermediate layer 150 (e.g., separating material) may provide fluid separation of a chamber into corresponding cavities (e.g., a first cavity from the first layer and a second cavity from the second layer that are in alignment with one another).

Figure 4:
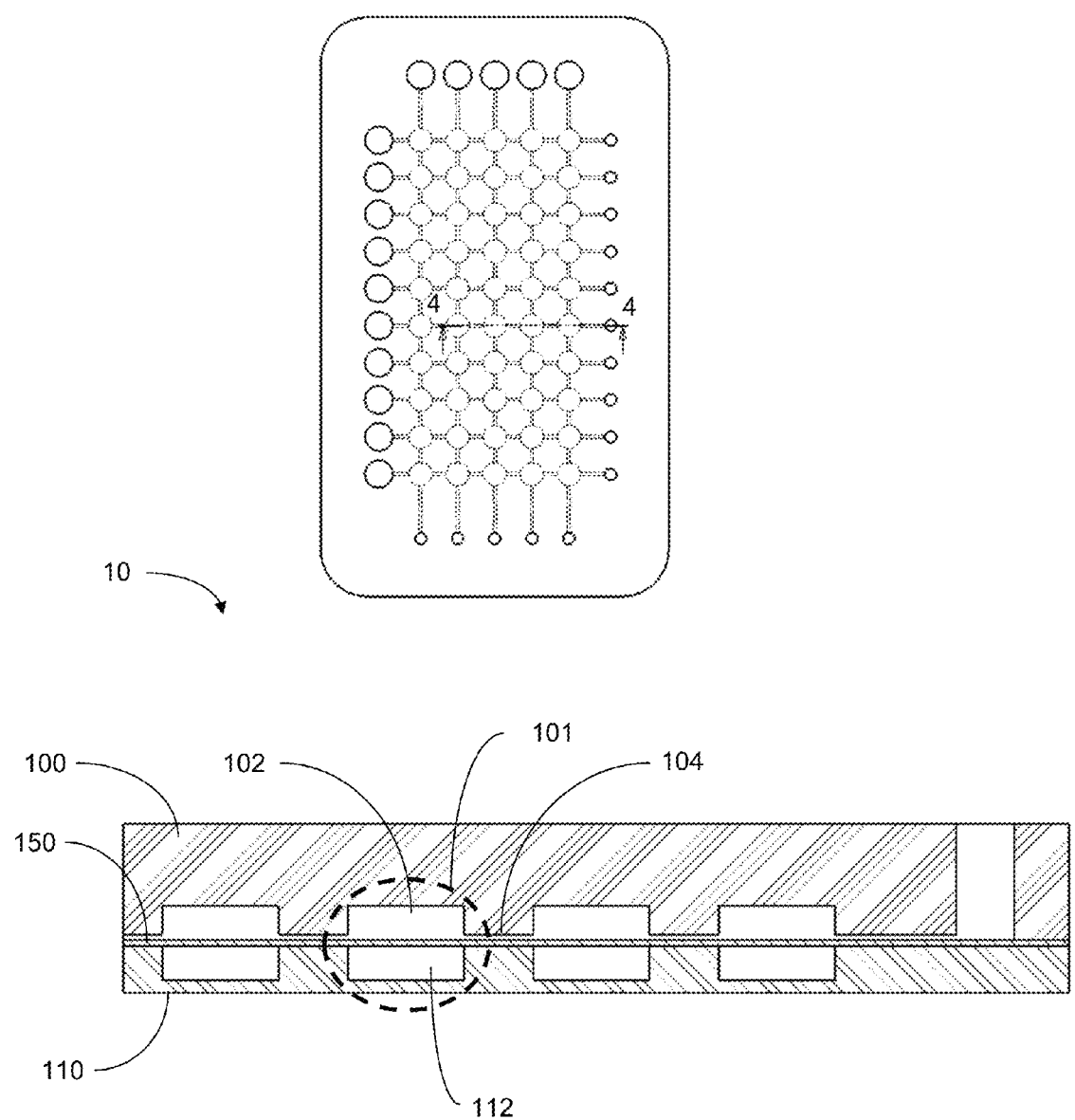
FIG. 4 shows a cross-sectional view of the microfluidic device of FIG. 1.

The cross-sectional view depicted in FIG. 4 shows an embodiment including a number of chambers with corresponding cavities of each chamber.

Channels connect cavities associated with respective layers together. As shown, a first layer 100 and a second layer 110 are respectively bonded to the intermediate layer 150 on either side. The intermediate layer 150 provides for a separating material that forms a fluid separation between corresponding cavities of each chamber. In some embodiments, the first and second layers are generally stiffer (e.g., relatively more rigid) than the intermediate layer. In other embodiments, the first and second layers are of a similar stiffness, or less stiff, than the intermediate layer. The first and second layers, as compared with one another, may be of a similar or different stiffness.

As shown in FIG. 4 and indicated by the dashed circle, the chamber 101 includes a first cavity 102 of the first layer and a second cavity 112 of the second layer, divided by the separating material of the intermediate layer. The channel 104 provides a fluid connection between other cavities 102 of the first layer. Similarly, the channel 114 (which is not expressly shown as it comes through the cross-sectional plane) provides a fluid connection between other cavities 112 of the second layer.

While the intermediate layer 150 is depicted as a single monolithic membrane that serves as a separating material between corresponding cavities of each chamber as well as forming a barrier to form a suitable enclosure for respective cavities 102, 112 and channels 104, 114, it can be appreciated that the intermediate layer may include a number of components that are separate from one another. In some embodiments, the intermediate layer may include individual separating material components that are placed at discrete positions relative to respective cavities and channels of the first and second layers. For example, the intermediate layer may include a particular separating material, or portions thereof, that are appropriately positioned so as to define the cavities, and a different separating material, or portions thereof, that define the channels. Such an arrangement may be beneficial when it is preferred that various regions of the separating material exhibit different properties (e.g., more rigid, more soft) depending on whether the material is located directly adjacent to a cavity, or a channel.

A separating material may be composed of any suitable material or composition. In some embodiments, the separating material includes a plastic/polymer, such as polyethylene, polypropylene, ethylene-vinyl acetate, an elastomer such as silicone rubber, or a wax such as paraffin or microcrystalline wax, or combinations thereof. As such, the separating material may include a blend of several different compositions or may be provided in various configurations, such as in layered or more discrete arrangements, where different pieces of the separating material are placed at various locations. As discussed further below, during use, the separating material may also be used as a sealing material for preventing fluid flow between cavities through connecting channels. Or, a different sealing material may be used in combination with a distinct separating material.

Layers of microfluidic devices described herein may include any suitable material and may be composed of similar or different materials. In some embodiments, a layer is made of a relatively rigid plastic, for example, polypropylene, polyethylene, polycarbonate, PTFE, etc. Alternatively, a layer may include a flexible, rubber-like material such as silicone or other elastomer. Other potential materials include glass, ceramics, silicon, or the like. As such, a layer may be rigid or deformable. Such materials may be translucent or clear so as to easily allow for optical measurements of the contents within the chambers/cavities.

Individual layers of the microfluidic device may be made by any suitable method. In some embodiments, layers are fabricated via injection molding, by embossing the cavities and channels into a thin sheet of plastic, etching, or any other suitable method. For example, spaces that define the cavities and channels may be formed (e.g., molded, etched) in a plastic/polymer or elastomeric material that makes up the layer.

In some embodiments, different layers may define cavities and channels that are initially in fluid communication. For example, a first layer may define a number of cavities without defining the channels that connect the cavities together; an additional layer adjacent to the first layer may define those channels that connect the cavities. Such channels may be appropriately sealed, for example, by compression of the two layers relative to each other.

As such, a layer may define one or more cavities and/or channels of the device, such as in embodiments that depict the first and second layers 100, 110. Or, as also discussed above, a layer may include a separating material and/or a sealing material, such as the intermediate layer 150.

Accordingly, in some embodiments, a layer may include acrylic adhesive, natural rubber adhesive, or silicone adhesive. Such materials may be suitable to deform into channels of the device (e.g., as a sealing material) when subject to compression. In some embodiments, adhesives may be disposed on a relatively rigid layer, or alternatively, on a separate backing Examples of suitable backings may include polypropylene, polyethylene, polycarbonate, and/or other suitable plastics.

Various components (e.g., layers, adhesives, etc.) of microfluidic devices described herein may be adhered together by any suitable method. For example, an adhesive may be used to bond one or more components together, such as for bonding a separating/sealing material and the first and/or second layers. In some embodiments, the components of the microfluidic device are compressed together (e.g., via clamping, rolling, or other externally applied force) so as to result in an evenly distributed bond between surfaces of different layers.

For certain materials, the application of an appropriate amount of compression and/or heat may result in certain characteristics of the separating/sealing material, or other components of the device, to change. For example, at elevated temperatures, certain materials such as wax will become increasingly tacky and/or adhesive, resulting in strong adherence between components of the device. Accordingly, the different layers of the device, including a wax layer, may be assembled and then subject to compression and heating for an appropriate period of time, allowing the wax to create a bond. In some embodiments, one or more appropriate solvents may be used to promote bonding between layers.

As discussed above, microfluidic devices according to the present disclosure may be useful to facilitate multiple combinations of different groups of reagents. In some embodiments, once fluid ingredients of corresponding cavities in various chambers are combined/mixed, the chamber(s) may be subject to thermal cycling. For example, a heat source configured for thermal cycling (e.g., to facilitate PCR) may be placed in contact, or otherwise coupled, with the first and/or second layer. In some cases, the layer in which the heat source is in contact may be relatively thin and/or may include a thermally conductive material so as to facilitate heat transfer.

Referring to the embodiment of FIGS. 1-4, the first layer 100 provides ten inlets 20 with five cavities 102 fluidly connected to each respective inlet 20 and the second layer 110 provides five inlets 30 with ten cavities 112 fluidly connected to each respective inlet 30. Accordingly, the device may accommodate a total of fifty different reactions based on mixtures of different combinations of reagents, depending on the supply of various fluid ingredients. Taking combinatorial PCR reactions described previously as an example, each of the inlets 20 of the first layer 100 may be supplied with ten different DNA samples to be analyzed and, hence, each of the inlets 30 of the second layer 110 may be supplied with five different DNA primer mixes as target probes for analysis of the respective DNA samples.

FIGS. 5-10F illustrate embodiments of the present disclosure where each of the cavities of the device are supplied with respective fluid ingredients prior to fluid isolation of the cavities, and after fluid isolation of the cavities, subsequent mixing of the contents within corresponding cavities.

Figure 5:
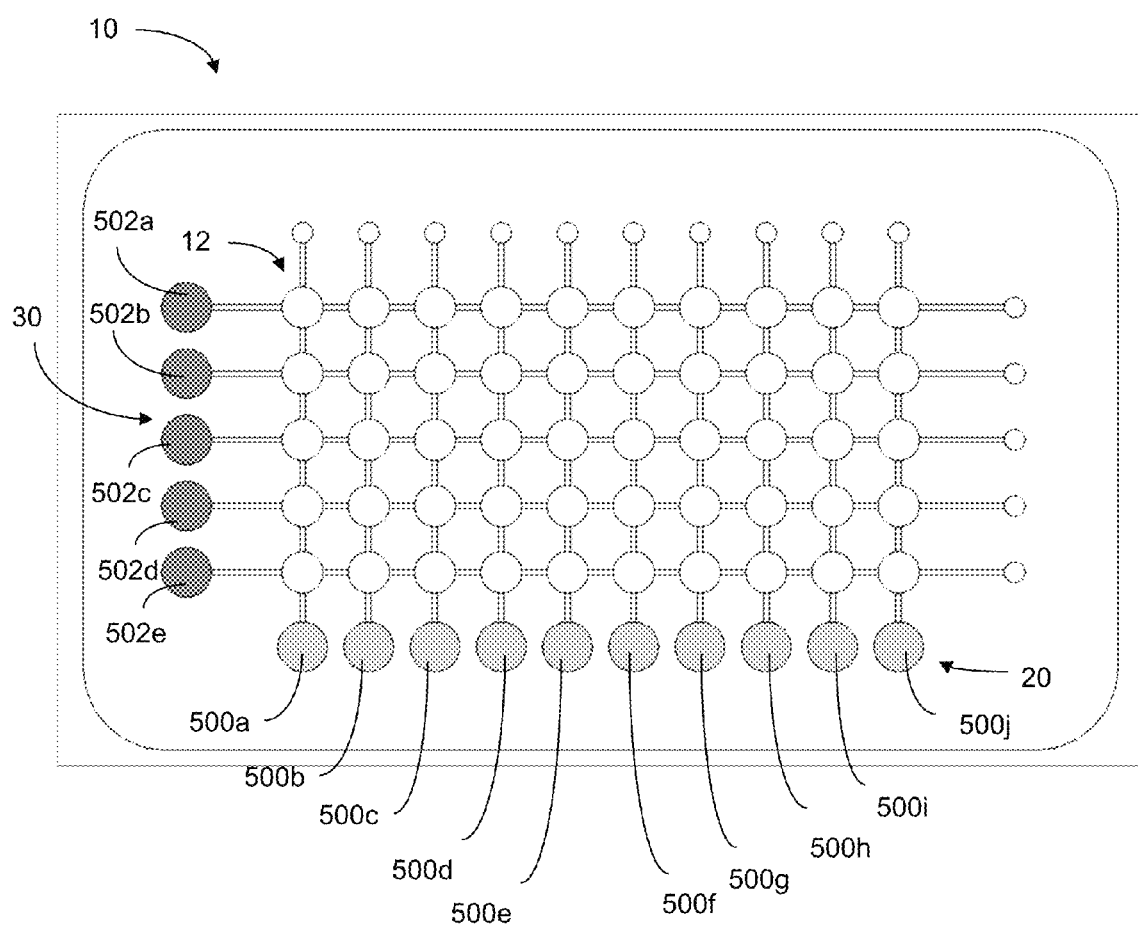
FIG. 5 depicts a top view of a microfluidic device in use in accordance with some embodiments.
Figure 6:
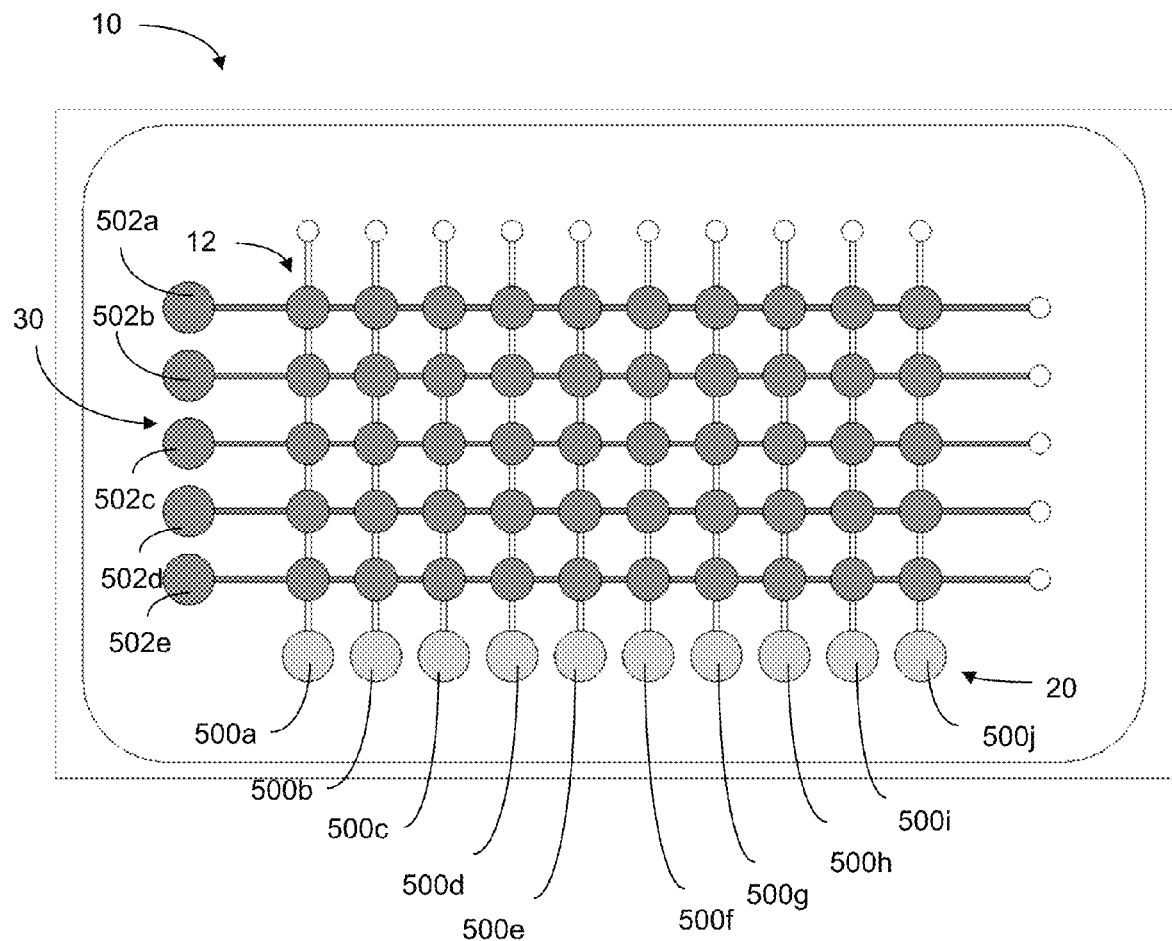
FIG. 6 shows a top view of a microfluidic device having one layer filled in accordance with some embodiments.

FIG. 5 shows an embodiment of an assembled microfluidic device where a number of fluid source reservoirs are provided as inlets 20, 30. A group of fluid source reservoirs 20 are arranged to provide filling of respective cavities of the first layer 100 with fluid ingredient 500. And another group of fluid source reservoirs 30 are arranged to fill respective cavities of the second layer 100 with fluid ingredient 502. By way of explanation, fluid ingredients 500*a*, 500*b*, 500*c*, 500*d*, 500*e*, 500*f*, 500*g*, 500*h*, 500*i*, 500*j* filling inlets 20 of the first layer 100 are illustrated to be lighter in color than fluid ingredients 502*a*, 502*b*, 502*c*, 502*d*, 502*e* filling inlets 30 of the second layer 110. FIG. 6 illustrates cavities of the second layer 110 having been filled with fluid ingredients 502*a*, 502*b*, 502*c*, 502*d*, 502*e* from respective fluid source reservoirs.

Figure 7A:
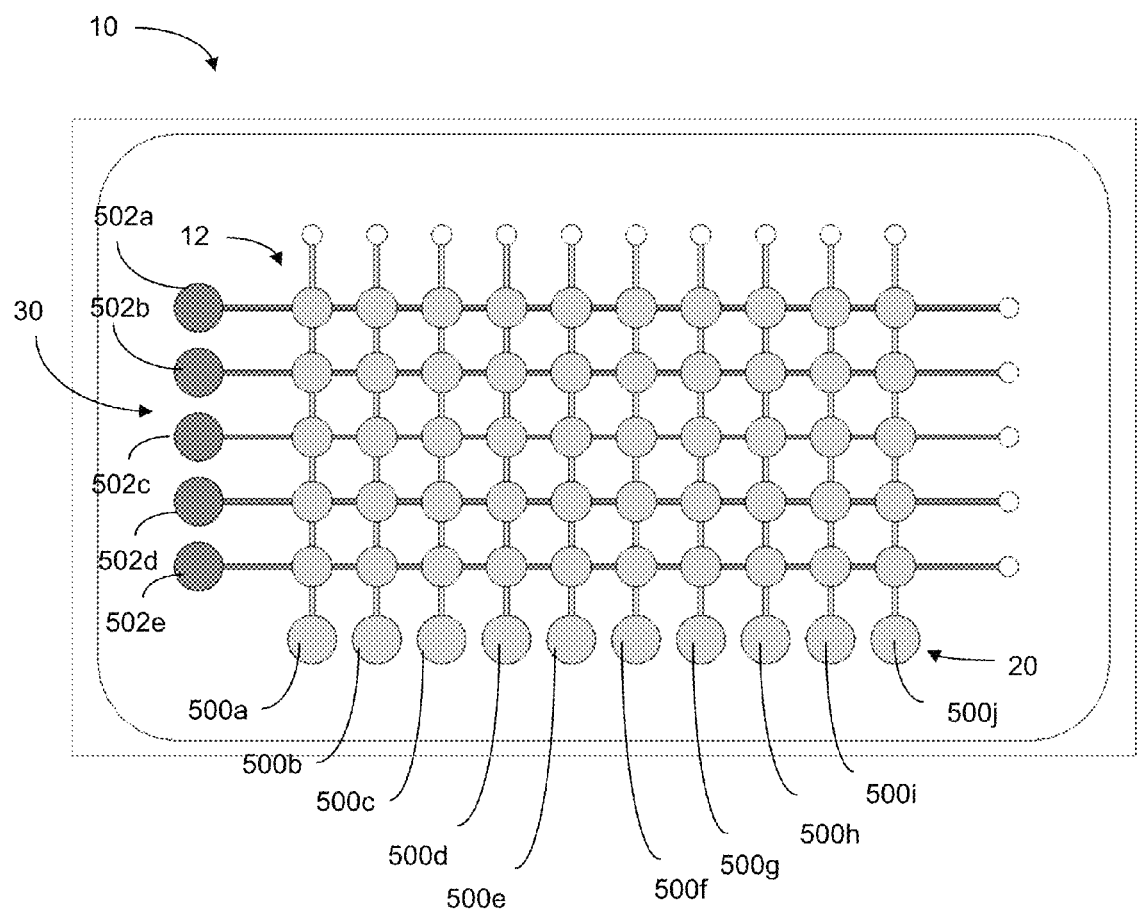
FIG. 7A shows a top view of a microfluidic device having two layers filled in accordance with some embodiments.

FIG. 7A shows cavities of the first layer 100 having been filled with fluid ingredients 500*a*, 500*b*, 500*c*, 500*d*, 500*e*, 500*f*, 500*g*, 500*h*, 500*i*, 500*j* from respective fluid source reservoirs. The fluid source reservoirs are provided as inlets 20 and arranged to fill respective cavities 102.

Fluid ingredients may be supplied to respective inlets, cavities and channels by any suitable method. In some embodiments, a machine or user pipettes appropriate reagents into input wells. Or, separate containers may be appropriately connected to respective inlets for supplying fluid held by the containers to the inlets. Cavities and channels may be supplied with respective fluid ingredients, for example, by capillary action, gravity, centrifuging, suction from the vent holes, vacuum suction, pressure on the input wells, and/or any other suitable manner. Thus, any push or pull method may be used to suitably supply cavities and channels with appropriate fluid ingredient(s). Fluid ingredients 500 and 502 may be supplied to cavities 102 and 112 sequentially or simultaneously.

Each input well 20 of the first layer 100 of this example may be suitable to accommodate filling of five cavities and the connecting channels between those cavities. In some cases, an amount of extra fluid ingredient may be left over. Similarly, each input well 30 of the second layer 110 may be suitable to accommodate filling of ten cavities and the connecting channels of those cavities. Vent holes may allow for excess air and/or fluid ingredient to escape from the channels and/or cavities when the channels and cavities are filled with respective fluid ingredients and be exhausted from the system. For instance, compression of the first and second layers relative to one another may reduce the amount of space available and/or increase the fluid pressure within the device (e.g., within cavities and channels) resulting in fluid displacement; hence, vent holes may accommodate for an appropriate amount of overflow to occur.

Figure 7B:
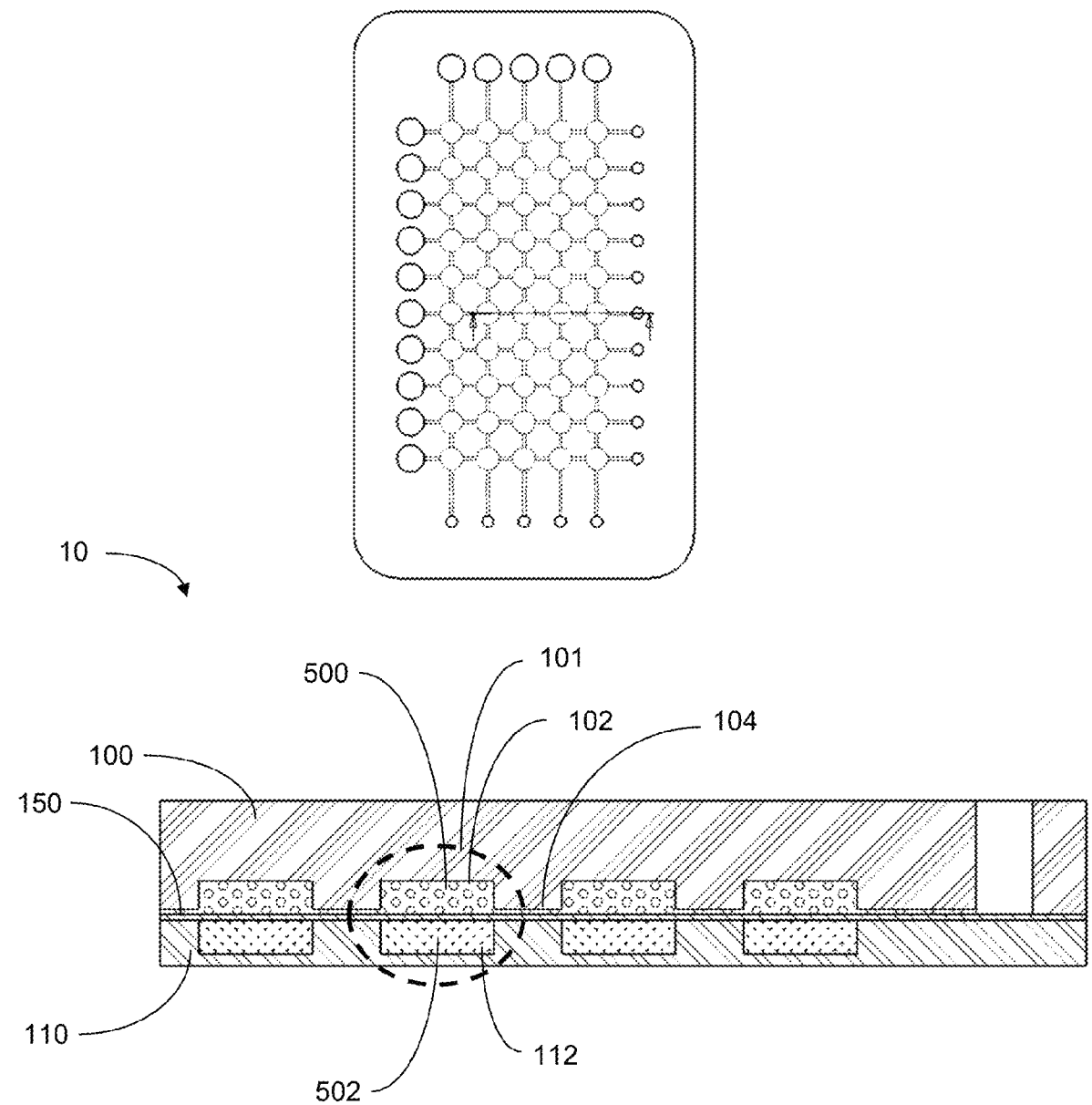
FIG. 7B illustrates a cross-sectional view of the microfluidic device of FIG. 7A.

The cross-sectional view depicted in FIG. 7B shows corresponding cavities of each chamber filled with fluid ingredients 500, 502. As indicated by the dashed circle, the chamber 101 includes first cavity 102 and second cavity 112 which are, at this stage, divided by the separating material of the intermediate layer 150 such that fluid is unable to flow between the cavities, hence, mixing of the fluid ingredients 500, 502 with each other is prevented. As further shown in FIG. 7B, the channel 104 provides a fluid connection between other cavities of the first layer having received fluid ingredient from a respective inlet 20. Similarly, the channel 114 (not expressly shown) provides a fluid connection between other cavities 112 of the second layer having received fluid ingredient from a respective inlet 30.

After the cavities are filled with the appropriate fluid ingredients, the cavities are subsequently isolated from one another such that fluid is unable to spill or flow from one cavity to another. In bringing about this fluid isolation, in some embodiments, a sealing material is caused to deform into and substantially fill the space defined by the channels so that fluid flow that was previously permitted between cavities is now blocked.

To cause such sealing of the channels between cavities, in some embodiments, an external force (e.g., compressive) and/or heat is applied to the device. For example, the device (e.g., at exterior surfaces of the layers) may be clamped, rolled or probed so as to be subject to a suitable compressive force. Further, the device may be heated so as to cause deformation of the sealing material itself, which, in some embodiments, also happens to be the separating material.

Figure 8A:
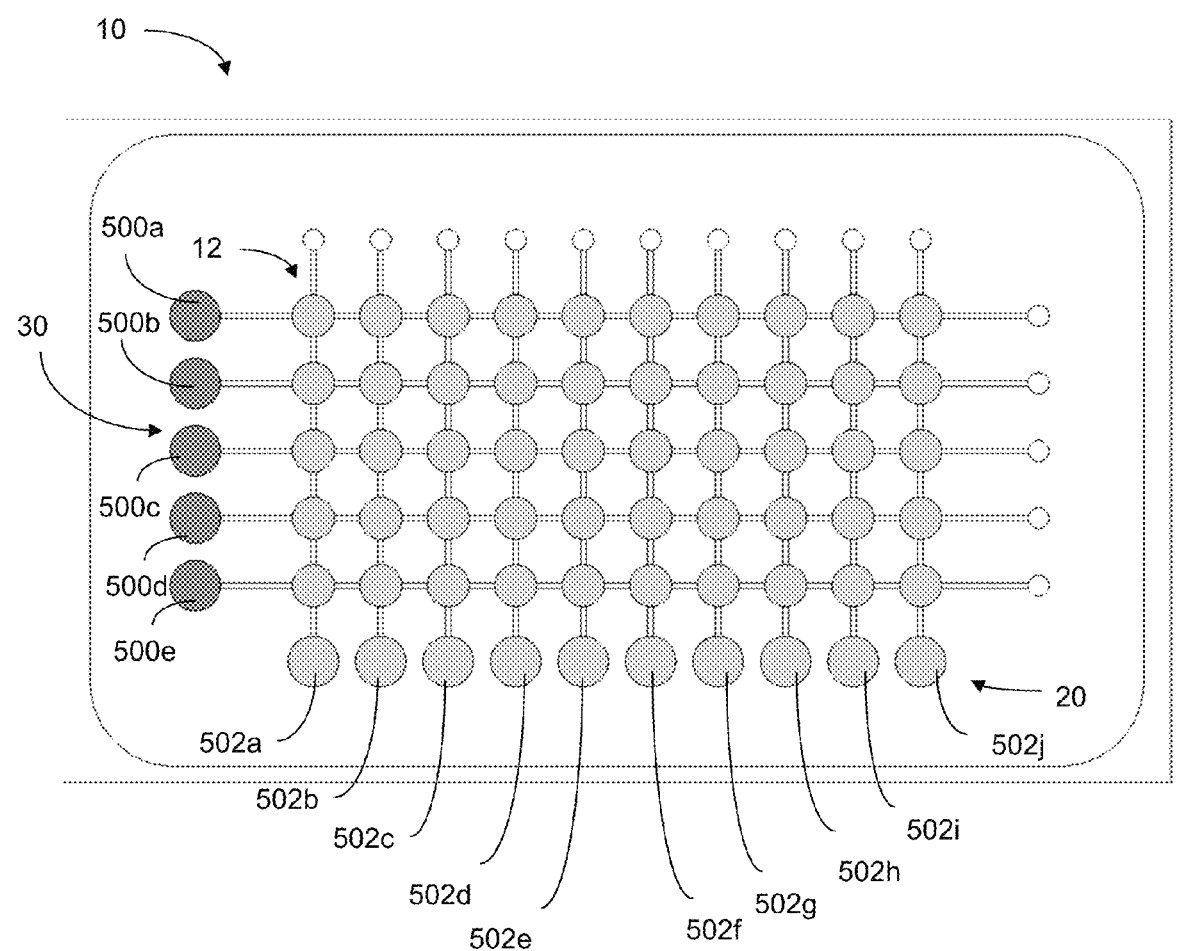
FIG. 8A depicts a top view of a microfluidic device with isolated cavities in accordance with some embodiments.
Figure 8B:
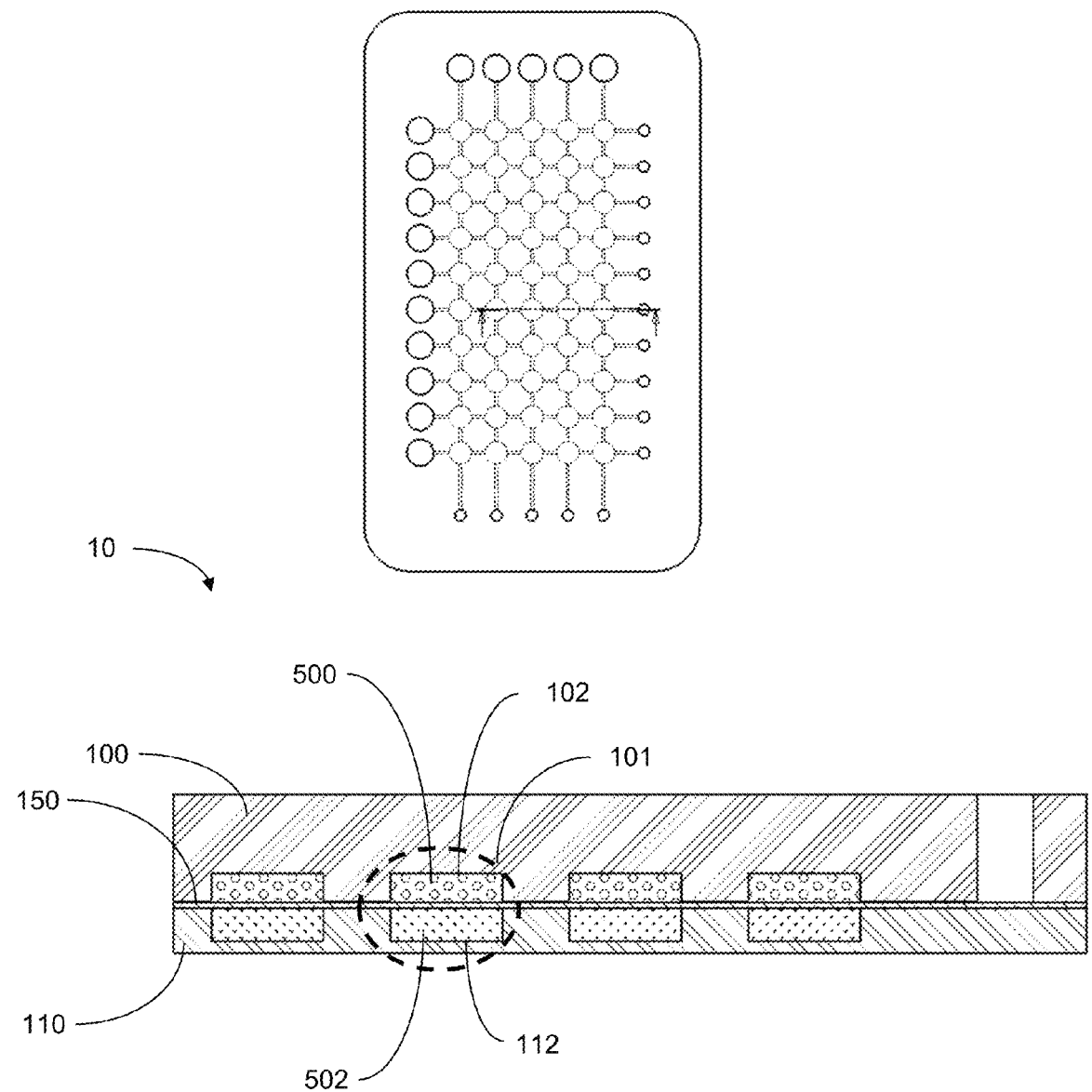
FIG. 8B illustrates a cross-sectional view of the microfluidic device of FIG. 8A.

FIGS. 8A-8B show an embodiment where application of an appropriate degree of compressive force and/or heat pushes certain portions of the separating/sealing material (e.g., regions of the separating/sealing material aligned with the channels) into the channels, resulting in sealing of the channels and, thus, fluid isolation of the cavities from one another.

In some embodiments, the amount of compressive force exerted on the device sufficient to result in sealing off of the channels may be between about 100 Newtons and about 10,000 Newtons (e.g., 100-1,000 N; 1,000-5,000 N; 5,000-10,000 N), depending on the overall size of the device and the nature of the separating/sealing material. For example, the larger the device (i.e., the more cavities and channels), the more compressive force may be required to seal the channels from flow between cavities. Or, the softer the material, the less compressive force may be needed to deform the material into respective channels of the device.

In some embodiments, the separating/sealing material may be heated to an elevated temperature so as to cause softening of the material sufficient for the material to deform into adjacent channels. Such an elevated temperature may depend on the softening point of the material, for example, between about 40 C and about 90 C (e.g., between about 50 C and about 70 C) for certain polymeric or wax compositions.

It can be appreciated that any suitable method may be used to create a seal within channels such that cavities are fluidly isolated from one another. For example, separate pieces of a sealing material may be distributed throughout the device and located directly adjacent to each channel. Upon application of heat or laser irradiation, locally (e.g., with a heat probe) and/or globally (e.g., with a heated plate) to the overall device, the sealing material may melt, soften, or otherwise deform into the channel so as to cause sealing of the channel resulting in obstruction of fluid flow between cavities. For example, the sealing material may be adapted to, at least partially, melt, soften, or otherwise deform into the channel upon application of external compressive force and/or heat to particular regions of the device, or the device as a whole.

Figure 9A:
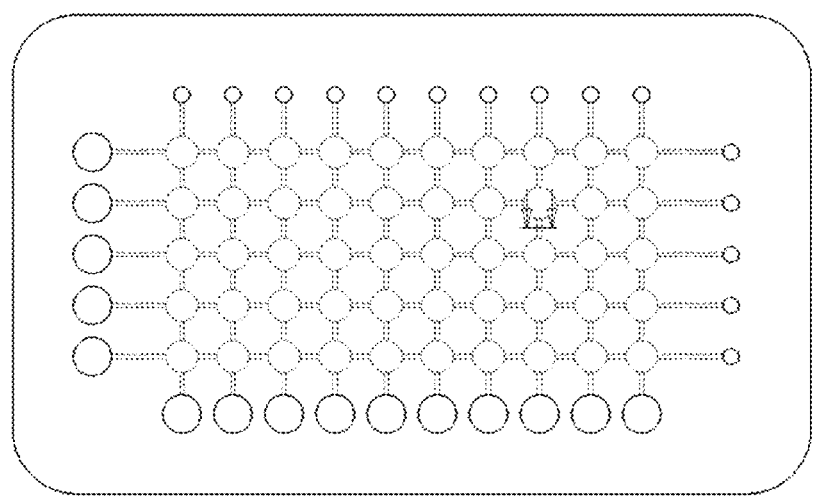
FIG. 9A shows a top view indicating a cross-section of a microfluidic device.
Figure 9B:
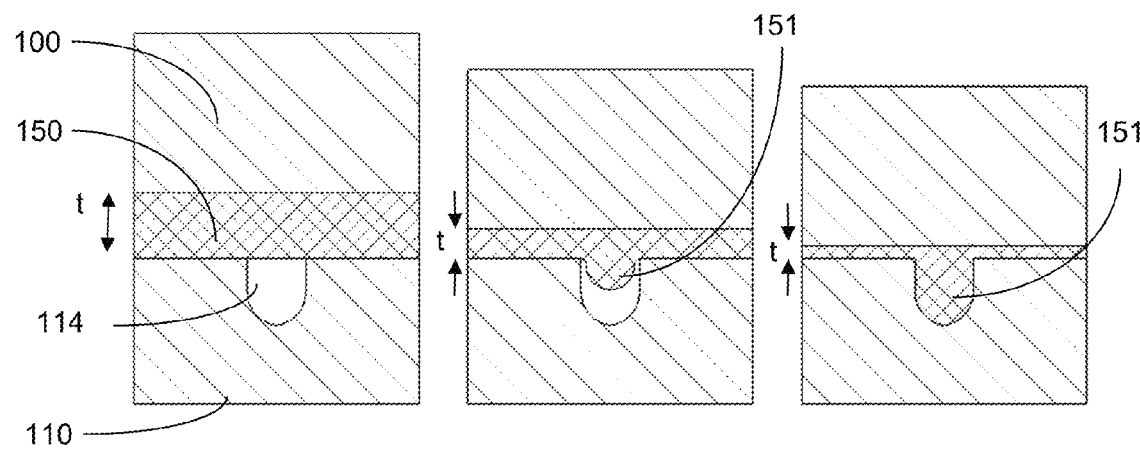
FIG. 9B illustrates a series of cross-sectional views of a microfluidic device where the channels are being sealed in accordance with some embodiments.

The cross-sectional view provided by FIGS. 9A-9B show a process of sealing a channel 114 upon appropriate actuation (e.g., compression, heating and/or other suitable method) of the sealing material. FIG. 9A shows where the cross-section is taken to illustrate FIG. 9B. In FIG. 9B, the intermediate layer 150 disposed between first and second layers 100, 110 includes a separating/sealing material.

The first and second layers 100, 110 are compressed relative to one another such that a portion 151 of the separating/sealing material is caused to deform into the space defined by the channel through which fluid would otherwise be able to flow. As shown, other portions of the separating/sealing material are also compressively deformed as well, depicted by the reduction in thickness t of the intermediate layer 150. In some embodiments, some of the portion 151 of the separating/sealing material that deforms into the channel 114 is supplied by separating/sealing material displaced from areas surrounding the channels, which contributes to the overall reduction in thickness t of the intermediate layer 150. The portion of the separating material 151 that blocks the channel, however, prevents fluid from flowing through the channel 114 between cavities that were previously in fluid communication.

In another embodiment, a portion of the first or second layer(s) itself may be deformed into the channel so as to cause sealing. For instance, the first or second layer may be composed of a deformable material, such as silicone, an elastomer, or the like. Such a material may act as a sealing material. Or, the first and/or second layer may include a material that substantially softens after the application of heat so that the material deforms into the channels.

Figure 9C:
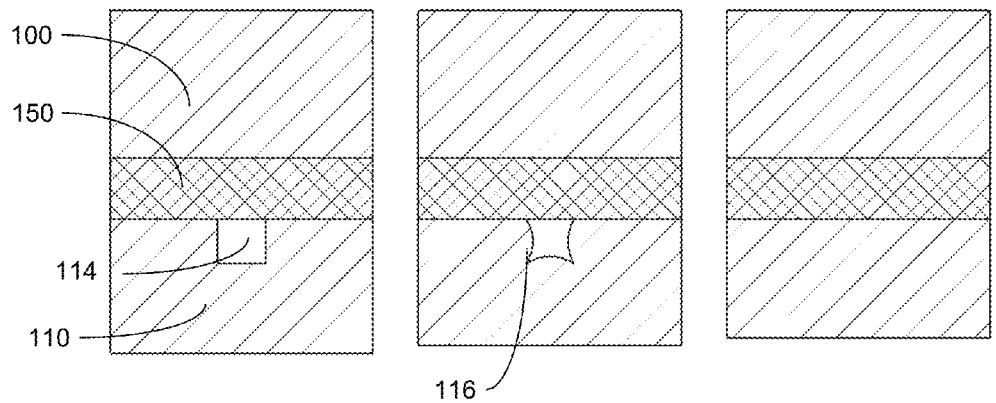
FIG. 9C illustrates a series of cross-sectional views of another microfluidic device where the channels are being sealed in accordance with some embodiments.

In some embodiments, adjacent layers are compressed relative to one another and material from one of the layers itself behaves as a sealing material and deforms into the channel space. As shown in FIG. 9C, appropriate actuation of the first or second layer(s) may cause channel collapse, that is, deformation of a portion of the sealing material 116 into the space that previously permitted fluid flow there through. Such collapse prevents fluid from flowing through the channel 114 between cavities. Accordingly, fluid located within neighboring cavities that had previously been in fluid communication is no longer able to flow between the cavities.

Figure 9D:
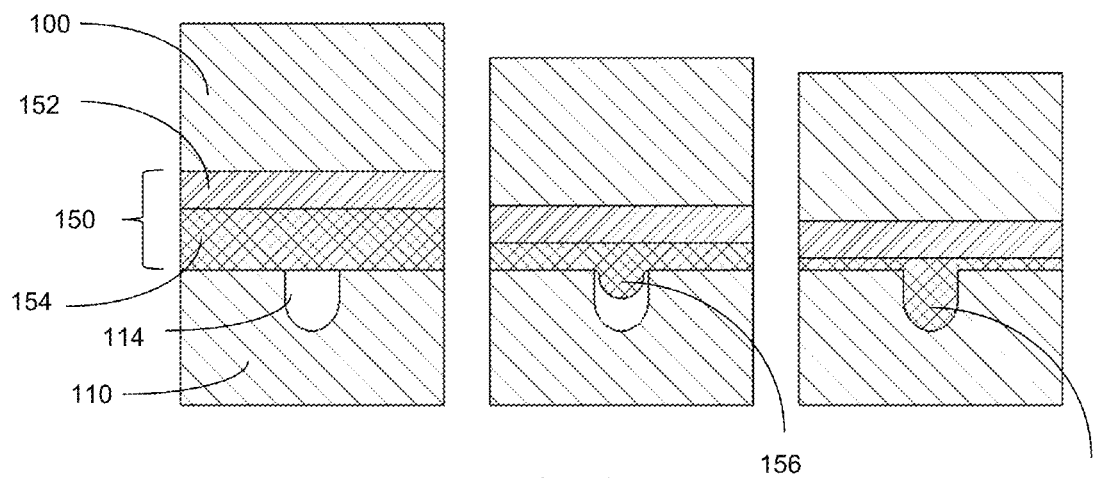
FIG. 9D depicts a series of cross-sectional views of yet another microfluidic device where the channels are being sealed in accordance with some embodiments.

In another embodiment, the intermediate layer 150 may include a distinct separating material 152 and a sealing material 154 for sealing the channels 104, 114. FIG. 9D depicts an example where the sealing material 154 is disposed directly adjacent to the channels between the separating material 152 and the channel 114.

Appropriate actuation of the sealing material 154 (e.g., application of compressive force, heating, magnetic force, etc.) may cause a portion of the sealing material 154 to be deformed into the channel 114 such that fluid is unable to flow through the channel 114 and between cavities. In some cases, such a sealing material 154 may be more susceptible to deformation (e.g., may have a lower compressive and/or thermal threshold for softening/deforming) than the separating material 152. For instance, when the layers are subject to compression relative to one another (e.g., due to an externally applied force), for this embodiment, the applied compressive force causes the portion of the sealing material 156 to deform into the channel while the separating material 152 of the intermediate layer 150 remains largely without any deformation, if at all.

In some embodiments, the process of sealing the channels is irreversible. For example, a sealing material may be plastically, hence, permanently deformed into the space of the channel through which fluid would otherwise be able to flow. Accordingly, absent disassembly of the microfluidic device to remove the sealing material from the channels, such channel sealing is not a reversible characteristic.

It can be appreciated that alternative methods of actuation may cause a sealing material to deform into the channel, sealing off fluid flow between cavities.

While separate and distinct compositions may be used as a separating material and a sealing material, as described above, the same composition may be used as both a separating material and a sealing material. For example, an intermediate layer 150 may include a membrane composed of a suitable composition (e.g., polymer, wax, or combinations thereof) that may serve to cause sealing of channels between cavities (e.g., by deformation into the channels) as well as to separate corresponding cavities of a reaction chamber from one another prior to mixing. Or, as also discussed with reference to FIG. 9C, a layer that defines cavities and/or channels may itself include a composition that serves as a sealing material to prevent fluid flow between neighboring cavities.

In some cases, any portion of the intermediate layer 150, such as the separating material 152 and/or the sealing material 154, may be used as an adhesive for bonding layers of the device together.

For instances where channels are sealed due to deformation of a sealing material into neighboring channels, any suitable methods for causing the deformation may be used. As discussed above, a sealing material may be caused to appropriately deform due to compressing layers of the device (e.g., externally applied compression, clamping/rolling of exterior surfaces of the layer(s), applying a local probe to various regions, etc.), heating appropriate portions of the device (e.g., using a thermal plate, a heat probe, a laser, etc.), magnetically actuating certain regions of the device, or any other suitable method. It can be appreciated that different regions of the device may be selectively actuated. For example, heat and/or compression may be directed to particular regions where sealing of the channels is desired, rather than to an entire surface of the device.

Figure 10A:
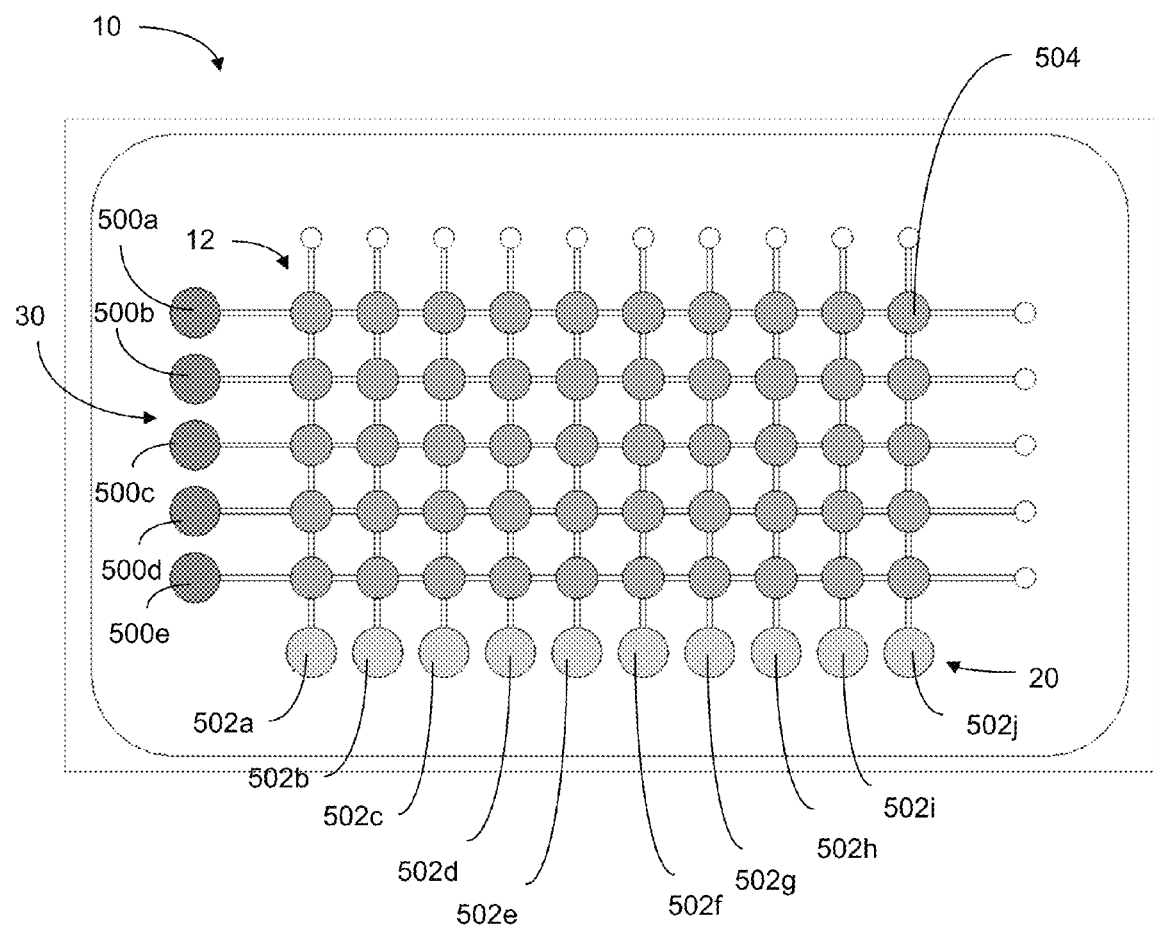
FIG. 10A shows a top view of a microfluidic device with combined cavities in accordance with some embodiments.

Once the cavities are sealed from one another, the separating material dividing corresponding cavities of each chamber may be appropriately manipulated so that the fluid ingredients 500, 502 within the cavities that make up a chamber are permitted to be combined. FIG. 10A shows an embodiment where openings are created in the separating material resulting in a mixture 504 of fluid ingredients of corresponding cavities of each chamber (shown by the shading of the chambers).

In some embodiments, the strength of the separating material may be substantially reduced when subject to a certain temperature range (e.g., above room temperature), for example, between about 20 C and about 100 C, or between about 50 C and about 90 C. Thus, when the device, or particular sections of the separating material, is heated to an elevated temperature, the portion of the separating material that divides each chamber may be prone to tearing (e.g., tearing upon application of a relatively small amount of stress), allowing contents within corresponding cavities of each chamber to mix.

In some embodiments, the separating material may be suitably weakened during manufacture/assembly of the microfluidic device. For example, the separating material may be pre-stressed (e.g., as would be the case with a shrink film) or thinned prior to assembly of various parts of the microfluidic device. Or, a separating material that includes a polymer (e.g., polyethylene, polyester, polypropylene) and/or paraffin wax may be appropriately stretched prior to attachment of the different layers/layers of the microfluidic device. In some embodiments, the separating material is attached to different adjacent layers while it is in its stretched state, so that the material is under stress in the assembly. Alternatively, certain features that serve to weaken the separating material (e.g., scoring/cut/perforated configurations) while retaining fluid separation between cavities may be added at particular locations (e.g., regions that divide each chamber into corresponding cavities).

Figure 10B:
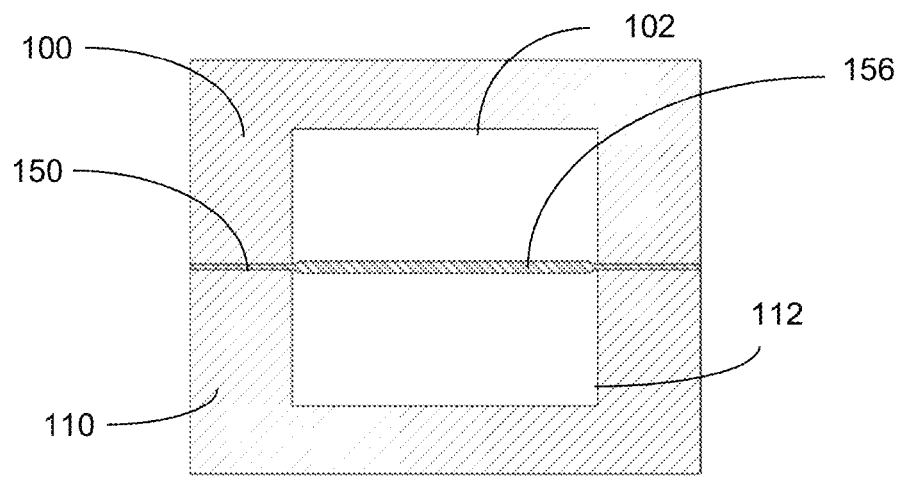
FIG. 10B illustrates a cross-sectional view of a microfluidic device with a thinned separating material in accordance with some embodiments.
Figure 10C:
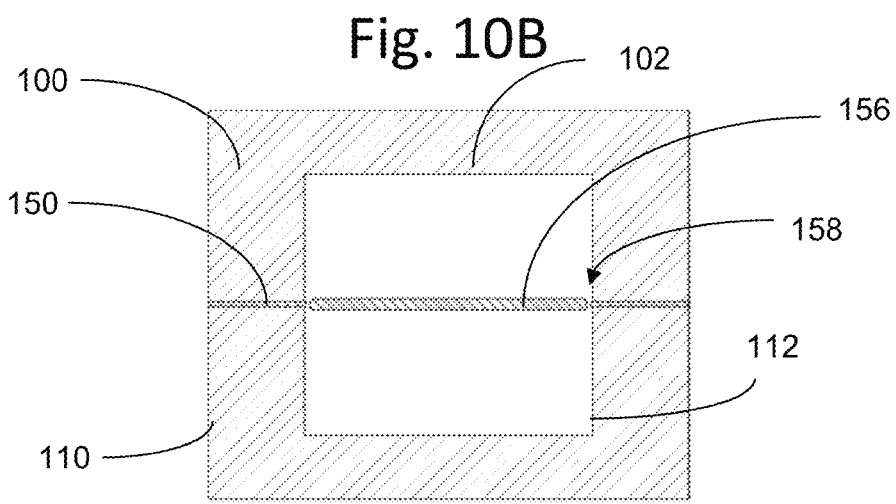
FIG. 10C depicts a cross-sectional view of a microfluidic device with corresponding cavities combined in accordance with some embodiments.
Figure 10D:
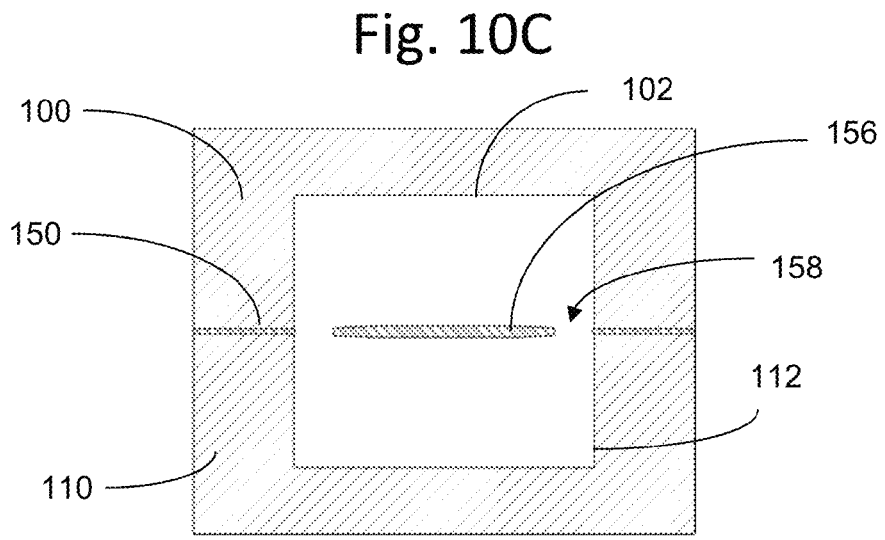
FIG. 10D depicts another cross-sectional view of a microfluidic device with corresponding cavities combined in accordance with some embodiments.
Figure 10E:
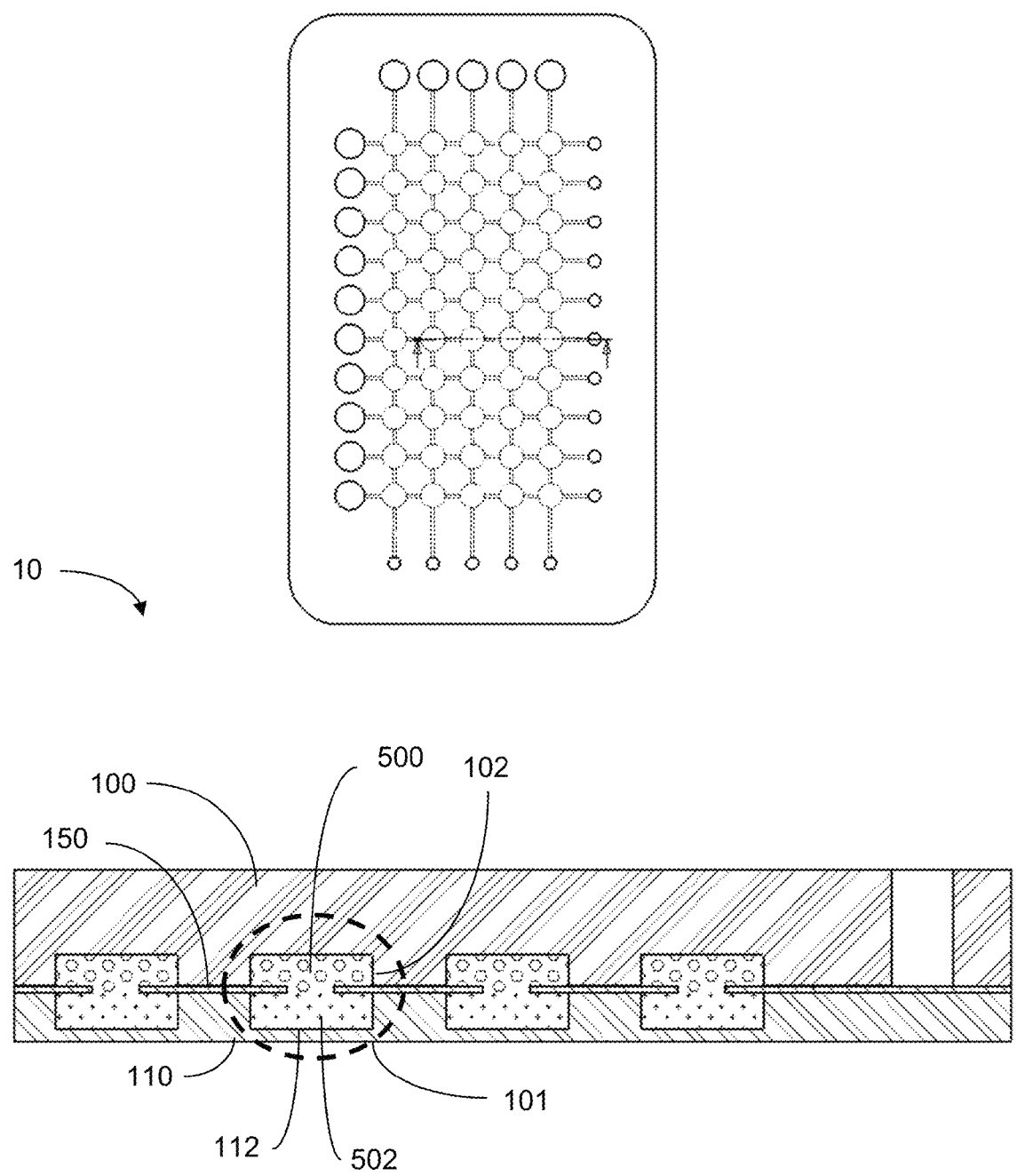
FIG. 10E shows another cross-sectional view of a microfluidic device with corresponding cavities combined in accordance with some embodiments.
Figure 10F:
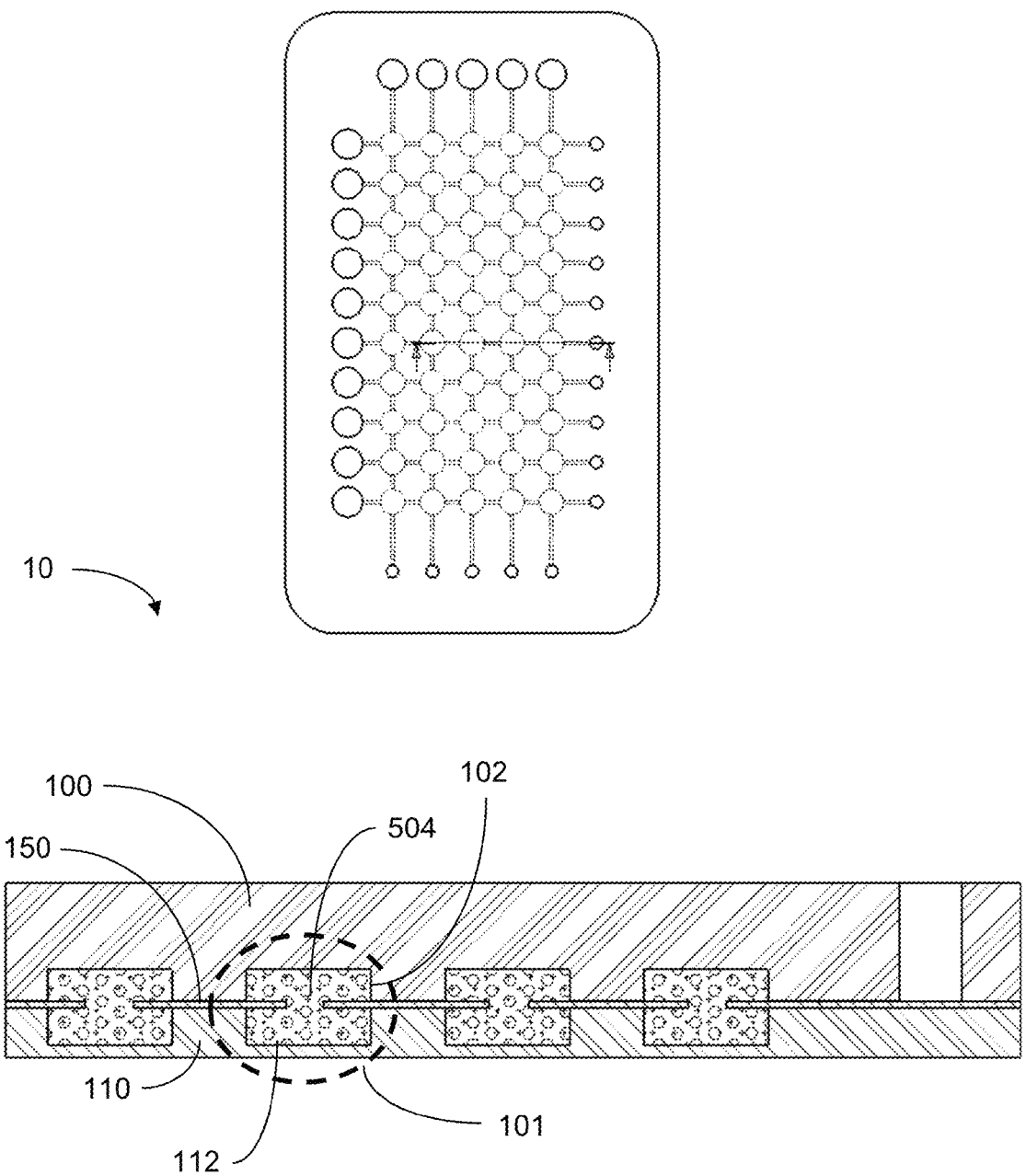
FIG. 10F illustrates another cross-sectional view of a microfluidic device with where fluid ingredients in corresponding cavities are mixed in accordance with some embodiments.

In some embodiments, by virtue of different layers of the device being compressed during sealing of the channels, the separating material may be weakened at the edge of each chamber. For instance, in FIG. 10B, the intermediate layer 150 includes a separating/sealing material that serves to seal the channels between cavities and also to provide initial fluid separation between corresponding cavities of a reaction chamber. When the channels between cavities are sealed, the separating material is depicted in FIG. 10B to be relatively thinner in regions surrounding the cavities, for example, due to compression of the layers relative to one another, heating and/or any other method. That is, as portions of the separating material are compressed during sealing of the channels, the separating material may be made relatively thinner at the edges of chambers as compared to in the middle of the chamber where no compressive force is applied. Accordingly, the separating material in the center of the chamber will remain at its original thickness.

As a result, the separating material may be more prone to tearing at edges of the cavities. Thus, when the separating material is heated, dissolved, compressed and/or otherwise suitably manipulated, openings may be formed in the separating material (e.g., from tearing) at the thinner/weakened sections near the edges of chambers. Such openings allow fluid ingredients 500, 502 to combine forming a mixture 504, as further shown in FIGS. 10C-10F. In some embodiments, a torn portion of the separating material 156 remains within the chamber.

In some embodiments, to facilitate tearing, as discussed above, the separating material may be stretched prior to adherence to the first and second layers. Placing the separating material under a pre-stress may allow for subsequent manipulation of the material to stretch, tear and/or deform in a controlled manner. For some materials, such as shrink film, the material may be stretched during manufacturing. For example, upon the application of heat, the material shrinks. Such shrinking may promote tearing of the material and may also serve to widen openings in the material, facilitating further fluid communication between the first and second cavity. Alternatively, if the separating material is in a stretched state while being attached to different adjacent layers, larger openings may be created than would otherwise form upon appropriate manipulation (e.g., heating, dissolving). Such stress may further promote tearing of the separating material.

When appropriate, the separating material may be pre-stretched at regions apart from certain channels of the device, or pre-stretched apart from as many channels as possible, so as to decrease the possibility of undesirable tears forming along or over channels that would break the seal between cavities. In some embodiments, the direction of stretch in the separating material can be chosen so that it does not extend substantially parallel to selected channels in order to reduce folding/creasing of the material into these channels.

As discussed previously, the separating material may be a continuous sheet or membrane. Though, the separating material may also include a number of individual components that are separate and distinct from one another. As such, individual components of the separating material may include different material compositions. For example, as discussed previously, the portion of a separating material that is located between corresponding cavities of a chamber may include a heat sensitive composition that is susceptible to deformation (e.g., tearing) upon exposure to elevated temperatures.

Alternatively, the portion of a separating material that is located between corresponding cavities of a chamber may include a resorbable composition (e.g., polyethylene glycol, PLA, PLGA, etc.) that may be dissolved, at least partially, when exposed to an appropriate environment (e.g., aqueous, solvent). For example, portions of the separating material may be soluble in certain solutions such that upon exposure to the solution, the soluble portion dissolves, leaving an opening between previously divided cavities of a reaction chamber. In some embodiments, the solution that instigates dissolving of the separating material may be the fluid ingredient(s) supplied to the cavities itself. In some embodiments, the separating material, or portions thereof, may be substantially soluble when exposed to particular fluids above a certain temperature; thus, heating of the material may increase its solubility.

It can be appreciated that a number of different types of separating materials may be used.

In some embodiments, the separating material may include an adhesive composition. While regions of the separating material that provide fluid separation between corresponding cavities of a chamber may be removed, surrounding areas of the separating material may include an adhesive (e.g., silicone adhesive) that assists in bonding layers together. Such an adhesive may also flow upon compression of the device for sealing of the channels.

In some embodiments, the separating material is embedded with a ferromagnetic or magnetic material. Accordingly, after filling and fluid isolation of the cavities, the separating material may be placed under an external magnetic field to create a stress that results in the creation of an opening in the separating material that permits fluid ingredients contained within corresponding cavities of a chamber to be combined.

In some embodiments, laser irradiation may be used to form openings in the separating material. For example, the separating material may be adapted to absorb a greater intensity of radiation at a particular wavelength range (e.g., ultraviolet, infrared, visible) than wavelengths outside of this range. In some cases, the material that defines the channels and cavities (e.g., material of a layer that has the relative space of cavities and/or channels etched in) may be substantially less absorptive of radiation at wavelengths within this range, allowing radiation to pass through the material without substantial heating or deformation. Such a characteristic allows for a majority of the radiation to be absorbed by the separating material, rather than having been attenuated by a different absorptive material. In some cases, treatment of the separating material with a dye having a high absorption ratio within a particular wavelength range may impart the material with selective absorption properties. Accordingly, when a separating material treated with a wavelength-sensitive dye is exposed to laser irradiation at a wavelength range corresponding to the relatively high absorption for the dye-treated separating material, openings may form in those portions of the separating material exposed to the laser irradiation.

In various embodiments, sealing of channels between cavities occurs before openings are created between corresponding cavities of each chamber. That is, after fluidly connected cavities defined by the same layer are appropriately filled, the cavities are fluidly isolated from one another as well as other cavities in the same layer. In some embodiments, such fluid isolation of the cavities occurs prior to combination of fluid within corresponding cavities of a chamber. This order of process may be advantageous because if openings are formed in the separating material between corresponding cavities of a chamber before neighboring cavities are fluidly isolated from one another, then fluid from those cavities may undesirably leak into surrounding cavities.

In some cases, sealing of channels to fluidly isolate neighboring cavities of the same layer (e.g., via deformation of a separating/sealing material) and creation of openings (e.g., tearing) of separating material between corresponding cavities from different layers may happen simultaneously, or fluid isolation may occur soon after combining corresponding cavities of the chamber. Though, to mitigate cross-contamination of fluid ingredients, sealing of channels between cavities of the same layer would happen before respective fluid ingredients are able to diffuse or mix undesirably into neighboring cavities.

Referring back to the example of FIG. 4, once openings are formed in the separating material of each chamber so as to allow mixing of the contents of the two corresponding cavities, fifty separate combinations of the reagents supplied to respective inlets 20, 30 are created. For a series of PCR reactions, once appropriate mixing has occurred, the device is then ready for thermal cycling. In this example, only three layers (i.e., first layer 100, second layer 110 and intermediate layer 150) are used to produce fifty combinations of reagents (any appropriate set of combinations of reagents may be made) where each chamber is also in fluid isolation from the other chambers.

With such a simple construction, a disposable microfluidic device can be easily manufactured, quickly and at low cost. In some embodiments, one or more of the layers of the microfluidic device is disposable; or one or more layers may be reusable after suitable washing to remove residual reagents/products.

The microfluidic device may include, without limitation, any appropriate number of reaction chambers and cavities corresponding to any appropriate number of reagents to be combined. For example, another format of chambers may include 12×96 (1152 reaction chambers) or 12×32 (384 reaction chambers) arrays of chambers and cavities. It should be understood that this device can be designed to include any desired number of chambers and cavities, corresponding to any desired number of DNA samples and any solution, as the present disclosure is not limited in this respect.

Each chamber and each cavity corresponding to the chamber may define any suitable volume. For example, the volume of chambers of microfluidic devices described may be less than about 10 microliters, less than about 1 microliter, less than about 500 nanoliters, less than about 200 nanoliters (e.g., about 150 nanoliters), less than about 100 nanoliters, less than about 50 nanoliters, less than about 20 nanoliters, less than about 10 nanoliters, less than 5 nanoliters, less than about 1 nanoliter, or any other appropriate volume. The volume defined by cavities corresponding to a particular chamber may also vary. Accordingly, the volume of corresponding cavities of a chamber may be about equal or may substantially differ.

In some embodiments, the microfluidic device provides for the ability to combine three or more reagents instead of two. Accordingly, the microfluidic device may be constructed into an array of chambers where each chamber includes three or more corresponding cavities. Each of the corresponding cavities may be filled, subject to fluid isolation from neighboring cavities, and the corresponding cavities which were previously separated from one another may be fluidly connected so as to allow for mixing of the contents within.

Examples of devices that are able to combine three different reagents within a reaction chamber are shown in FIGS. 11A-12B. Though, it can be appreciated that microfluidic devices in accordance with the present disclosure may be configured and arranged to mix together any suitable number of distinct reagents in different combinations.

Figure 11A:
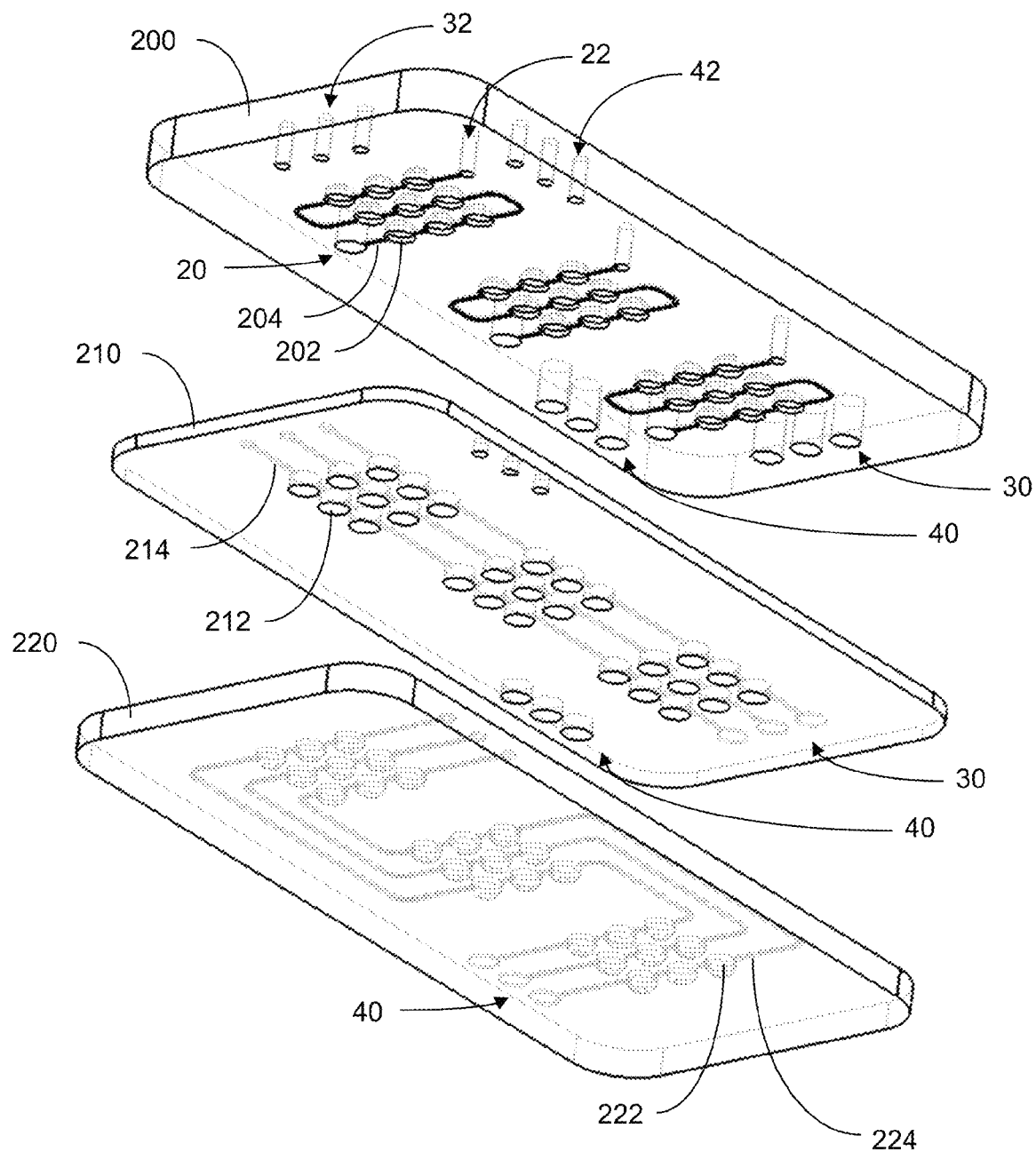
FIG. 11A shows an exploded perspective view of portions of yet another microfluidic device in accordance with some embodiments.
Figure 11B:
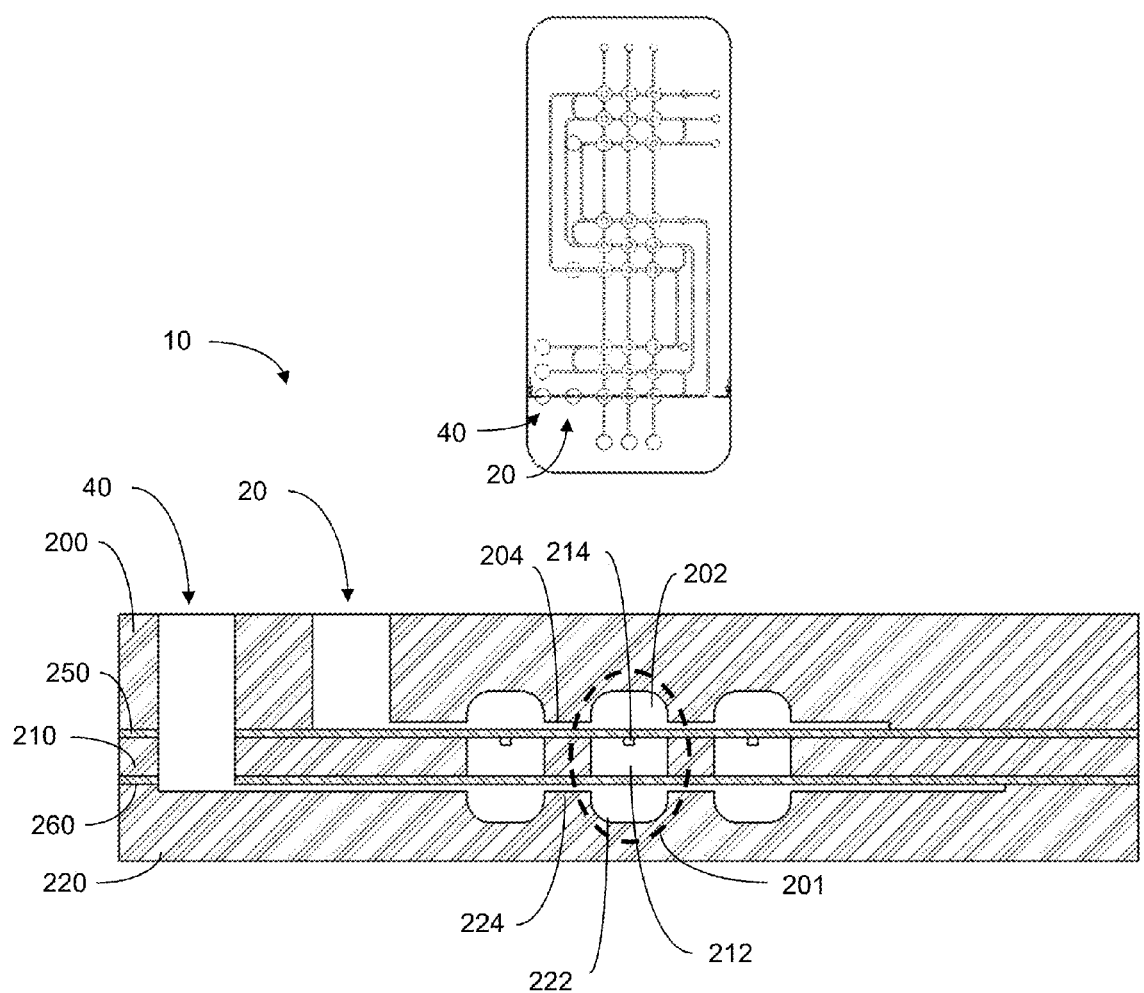
FIG. 11B illustrates a cross-sectional view of the microfluidic device of FIG. 11A.

FIGS. 11A-11B depict an embodiment of a microfluidic device that facilitates the combination of three different reagents in each reaction chamber. Here, the device includes a first layer 200, a second layer 210 and a third layer 220. Shown in FIG. 11B, intermediate layers 250, 260 are provided on either side of the second layer 210; the first intermediate layer 250 is positioned between first layer 200 and second layer 210, and the second intermediate layer 260 is positioned between second layer 210 and third layer 220.

In this embodiment, chambers in which reactions are contemplated to occur are formed by three corresponding cavities across three layers where each of the layers and, hence, cavities are separated by respective separating materials prior to being fluidly connected.

As shown, the first layer 200 is formed to include a number of inlets 20 for filling cavities 202 that are in fluid connection via channels 204. Each inlet with cavities 202 and channels 204 is also connected to a vent 22 to accommodate potential overflow of fluid ingredient and for exhausting excess gas.

Also, the first layer 200 and second layer 210 include inlets 30 and vents 32 for appropriate supply of cavities 212 which are in fluid communication via channels 214. The inlets 30 extend through the first layer 200 to the second layer 210 so that appropriate fluid ingredients may be added at the surface of the first layer 200 from fluid source reservoirs and flow into the cavities and channels of the second layer 210.

Further, the first layer 200, second layer 210 and third layer 220 include inlets 40 and vents 42 for appropriate supply of cavities 222 which are in fluid communication via channels 224. The inlets 40 extend through the first layer 200 the second layer 210 and to the third layer 220 so that appropriate fluid ingredients may be added at the surface of the first layer 200 from fluid source reservoirs and flow into the cavities of the third layer 220.

The cross-sectional view of FIG. 11B shows a reaction chamber 201, indicated by the dashed circled region, having corresponding cavities 202, 212, 222 that are initially separated by layers 250, 260. In operation, fluid ingredient is provided through inlet 20 to the cavities 202 of the first layer 200. Further fluid ingredient is provided through inlet 30 to the cavities 212 of the second layer 210. Additional fluid ingredient is provided through inlet 40 to the cavities 222 of the third layer 220. Once the cavities and channels of each of the layers are appropriately supplied with respective fluid ingredients, the channels of each layer are sealed via any suitable method (e.g., methods described above involving a sealing material), resulting in fluid isolation of the cavities. Then, openings are formed in the separating material of the layers 250, 260 that initially had divided corresponding cavities 202, 212, 222. Such openings allow the contents within those cavities corresponding to the chamber 201 to mix.

Figure 12A:
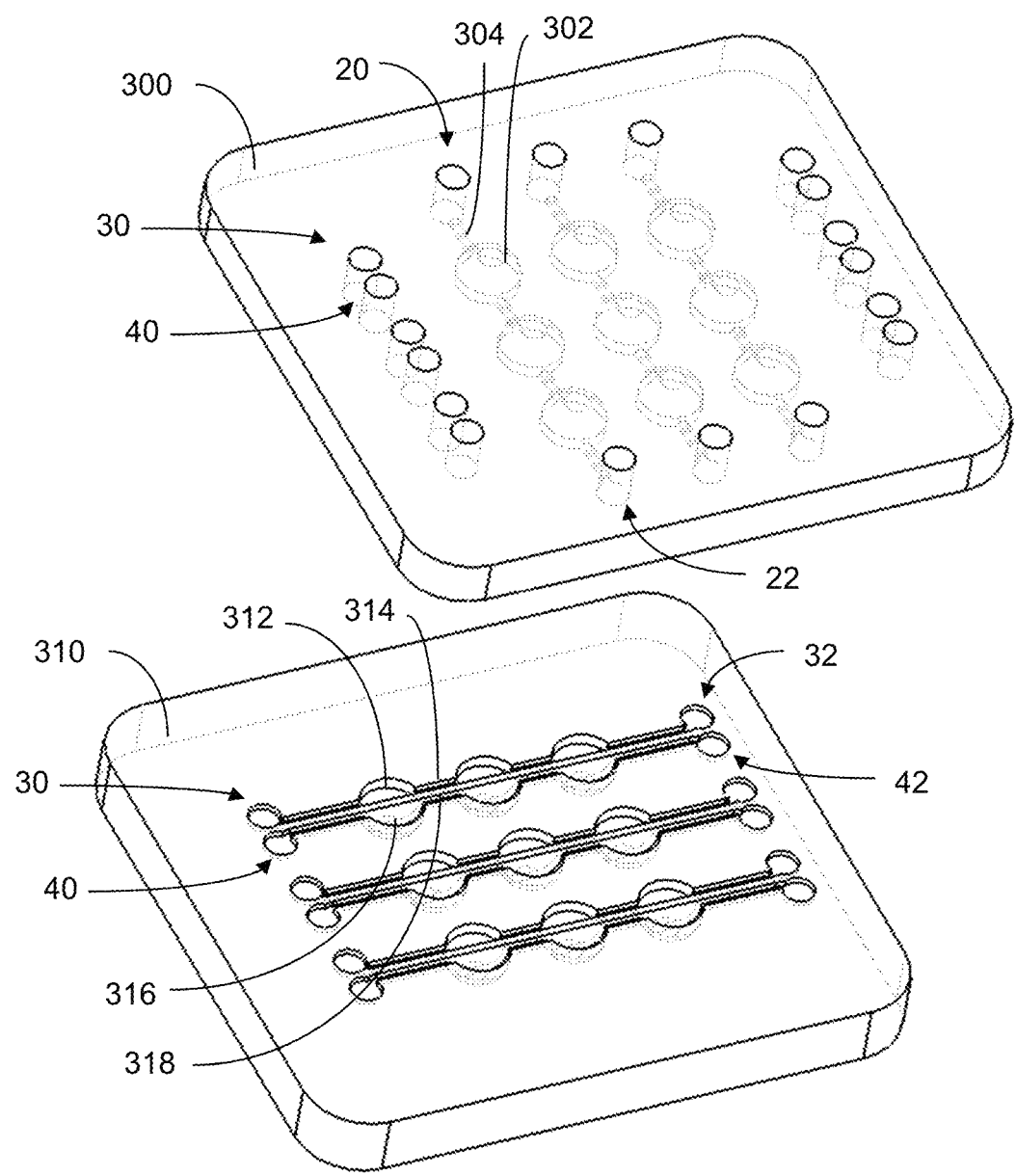
FIG. 12A shows an exploded perspective view of portions of another microfluidic device in accordance with some embodiments.
Figure 12B:
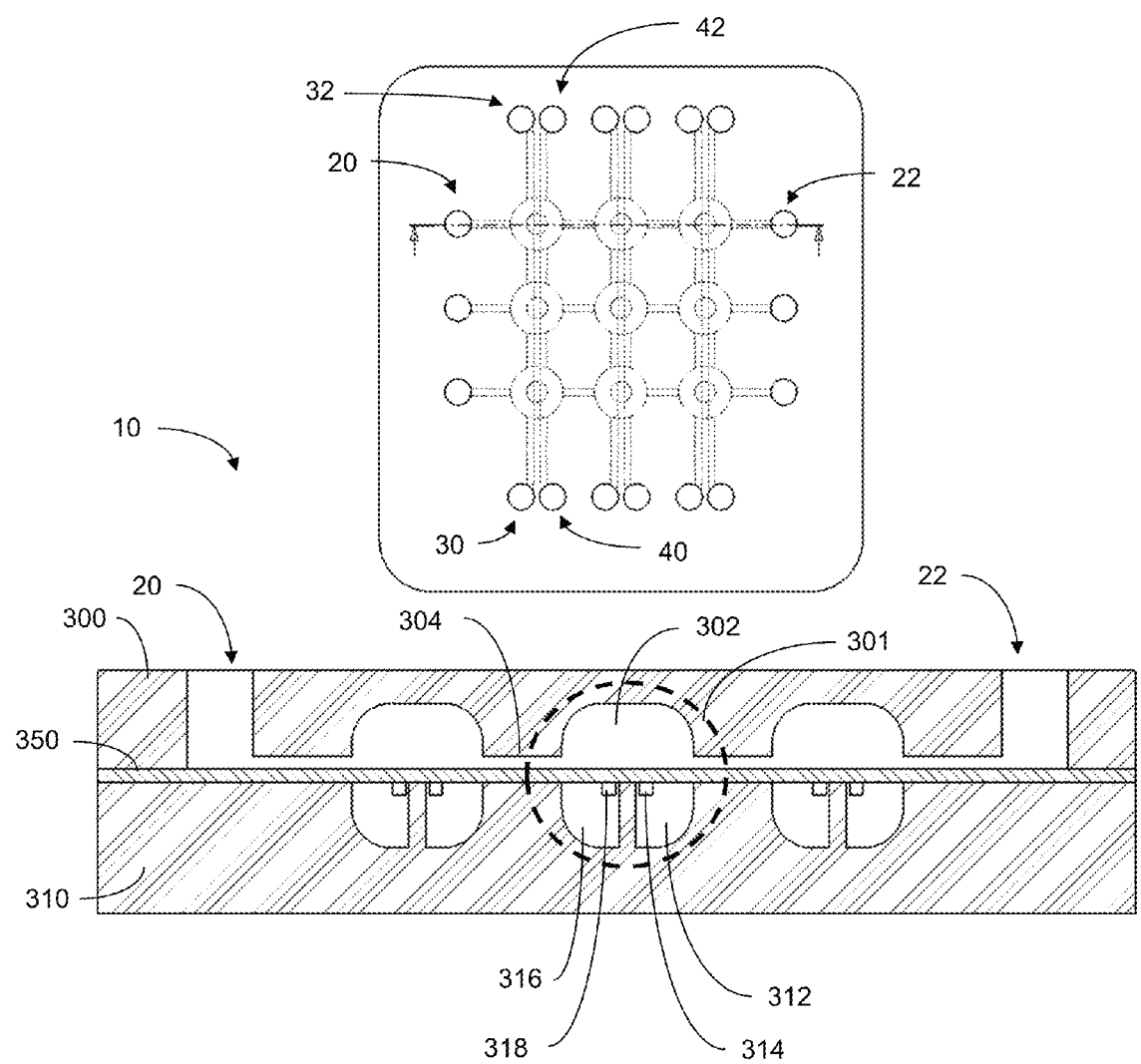
FIG. 12B illustrates a cross-sectional view of the microfluidic device of FIG. 12A.

FIGS. 12A-12B depict another embodiment of a microfluidic device that is able to combine three different reagents in a reaction chamber. In this embodiment, an intermediate layer 350 including a separating/sealing material is disposed between a first layer 300 and a second layer 310. Similar to the embodiment shown in FIGS. 11A-11B, chambers in which reactions are contemplated to occur are formed by three corresponding cavities. However, one of the corresponding cavities of each chamber is defined by the first layer 300 and the other two cavities are defined by the second layer 310. The intermediate layer 350 is used to separate cavities corresponding to a chamber, so only one intermediate layer (having a separating/sealing material) and two layers (e.g., layers that are stiffer) disposed on either side are used for the three-cavity chambers, as opposed to the two intermediate layers and the three layers (e.g., layers that are stiffer) in an alternating arrangement, as provided in the embodiment of FIGS. 11A-11B.

As shown, the cavities 302 of the first layer 300 are shown to be larger in volume than the cavities 312, 322 of the second layer 310. It can be appreciated that the shape (e.g., depth, contour, etc.) of the cavities 302, 312 and 322 may be appropriately determined so as to allow for any suitable ratio of combination of the different fluid ingredients. A number of inlets 20 are provided for filling cavities 302 via channels 304, with associated vents 22 to accommodate possible overflow of fluid ingredient and excess gas. The second layer 310 includes inlets 30 and vents 32 that are arranged to supply cavities 312, which form a fluid connection with channels 314, with fluid ingredient. The second layer 310 also includes inlets 40 and vents 42 which are arranged to supply cavities 316 via channels 318 with fluid ingredient.

FIG. 12B shows a cross-sectional view of the device of FIG. 12A, where one of the reaction chambers 301 is indicated by the dashed circled region. The chamber has corresponding cavities 302, 312, 316 which are all initially separated by the separating material of layer 350. In use, fluid ingredient is provided through inlet 20 to the cavities 302 of the first layer 300. Further fluid ingredient is provided through inlet 30 to the cavities 312 of the second layer 310. Additional fluid ingredient is provided through inlet 40 to the cavities 316 of the second layer 310.

When the cavities and channels of each of the layers are appropriately filled with respective fluid ingredients, the channels of each layer are sealed via any suitable method, resulting in fluid isolation of the cavities. Then, openings are formed in portions of the separating material that divides corresponding cavities 302, 312, 316 from one another so as to allow contents within all three of the cavities to mix.

It can be appreciated that embodiments of the present disclosure are not meant to be limiting in their particular configuration or arrangement. Accordingly, any suitable number of groups of reagents can be combined, as the present disclosure is not limited in this regard.

In some embodiments, channels connecting adjacent cavities are routed in such a manner so as to limit the area occupied by the channels on the device. For example, channels may be arranged to incorporate multiple bends, allowing for fine control of the distance of channels and between cavities. Control over the distance between channels may assist in controlling bond quality between layers of the device, for example, by providing room for material (e.g., sealing material, fluid, etc.) to be displaced such that the displaced material does not interfere with other components/features of the device.

In some embodiments, layers defining channels that are spaced closer together may exhibit a greater bond quality between layers as compared with layers defining channels that are spaced farther apart, for example, due to potential overflow of material from the channels upon compression. That is, channels that are spaced so as to take up more sealing material (e.g., closer together) upon compression may provide for generally even bonding between layers while channels spaced further apart may take up less sealing material making the sealing material more prone to bunching, hence, decreasing overall bond quality. As discussed further below, the device may include additional space(s) (e.g., relief chambers, additional cavities) that provide room into which excess materials (e.g., fluid ingredient, sealing material, air, etc.) may enter.

In some embodiments, a number of cavities of the device are connected to a relief chamber which functions to reduce the pressure of fluid inside the cavities, particularly if and when the device is compressed.

Figure 13A:
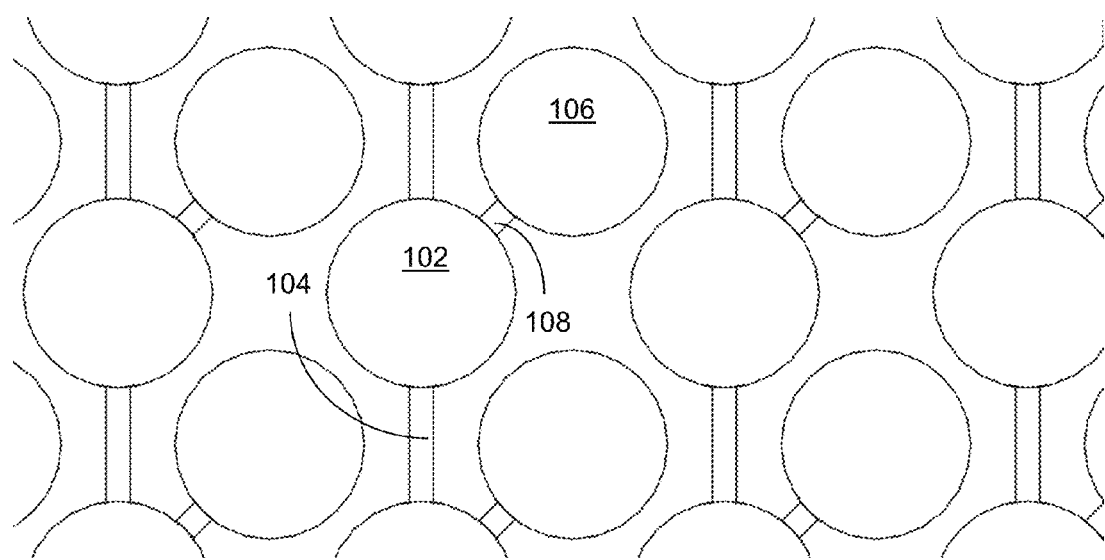
FIG. 13A shows a top view close-up of a microfluidic device in accordance with some embodiments.

FIG. 13A depicts a number of relief chambers 106, in which reactions (e.g., PCR) are not intended to occur, each chamber 106 connected to a cavity 102 via a channel 108. Each relief chamber 106 has a compressible volume of air that remains within the relief chamber as liquid fills into the cavities. In some embodiments, the relief chamber 106 has only one channel for entry and exit of fluid, substantially preventing the compressible volume of air contained within the chamber from escaping, i.e., the relief chamber is effectively a dead end. Accordingly, the compressible volume of air within relief chambers provides a built-in mechanism that discourages filling of the relief chamber(s) with fluid ingredient while cavities 102 are initially being filled, yet also provides overflow space for the fluid ingredient from the cavities 102 upon compression of the device.

In embodiments where the layers of the device are compressed relative to one another so that channels of the device are sealed with a sealing material, the volume inside the cavities may be reduced, leaving less occupancy space for fluid within the cavities. For a cavity 102 connected to a relief chamber 106 and filled with liquid ingredient, during compression, an excess volume of liquid may overflow from the cavity 102 into the relief chamber 106. The ability for the excess volume of liquid to overflow from the cavity into the relief chamber compresses the air located within the relief chamber but also allows for the reduction of pressure and/or resistance buildup within the device to occur.

In some embodiments, the depth of the channels may affect whether a seal is properly formed within a channel that otherwise fluidly connects neighboring cavities. When the device is subject to an externally applied compressive stress, a shallow channel is more likely to result in a properly formed seal that prevents fluid flow therein as compared to a deeper channel. That is, comparatively less deformation (e.g., provided by applied compression) of the sealing material is required to create a suitable seal in a smaller space, allowing for a fine degree of channel sealing control. Accordingly, the depth of the channels may be designed so as to promote, or discourage, sealing.

In some embodiments, channels that connect cavities to other cavities may be more shallow in depth than channels that are closer to fluid source reservoirs or those that connect cavities with pressure relief chambers. Accordingly, channels that connect cavities to one another may be more easily sealed than channels that are connected to other features of the device.

In some embodiments, the channel depth may vary along the same channel. For example, a channel connecting the first cavity along a channel with a fluid source reservoir in a subset of cavities may require an especially tight seal to be formed near the cavity but such a tight seal might not be required closer to the fluid source reservoir. As a result, the region of the channel nearest to the cavity may be more shallow than the region of the channel nearest to the fluid source reservoir. Or, in some embodiments, deeper regions of a channel may remain substantially unfilled by a sealing material upon compression of the device, and shallower areas may become obstructed and filled by the sealing material upon compression of the device.

Channels which require sealing may have a sufficient amount of a sealing material located around or in otherwise close proximity to the channels so that a sufficient amount of the sealing material may be deformed into the channels during sealing actuation (e.g., compression and/or heating). Accordingly, sealing channels, such as those that fluidly connect cavities with each other, may be constructed to be longer or further away from other features (e.g., fluid source reservoirs, relief chambers) so that more sealing material is available to deform into the channels. And for channels where sealing is not preferable, such as those that connect cavities with relief chambers, the channels may be relatively short and deep so that sealing of these channels does not occur as readily.

In some embodiments, the device may be formed to include additional cavities, or pockets, at appropriate locations that are arranged to collect excess fluid and/or sealing material that may be displaced from various cavities or channels during heating and/or compression of the device. Such additional cavities are generally not intended to house a reaction, and may be connected to vents so as to remain unpressurized after steps of compression/heating of the device. The additional cavities may be located at regions of the device that would otherwise become partially or completely filled with sealing material, for example, cavities or channels at the edge of an array where overflow may be more likely to occur.

Figure 13B:
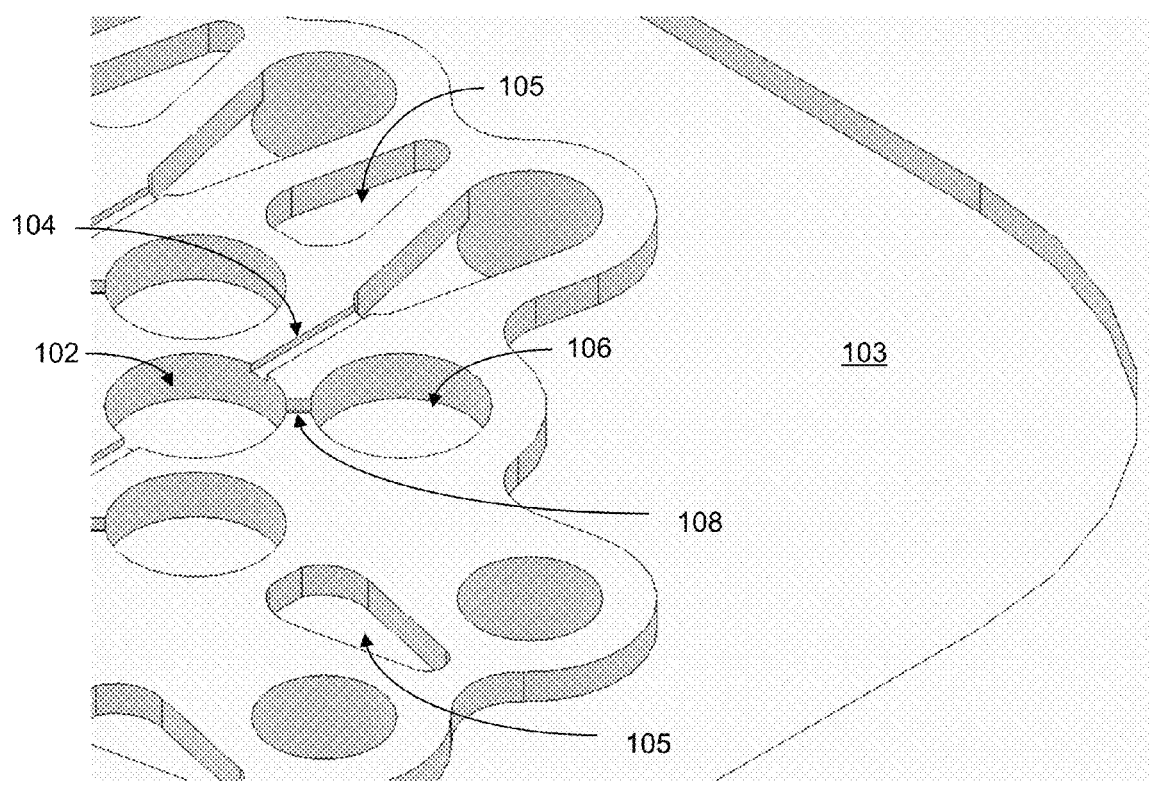
FIG. 13B depicts a perspective view close-up of a microfluidic device in accordance with some embodiments.

FIG. 13B shows additional cavities 103, 105 of the device that may be suitable for collecting excess sealing material. For example, the additional cavity 103 may collect excess sealing material that overflows resulting from compression of the region between an edge of the device and the cavity. The additional cavities 105 located between fluid input reservoirs may be suitable to collect excess sealing material resulting from compression of the region between a cavity and the fluid input reservoirs, or vents.

Figure 14:
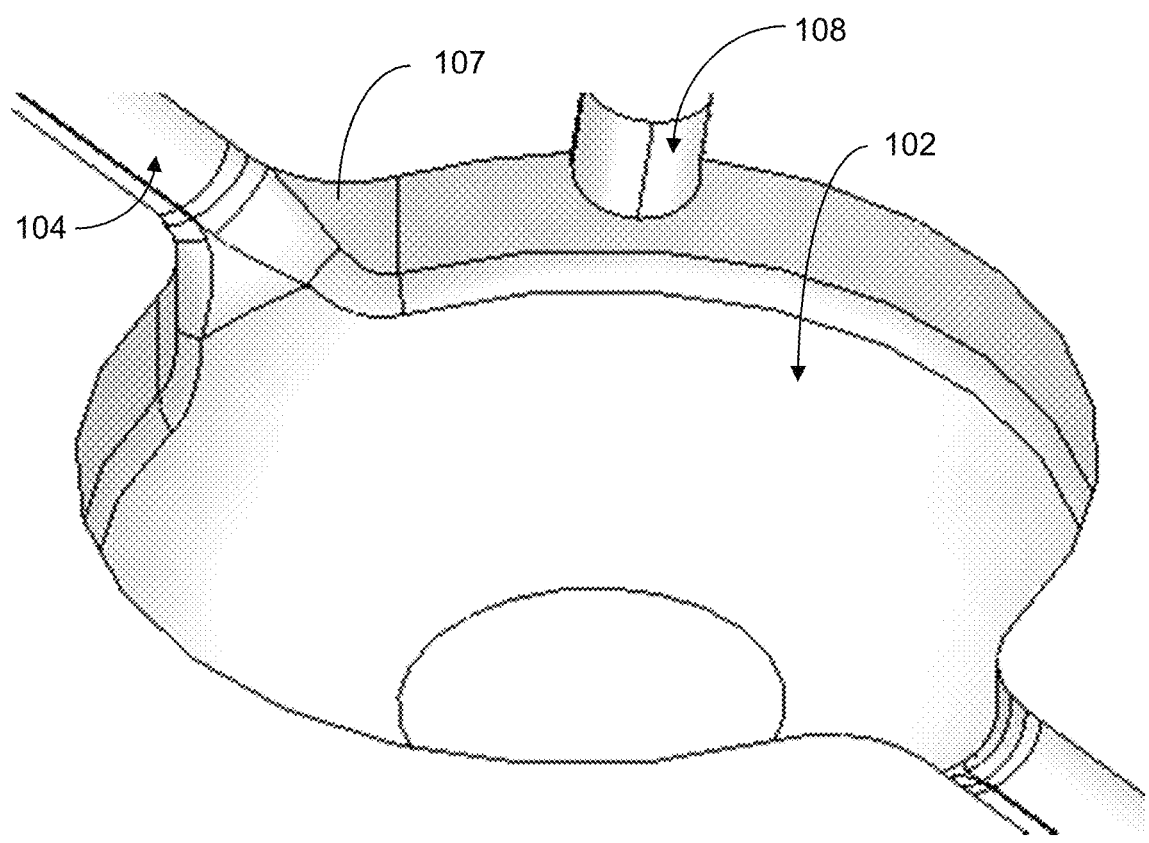
FIG. 14 depicts a perspective view close-up of a microfluidic device in accordance with some embodiments.

In some embodiments, interfaces of the device may provide for a smooth fluid flow transition between channels and cavities. For instance, FIG. 14 shows gradual interface 107 between channels and cavities that are rounded which allows fluid to flow evenly between channels and cavities. Otherwise, sharp corners between channels and cavities may result in an overall increase in fluid flow resistance within the device, for example, due to capillary resistance from liquid surface tension, or turbulent fluid flow.

In some cases, smooth interfaces between channels and cavities may reduce the overall pressure required for fluid to fill the cavities. What is more, smooth interfaces between channels and cavities may allow for channels to be more easily filled with sealing material than would otherwise arise from a sharper interface.

In some embodiments, the device may include one or more protrusions, such as ribs, inserts, bumps, ridges, etc., that effectively reduce the amount of compressive force that would otherwise be required to seal the appropriate channels. Such protrusions may, for example, be disposed in alignment with the channels so that, upon application of compressive force, compressive stresses are concentrated at channel regions so as to better facilitate sealing of the channels.

This stress concentration may promote deformation of the sealing material at the appropriate region(s) resulting in the sealing material being forced into the channels. That is, the protrusions may reduce the overall compressive force required for the cavities to be sealed. During compression, this arrangement may also result in a smaller amount of compressive stresses in regions other than channels that would otherwise be present, such as over cavity regions. Accordingly, by mitigating compressive stress concentrations in regions such as over cavity regions, the overall amount of fluid overflow/displacement to other areas of the device due to compression is reduced.

In some embodiments, such protrusions may be integral with the sealing material or in contact with the sealing material. Alternatively, the protrusions may be part of one or more layers of the device. Or, the protrusions may be part of an external device/component that may be used to compress layers of the device together. For example, the protrusions may be included as part of a thermocycler assembly, or a separate layer altogether that is used primarily for deforming the sealing material.

As discussed above, once channels of the microfluidic device are sealed such that cavities are isolated and the contents of corresponding cavities of each chamber are allowed to mix, a reaction process may be initiated. In some cases, once reagents are combined, the reaction immediately takes place. In other cases, a thermal cycling sequence occurs to initiate various parts of the reaction, such as in the case of PCR.

Once the desired reactions are completed, the results are collected. One preferred method of collecting the results is through optical techniques. Optical collection may be performed using any suitable method, such as through absorbance, fluorescence and/or luminescence of the contents of the reaction chambers. Or, each chamber may be imaged via microscopy and an operator may manually observe specific features that result from the reactions within the chambers.

In the context of PCR, once the reagents are combined, the microfluidic device would be subject to thermal cycling. In some cases, when appropriate, the thermal cycler may be the same device that provides heat and/or compressive pressure to the device for sealing the channels and deforming (e.g., tearing) the separating/sealing material(s).

Accordingly, a user could fill the device with the appropriate reagents, the steps of cavity isolation and combining fluid ingredients together that were initially separated may be performed (manually or automatically), and the device with combined reagents may be subject to thermal cycling (immediately or after a certain period of time).

In some embodiments, the thermal cycler would provide clamping of the layers of the microfluidic device together so as to result in good thermal contact and, hence, reliably quick, responsive temperature adjustments. Such clamping may also provide for a suitable amount of externally applied compression, for example, to seal off the channels between cavities.

Figure 15:
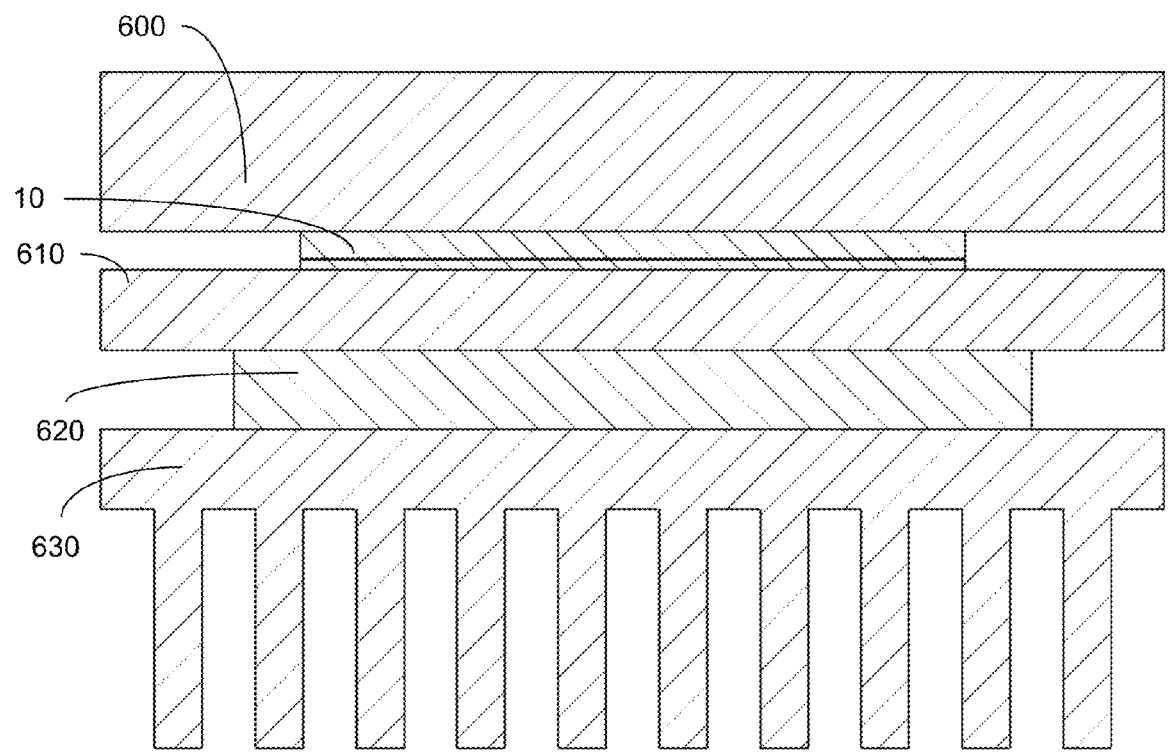
FIG. 15 illustrates a microfluidic device coupled with a thermal cycling assembly in accordance with some embodiments.

The embodiment illustrated in FIG. 15 depicts a microfluidic device 10 placed between clamping plates 600, 610 of a thermal cycler. Below plate 610, is a thermoelectric element 620 and a heat sink 630, providing temperature control to the system.

In some embodiments, to seal the channels, the thermal cycler provides for compressive force applied by clamping plates 600, 610 and/or an increase in temperature of the device 10, or portions of the device. Though, in some embodiments, at this stage, the temperature would not be high enough to cause tearing of the separating material. Once the channels are sealed, the thermal cycler may increase the temperature further to cause the formation of openings in the separating material. Once openings are formed in the separating material, reagents contained within the corresponding cavities of each chamber are combined. Once the reagents are suitably combined, the device is subject to thermal cycling appropriate for PCR to proceed.

In some cases, thermal cycling is preceded by a period of time (e.g., between 1 and 15 minutes) of high temperature exposure so as to activate the PCR enzyme. The reagents may then be cycled between two or more temperature ranges appropriate for PCR. Typically the amount of target DNA is doubled at the conclusion of each cycle.

PCR detection may be implemented in a number of ways. For instance, in end point PCR, the device undergoes a number of thermal cycles, and after thermal cycling is complete, the fluorescence of each reaction chamber is measured. In real time PCR, the fluorescence of each chamber is measured periodically during or after cycles, allowing for the amount of DNA in each chamber to be quantified in real time.

For end point PCR detection, the optical detection assembly can be completely separate from the thermal cycling assembly. Thus, the device can be moved from the thermal cycler to the optical detection assembly after thermal cycling is complete.

For real time PCR detection, an optical detection assembly may be combined with the thermal cycling assembly allowing for the device to be analyzed without having to be removed from the thermal cycler. In some embodiments, the clamping plate of the thermal cycler may be translucent to allow for reactions to be optically measured without having to remove the clamp.

In some embodiments, microfluidic devices described herein may be used for digital PCR where the amount of DNA in a sample is quantified. As discussed above, in digital PCR, a DNA sample is divided into a large number of separate aliquots. Once the sample volume is divided into the several aliquots, it is amplified through PCR, and the amount of DNA from the original sample can then be calculated by counting the number of aliquots that have undergone exponential growth through PCR. The analysis for digital PCR is a binary process where an aliquot either undergoes PCR because at least one molecule of target DNA was present within the aliquot, or the aliquot does not undergo PCR because no target DNA was present within the aliquot. Thus, the original concentration of DNA (e.g., prior to dilution) may be determined based on a calculated distribution (e.g., Poisson distribution) of positive and negative aliquots.

For digital PCR, the samples share the same master mix and primer solutions, as the goal for digital PCR is to use a large array of aliquots into which sample volumes of DNA are provided, to determine how many molecules of DNA were present in an original sample. Accordingly, it is not necessary to combine different primer solutions with each sample, as would often be the case in non-digital PCR.

Figure 16A:
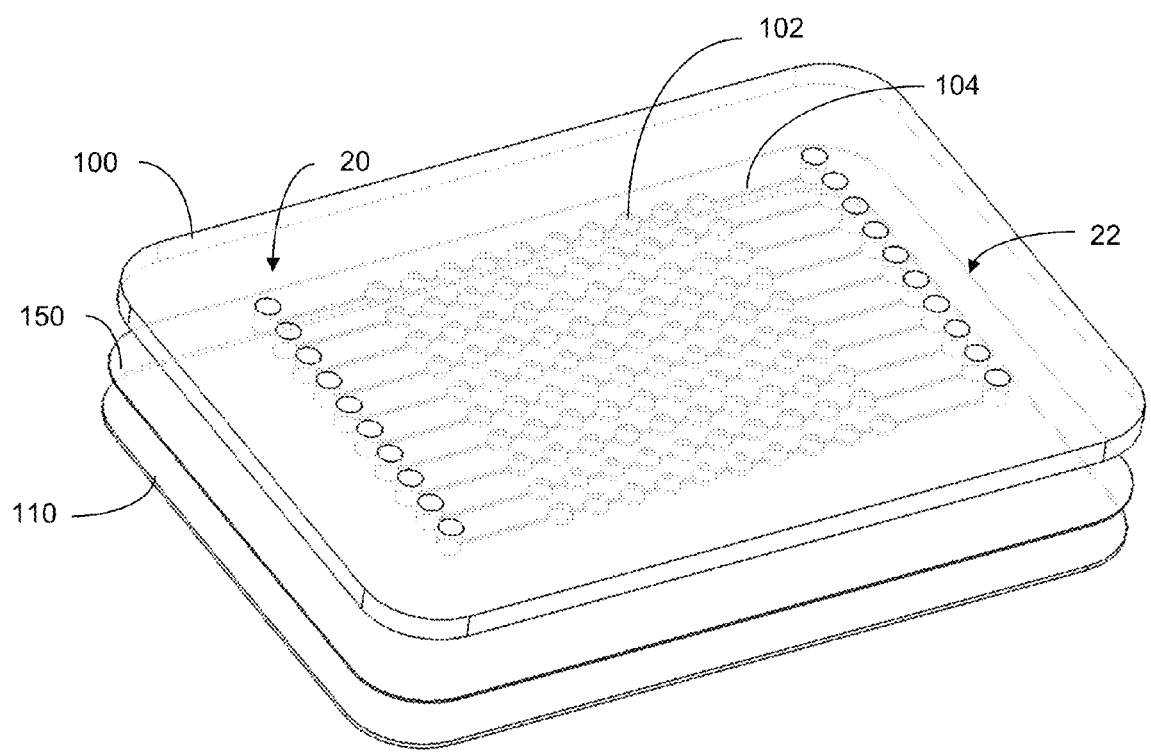
FIG. 16A depicts an exploded perspective view of another microfluidic device in accordance with some embodiments.
Figure 16B:
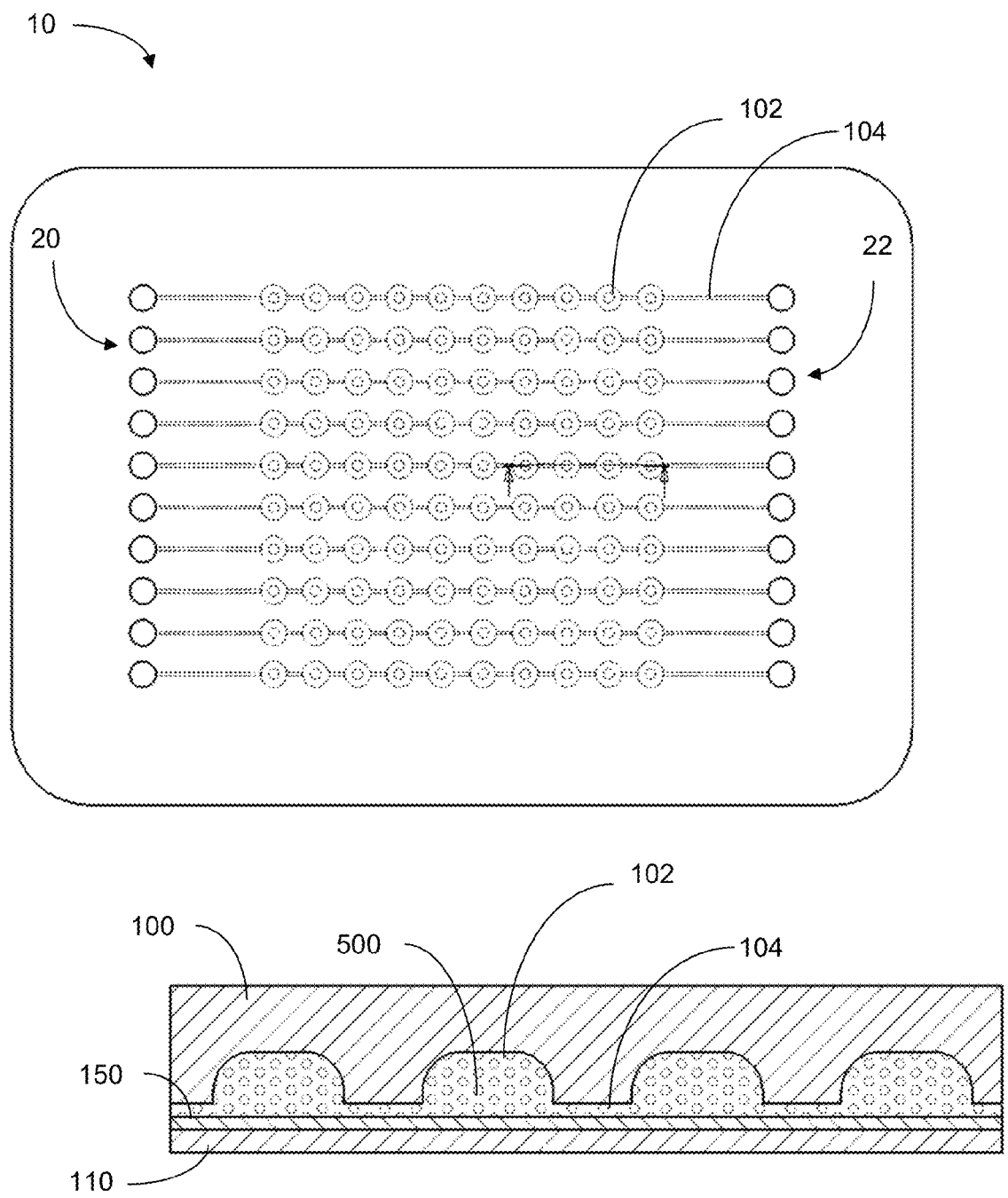
FIG. 16B shows a cross-sectional view of the microfluidic device of FIG. 16A.
Figure 16C:
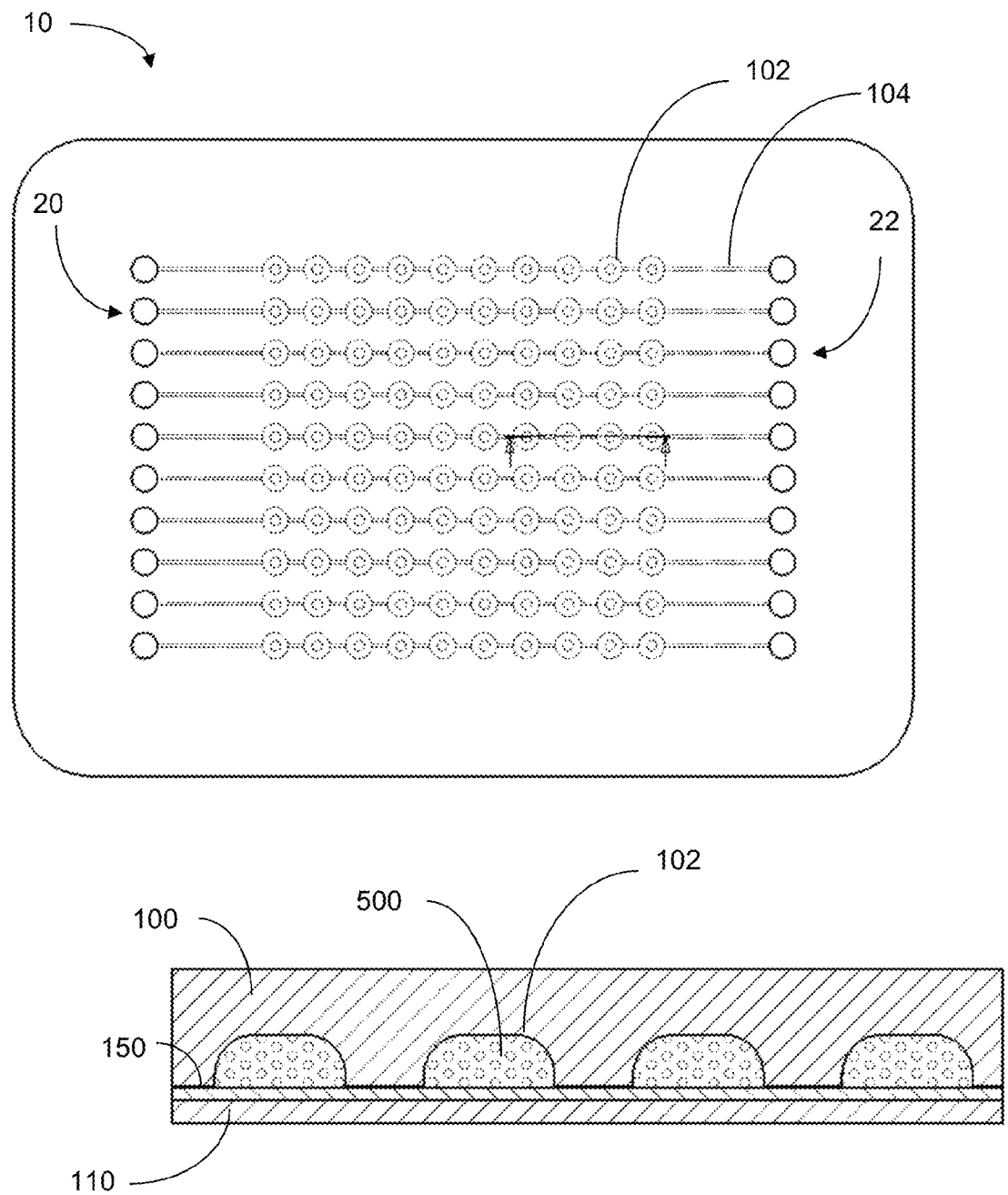
FIG. 16C shows a cross-sectional view of the microfluidic device of FIG. 16A with sealed channels.

In an embodiment of a microfluidic device that may be used for digital PCR, shown in FIGS. 16A-16C, the microfluidic device 10 includes a first layer 100, a second layer 110 and an intermediate layer 150 sandwiched between the layers. The first layer 100 includes an array of cavities 102, channels 104, inlets 20 and vents 22. In this embodiment, each reaction chamber includes a single cavity, as the second layer 110 is a material without any channels or cavities defined therein. While not meant to be limiting, the first and/or second layer(s) may include a material that is stiffer (e.g., relatively rigid in comparison) than the material of the intermediate layer. Alternatively, in some embodiments, the material of the intermediate layer is stiffer than the material making up the first and/or second layers. The intermediate layer 150 includes a sealing material that is adjacent to each of the channels 104 of the first layer 100.

While not required, the cavities 102 and channels 104 are further divided into subsets that are each fluidly connected to a respective inlet 20. Accordingly, the same fluid ingredient or different fluid ingredients may be supplied to each inlet and the cavities associated with each inlet. In some embodiments, a microfluidic device suitable for digital PCR may include single inlet that supplies a fluid ingredient to all cavities of the device through an appropriate network of channels interconnected with one another and with the cavities.

The sealing material is arranged to deform into the channels upon appropriate actuation (e.g., compression, heating, etc.) according to any suitable manner so as to provide fluid isolation between the cavities 102. As shown in FIG. 16B, prior to appropriate actuation of the device, the channels 104 permit fluid flow between cavities 102. Though, after actuation, the channels 104 are sealed causing the cavities 102 to be fluidly isolated, as shown in FIG. 16C. One of skill in the art would appreciate that any suitable method may be used to cause fluid isolation of the cavities, for example, methods described and illustrated with respect to FIGS. 9B-9D, or other techniques not explicitly shown.

Figure 17A:
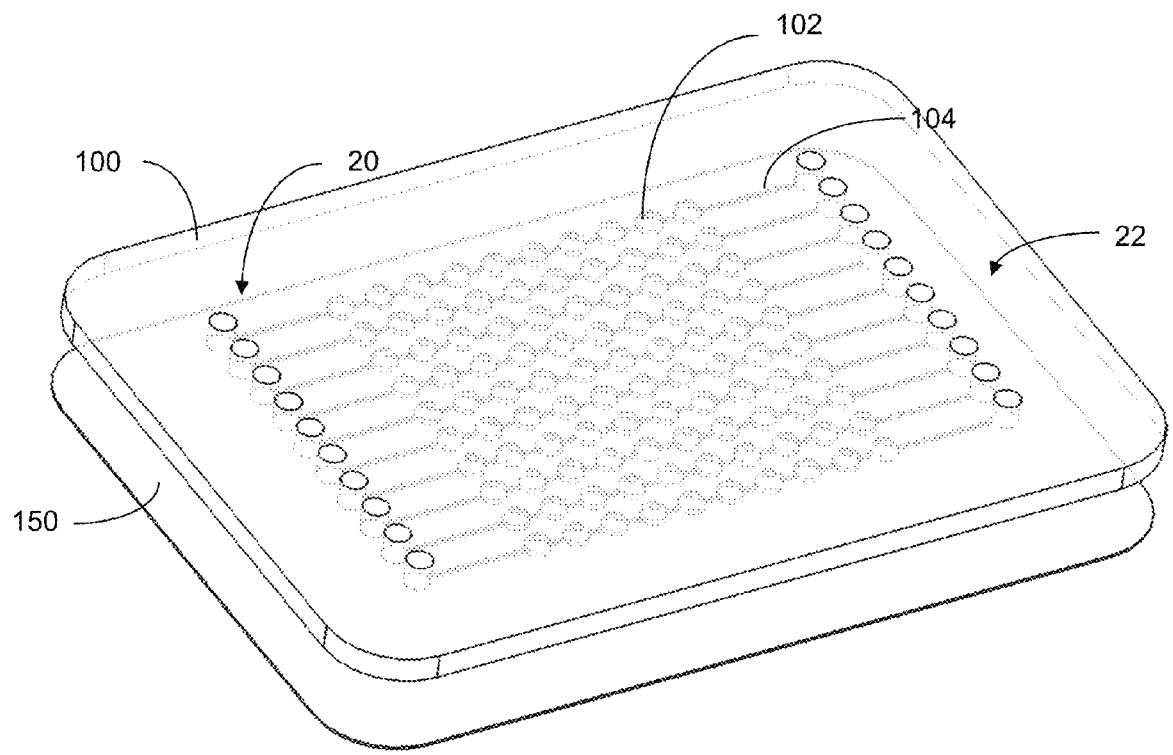
FIG. 17A depicts an exploded perspective view of yet another microfluidic device in accordance with some embodiments.
Figure 17B:
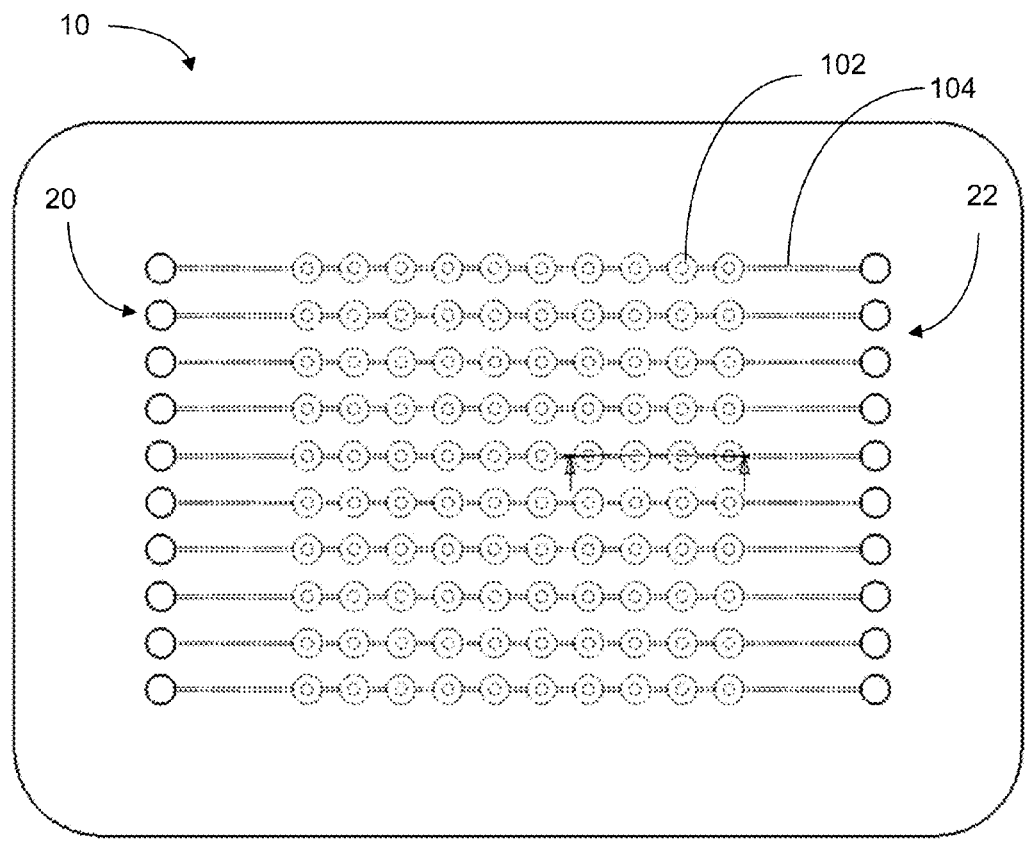
FIG. 17B shows a cross-sectional view of the microfluidic device of FIG. 17A.
Figure 17B:
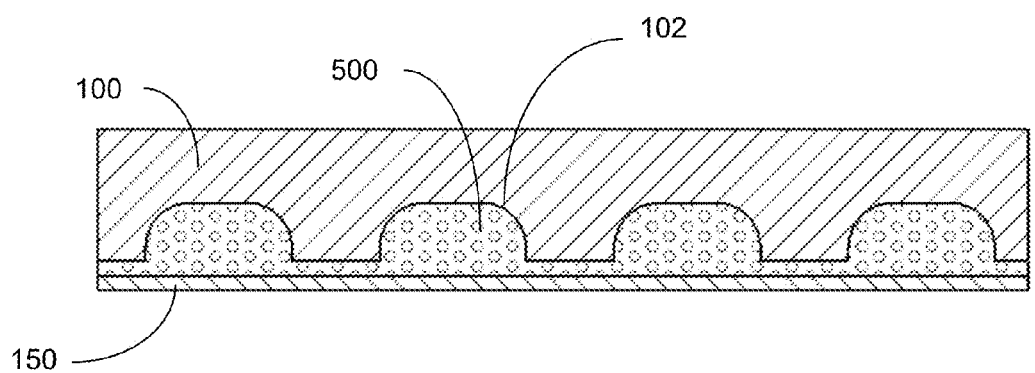
Figure 17C:
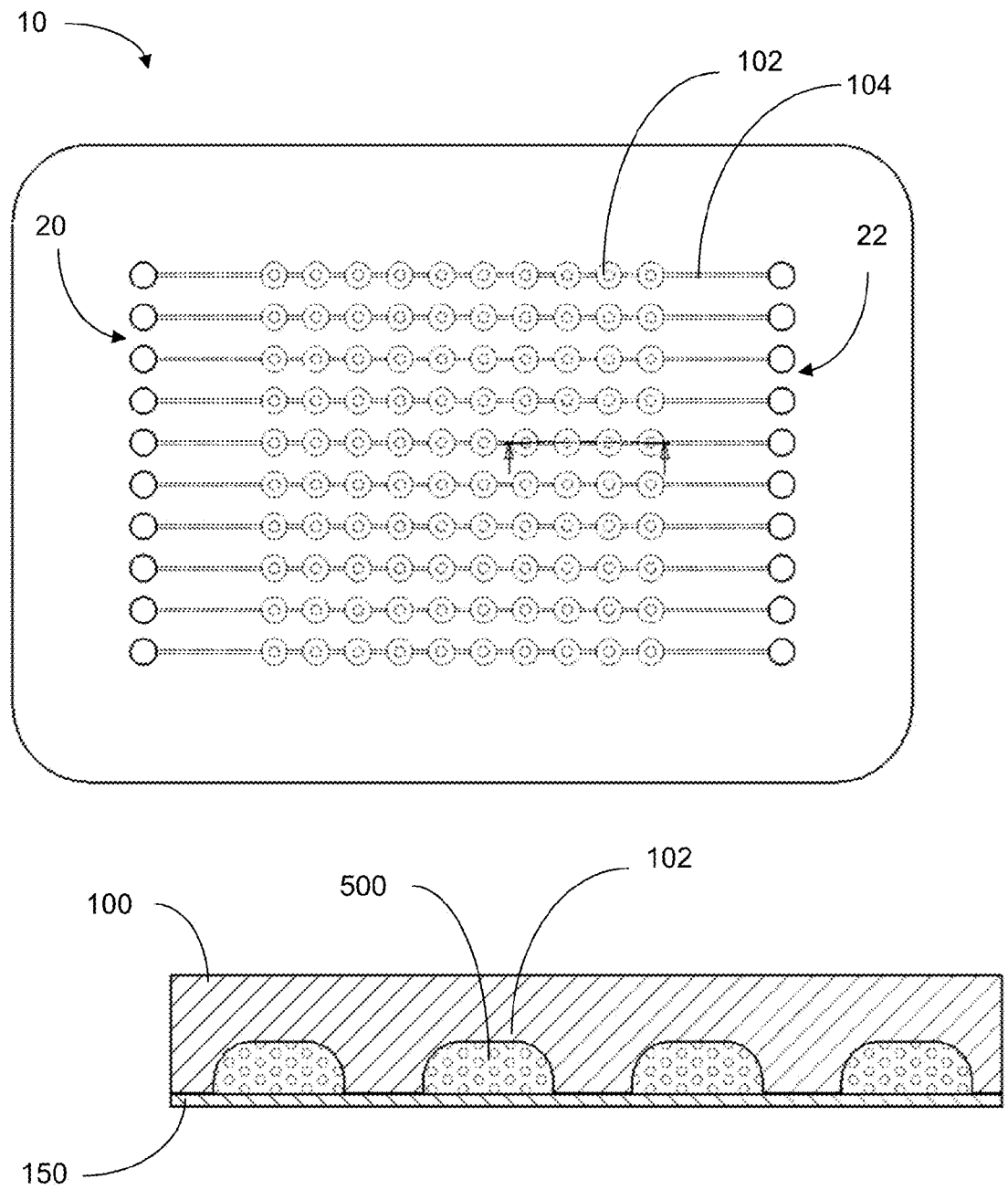
FIG. 17C shows a cross-sectional view of the microfluidic device of FIG. 17A with sealed channels.

Another embodiment of a microfluidic device that may be used for digital PCR is shown in FIGS. 17A-17C. The microfluidic device includes a first layer 100 and a second layer 110. The first layer 100 includes an array of cavities 102, channels 104, inlets 20 and vents 22. The second layer 110 in this embodiment is similar to the intermediate layer 150 shown in FIGS. 16A-16C in that the second layer includes a sealing material that surrounds each of the channels 104 of the first layer 100.

As shown in FIG. 17B, prior to actuation (e.g., compression and/or heating) of the device, the channels 104 permit fluid flow between cavities 102. Though, after actuation, the channels 104 are sealed causing the cavities 102 to be fluidly isolated, as shown in FIG. 17C.

In some embodiments, the sealing material of the second layer 150 may include an adhesive material disposed on a substrate (e.g., plastic backing). Alternatively, this layer may be disposed on the first layer 100, or may be composed of a continuous membrane.

It can be appreciated that for embodiments in accordance with the present disclosure, the sealing material is not required to be a continuous monolithic layer, nor is it necessary for it to be of the same external dimensions as the first layer in which the cavities are defined. It can be appreciated that the layer(s) of the device, including the sealing material, are not required to have dimensions where the layer(s) come(s) into alignment. Nor is it required that the layer defining the cavities be above or below the sealing material.

Thus, in this embodiment, after the cavities are filled with a suitable DNA sample solution, the layer 150 is subject to heating and/or compression. It can be appreciated that the sealing material is not required to be a continuous layer, as the sealing material may include a number of separate components.

As discussed above, microfluidic devices described herein may include, or may otherwise engage with another device/component with, protrusions that enhance the effects of compression at selected locations. Protrusions may be structural projections that extend/jut outwardly from a layer. In some embodiments, protrusions may have at least one dimension that extends along the plane parallel to the layer that is less than the respective dimension of the cavities of the device. For example, the ratio of the width $w_c$ of a cavity to the width $w_p$ of a protrusion may be between 1 and 8, between 1.5 and 5, or between 2 and 4.

In some embodiments, protrusions may be provided in alignment with particular channel regions so that when the overall device is compressed, the protrusions provide a greater amount of stress to the channel regions as compared with other regions that are not aligned with the protrusions. While the inclusion of protrusions in certain regions may provide for a greater degree of compressive stress to those regions (e.g., regions of channels to be sealed off), the absence of protrusions in other regions may result in an effective reduction of compressive stress that would otherwise occur over regions where reactions are intended to occur (e.g., cavities, chambers). Mitigating the compressive stress at regions where reactions are intended to occur may be beneficial to reduce the overall amount of fluid displaced by compression, and further reduces the overall pressure acting on the sealed regions.

Figure 18A:
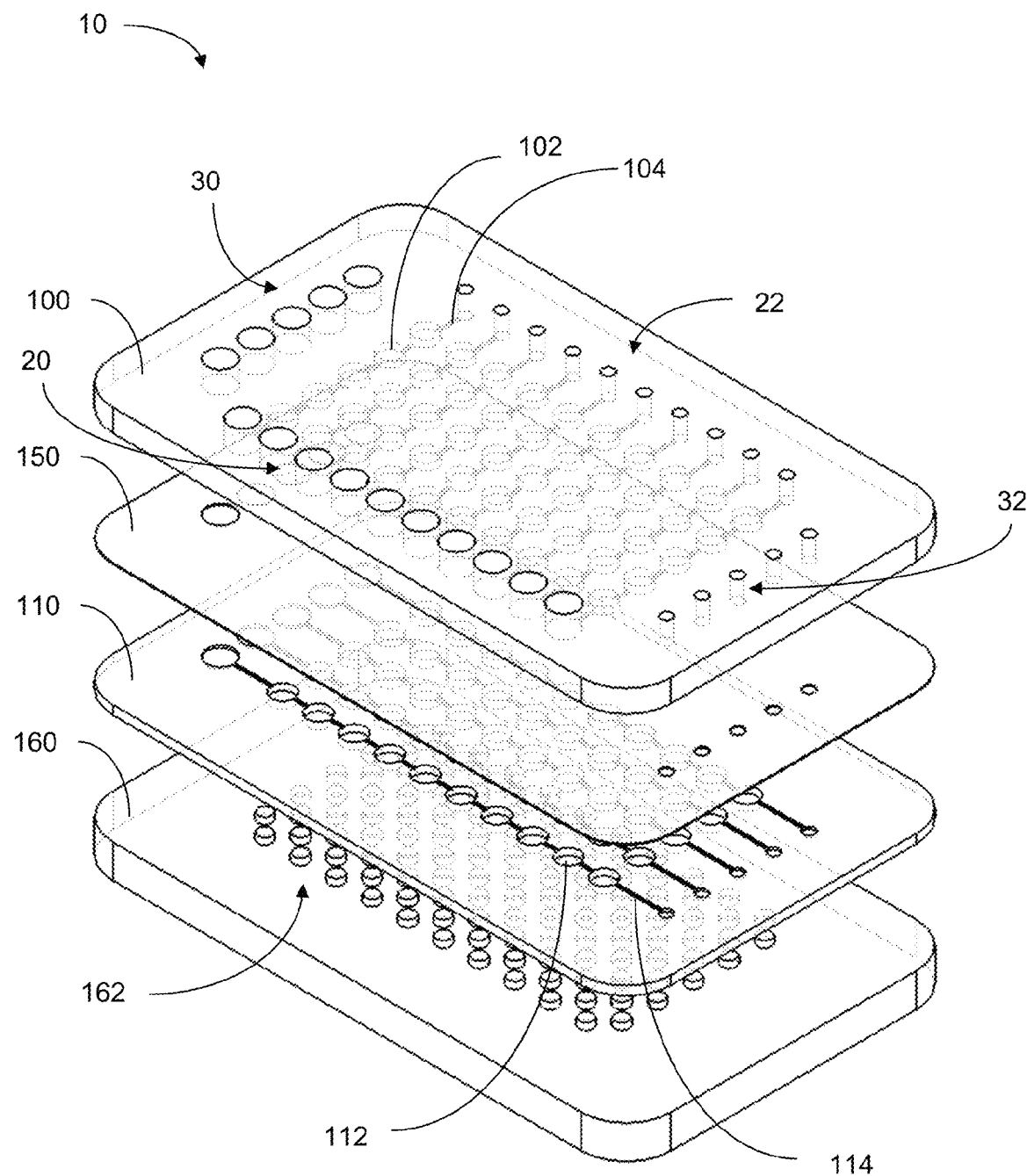
FIG. 18A depicts an exploded perspective view of another microfluidic device in accordance with some embodiments.
Figure 18B:
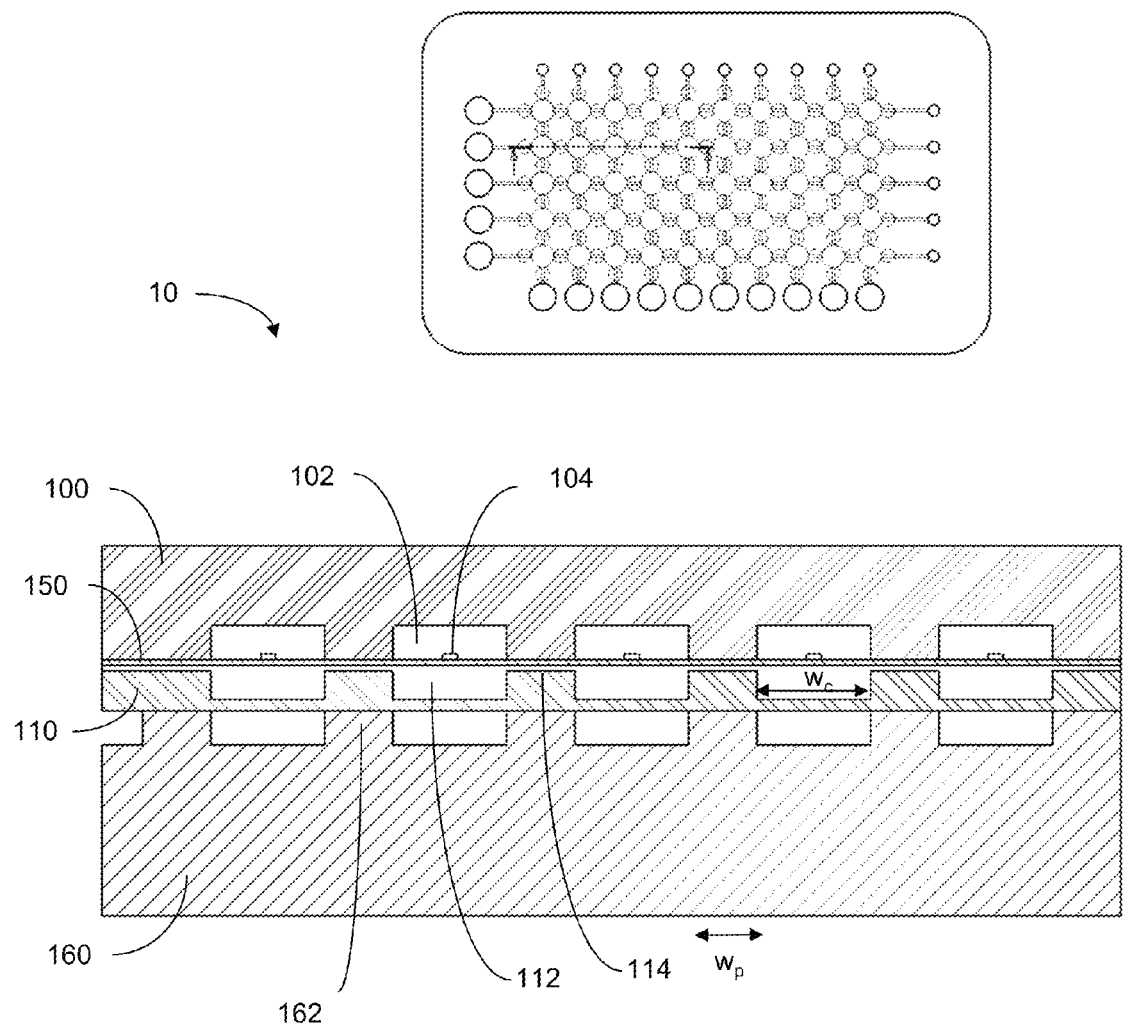
FIG. 18B shows a cross-sectional view of the assembled microfluidic device of FIG. 18A.

FIGS. 18A-18B depict an embodiment of a microfluidic device 10 similar to that shown in FIGS. 1-4, yet includes an additional layer 160 that has protrusions 162 that provide for enhanced compression at certain channel regions of the device. As shown in FIG. 18B, the protrusions 162 are aligned with channels 114 of the second layer 110 and channels 104 of the first layer 100, such that upon compression of the layers of the device 10 together, hence pressing of the protrusions toward the channels 104, 114, the channels are subject to a greater degree of compressive stress than, for example, the cavities 102, 112. Accordingly, the protrusions allow the channels 104, 114 to be more easily sealed, i.e., less externally applied compressive force is necessary for the channels 104, 114 to be sealed off than would otherwise be required if the aligned protrusions were not present. In addition, the width $w_p$ of the protrusions is shown to be less than the width $w_c$ of the cavities.

Such protrusions (e.g., ribs, bumps, ridges, patterned projections, etc.) for enhancing compressive stresses may be patterned in any suitable manner. As discussed above, the protrusions may be part of the microfluidic device itself, a separate thermal cycling apparatus, and/or may be a separate layer/component that is used primarily for compression. Alternatively, appropriate protrusions may be formed on the surface of any of the layers of the device (e.g., on a separating/sealing material, on appropriate regions of a layer defining cavities and/or channels, etc.).

Figure 19A:
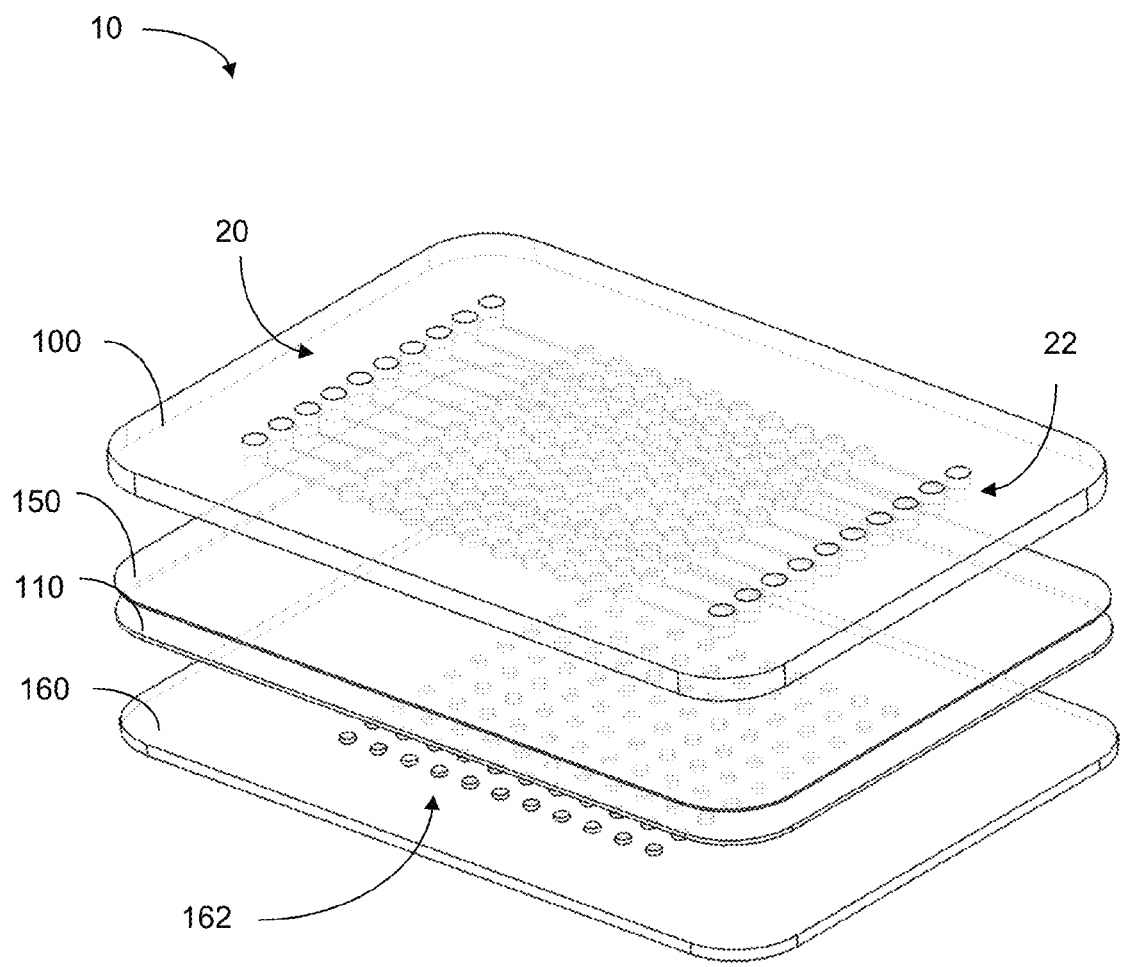
FIG. 19A depicts an exploded perspective view of another microfluidic device in accordance with some embodiments.
Figure 19B:
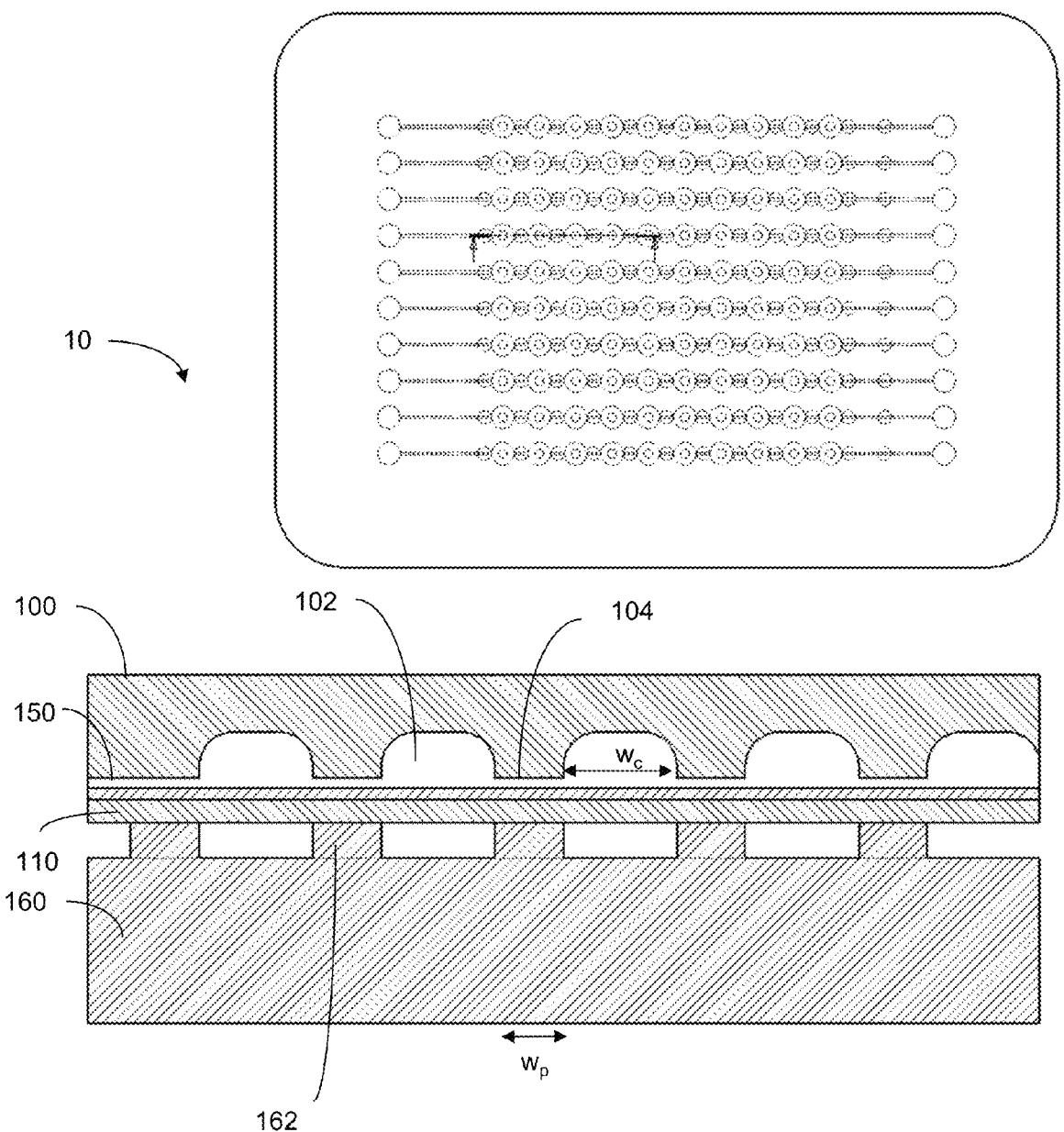
FIG. 19B shows a cross-sectional view of the assembled microfluidic device of FIG. 19A.

FIGS. 19A-19B show an embodiment of a microfluidic device 10 similar to that illustrated in FIGS. 16A-16C, yet includes an additional layer 160 that has protrusions 162 that provide for enhanced compression at channel regions of the device.

Figure 20A:
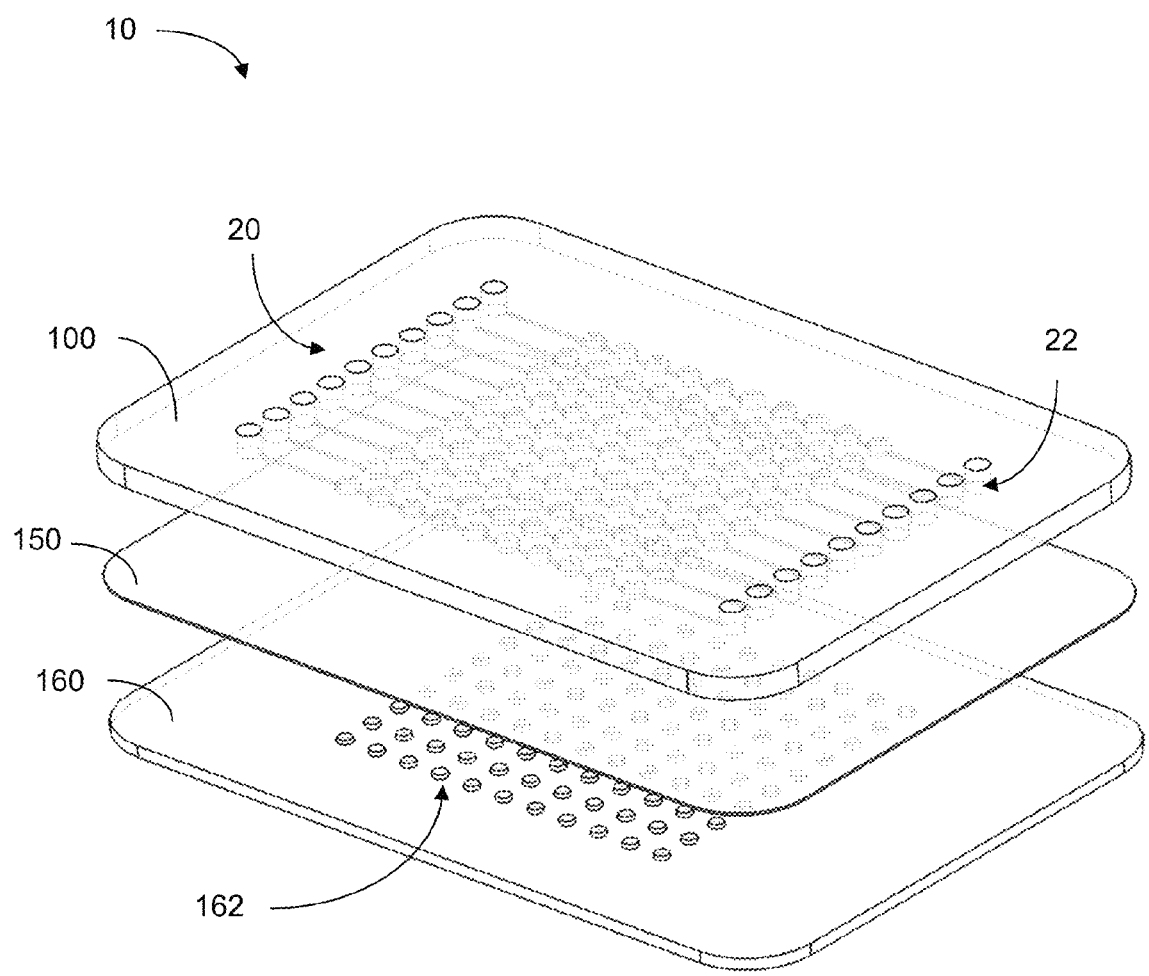
FIG. 20A depicts an exploded perspective view of another microfluidic device in accordance with some embodiments.
Figure 20B:
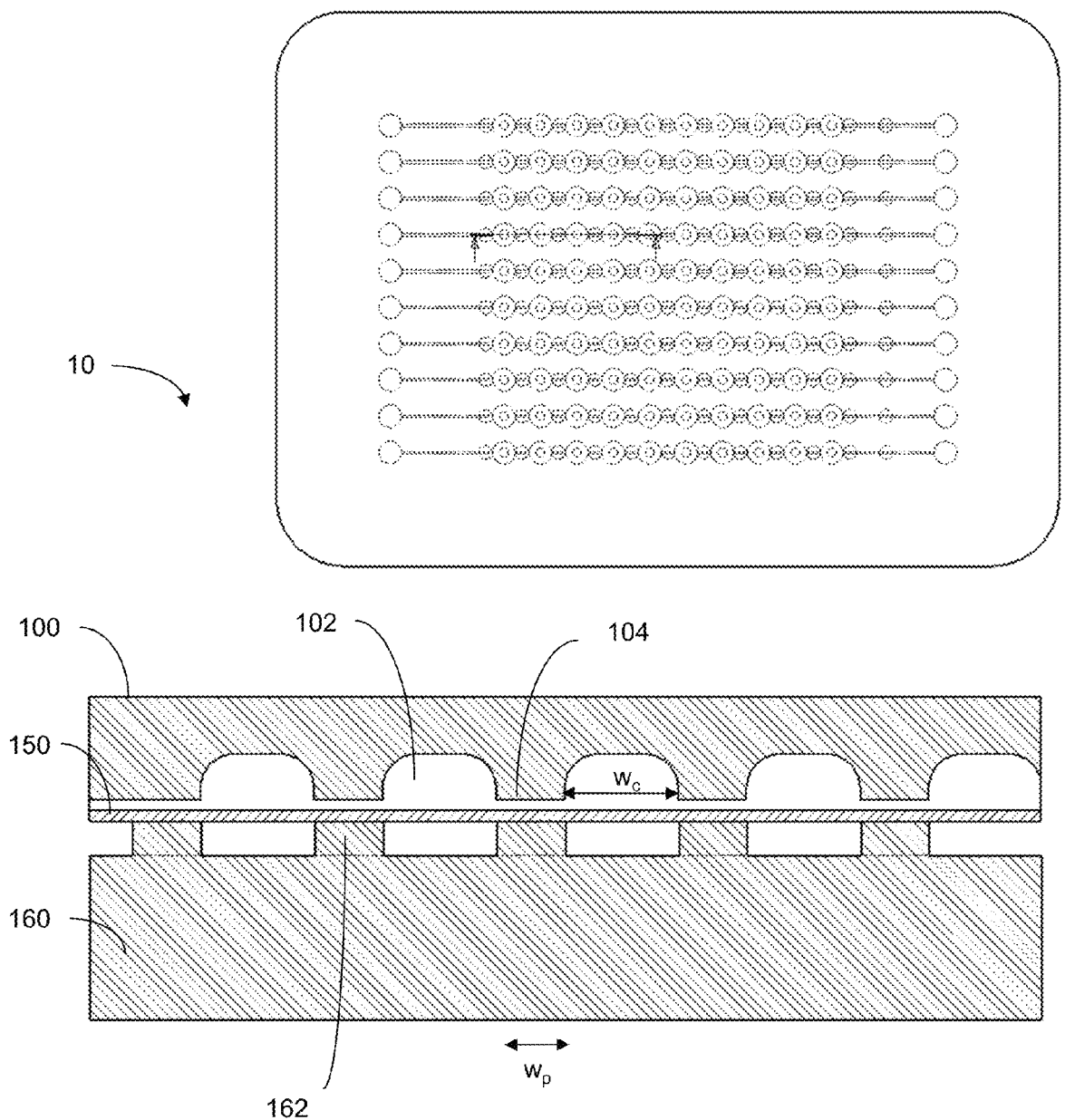
FIG. 20B shows a cross-sectional view of the assembled microfluidic device of FIG. 20A.

FIGS. 20A-20B depict an embodiment of a microfluidic device 10 similar to that illustrated in FIGS. 17A-17C, though, the additional layer 160 having protrusions 162 that provide for enhanced compression is also included. Here, during compression, the protrusions 162 are placed in direct contact with the sealing material of the layer 150.

In some embodiments, a sealing material may be selectively compressed so as to create a number of reaction cavities. For example, channels defined by a layer may be filled with a fluid ingredient and a sealing material may be actuated in a manner that results in partitioning of the channel into reaction cavities that are fluidly isolated from one another.

Figure 21:
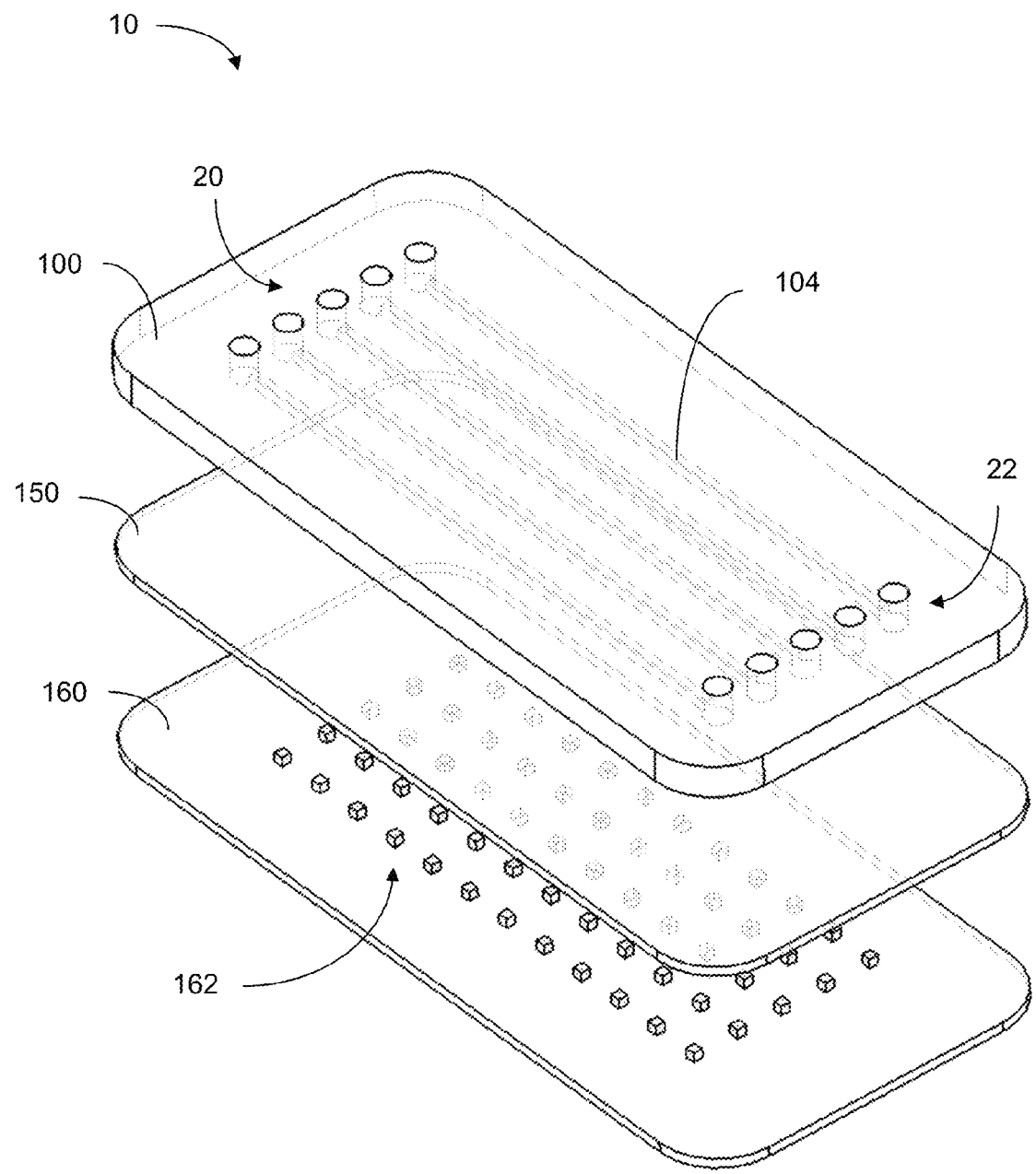
FIG. 21 depicts an exploded perspective view of another microfluidic device in accordance with some embodiments.

In an embodiment shown in FIG. 21, reaction cavities may be formed by deforming the sealing material of layer 150 into the channels 104 defined by first layer 100 at intervals along the channel; actuated by compression, heat or a combination of heat and compression of the device. The additional layer 160, which may, for example, be a part of the device, part of an external compression system, or part of a thermal cycling device on which the microfluidic device is heated, contains an array of protrusions 162 which partition the channels into suitable lengths, creating cavities corresponding to the desired volume(s) of fluid ingredient. In some embodiments, such protrusions 162 may be adapted to jut into the channel with the sealing material. Or, the protrusions may remain outside the space initially defined by the channel while suitably deforming the sealing material into the channel(s). Alternatively, such protrusions may be formed on the sealing layer 150, or the first layer 100.

As discussed further above, the sealing material may include any suitable composition. In some embodiments, the sealing material may be an adhesive, e.g., a hot melt adhesive, acrylic adhesive, or other appropriate adhesive material, positioned on a plastic backing. Alternatively, the sealing material may be a wax, elastomer, or other relatively deformable material.

Such a sealing material may be provided as a standard adhesive tape (e.g., packing tape), allowing for relatively simple device assembly. Accordingly, for some embodiments, a molded first layer may define a number of channels (with optional cavities), input wells, and vent holes. A piece of tape may be attached to the molded layer, covering the channels (and optional cavities) and the device would essentially be ready for use.

Figure 22A:
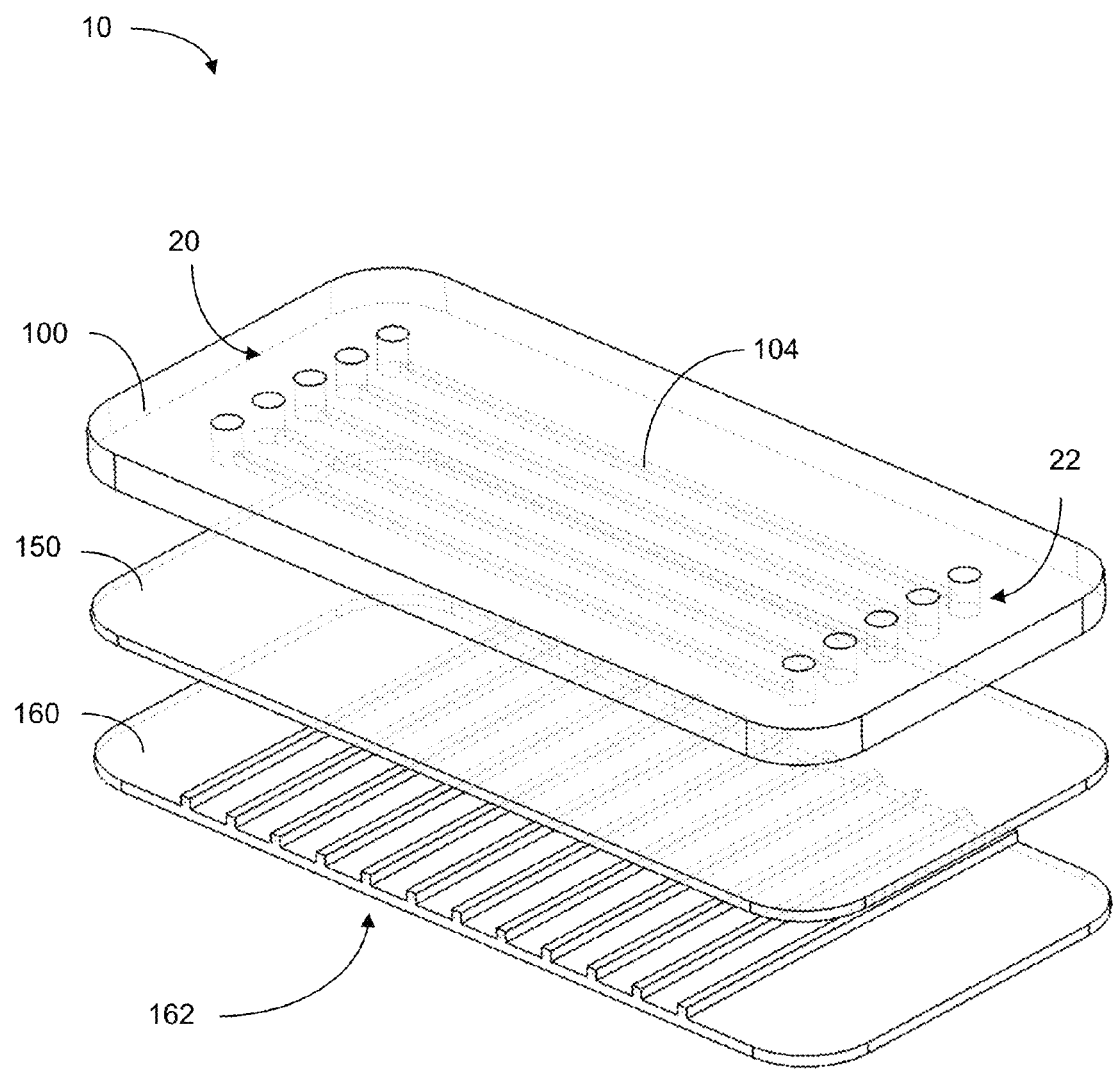
FIG. 22A depicts an exploded perspective view of another microfluidic device in accordance with some embodiments.
Figure 22B:
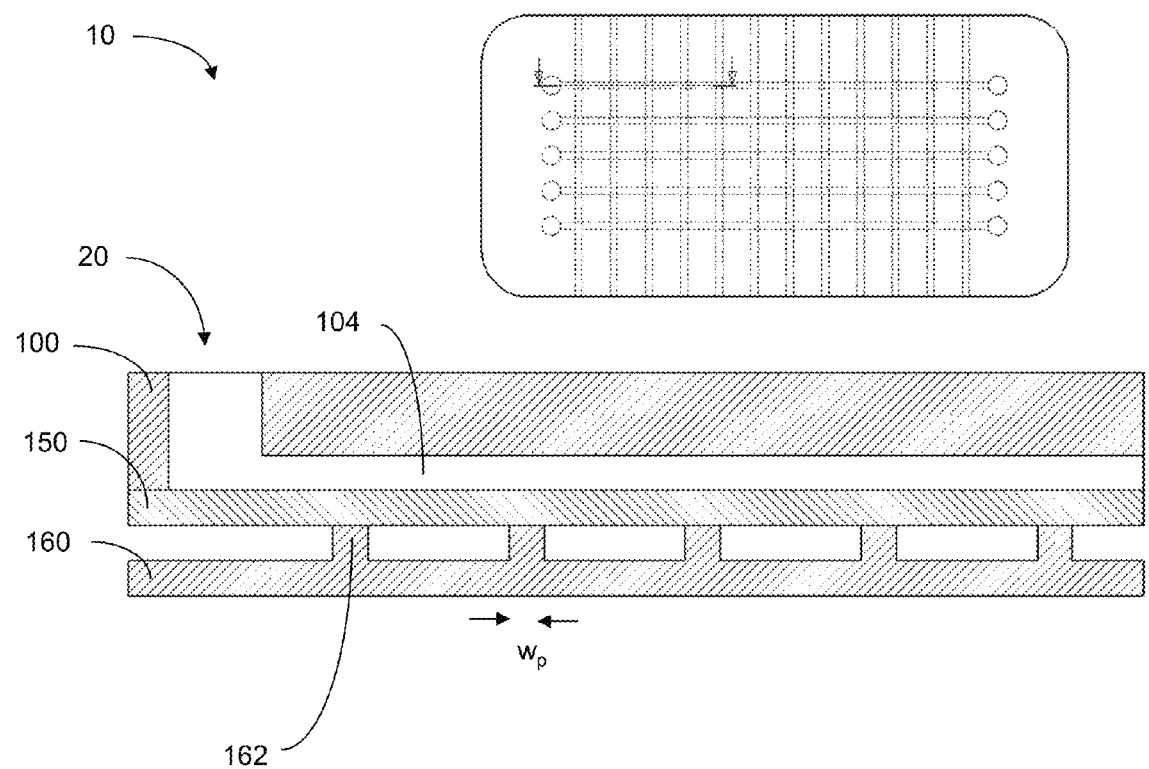
FIG. 22B shows a cross-sectional view of the assembled microfluidic device of FIG. 22A.
Figure 22C:
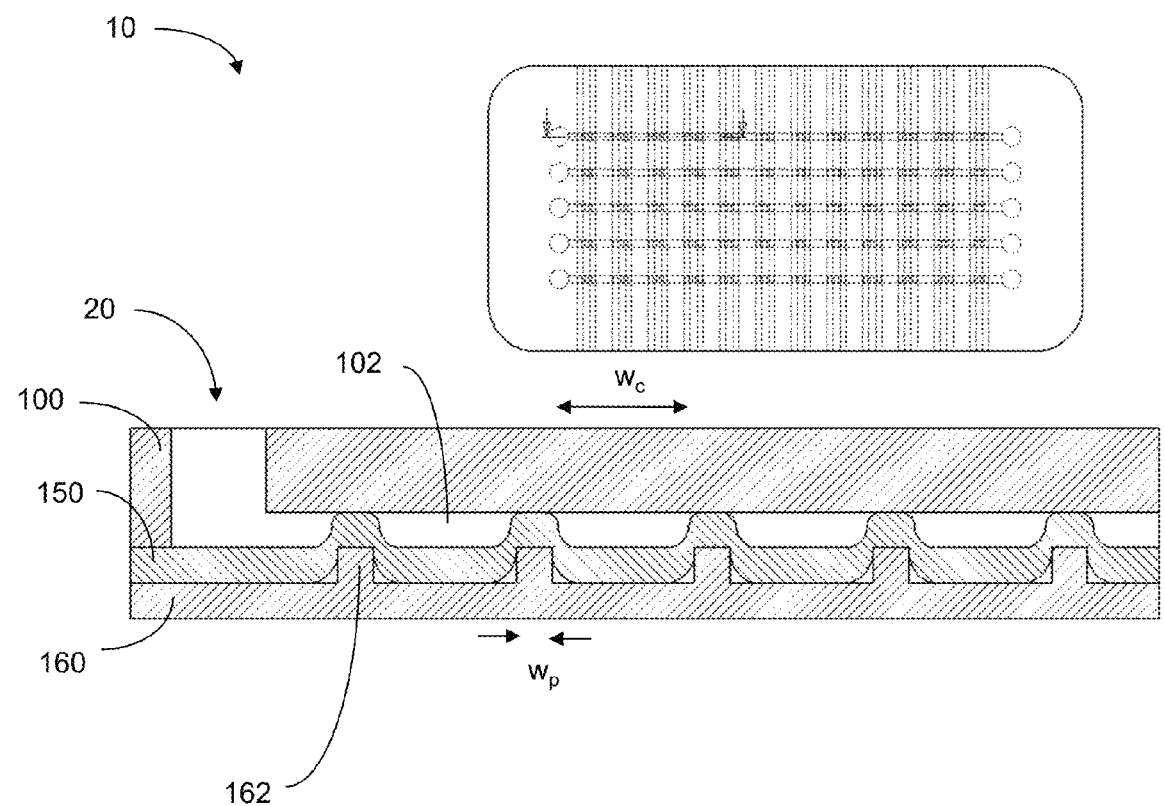
FIG. 22C shows a cross-sectional view of the assembled microfluidic device of FIG. 22B in a different state.

The embodiment of the microfluidic device 10 shown in FIGS. 22A-22C is similar to that of FIG. 21 except that the additional layer 160 includes protrusions 162 which are formed as elongated ridges. The elongated ridges are provided to control selective compression of the sealing material and are arranged to extend substantially perpendicular to the channels 104. Accordingly, when the device is subject to compression, the ridges act to concentrate the compressive force in a manner that causes deformation of the sealing material into the channels so as to define an array of reaction cavities in fluid isolation from one another, as well as any fluid source reservoir(s).

FIG. 22B shows the device prior to compression where fluid is permitted to flow throughout the channel 104 and cavities are not yet formed. That is, in such an embodiment, pre-formed cavities, prior to compression of the sealing material, are absent. Upon compression, the protrusions 162 are pressed into the sealing material of layer 150 resulting in partitioning of the channel into cavities 102, shown in FIG. 22C. The resulting cavities 102 are in fluid isolation, providing for individual reactions (e.g., PCR) to occur in each. As shown, while not required, the width $w_p$ of the protrusions is less than the width $w_c$ of the resulting cavities.

The resulting cavities in which reactions are able to occur separate from other cavities may define any suitable length corresponding to any desired volume of fluid ingredient. As a result, the use of protrusions to form separate cavities in which reactions may occur is advantageous in allowing for simple manufacturing and assembly of a microfluidic device 10 that does not require substantial effort in aligning various components/layers of the device.

Accordingly, a suitable sealing material may be deformed into the space of the channels through which fluid would otherwise be able to flow and may further result in appropriate partitioning of the channel into cavities within which separate reactions are able to occur. This deformation may be plastic, hence, permanent in nature. Thus, absent disassembly of the microfluidic device to remove the sealing material from the channels, such channel sealing is irreversible.

Figure 23:
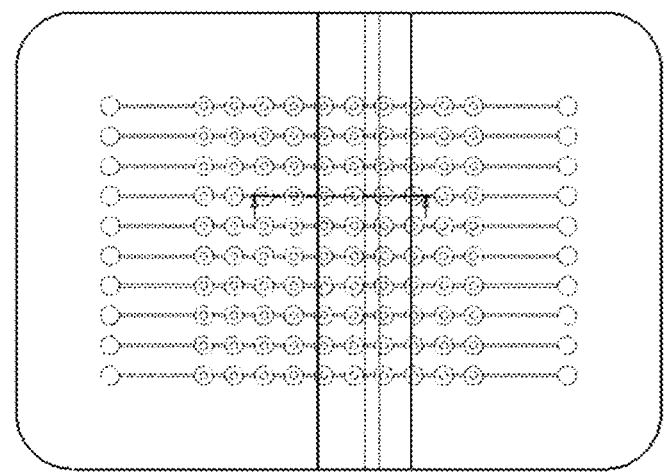
FIG. 23 shows a cross-sectional view of another microfluidic device in accordance with some embodiments.
Figure 23:
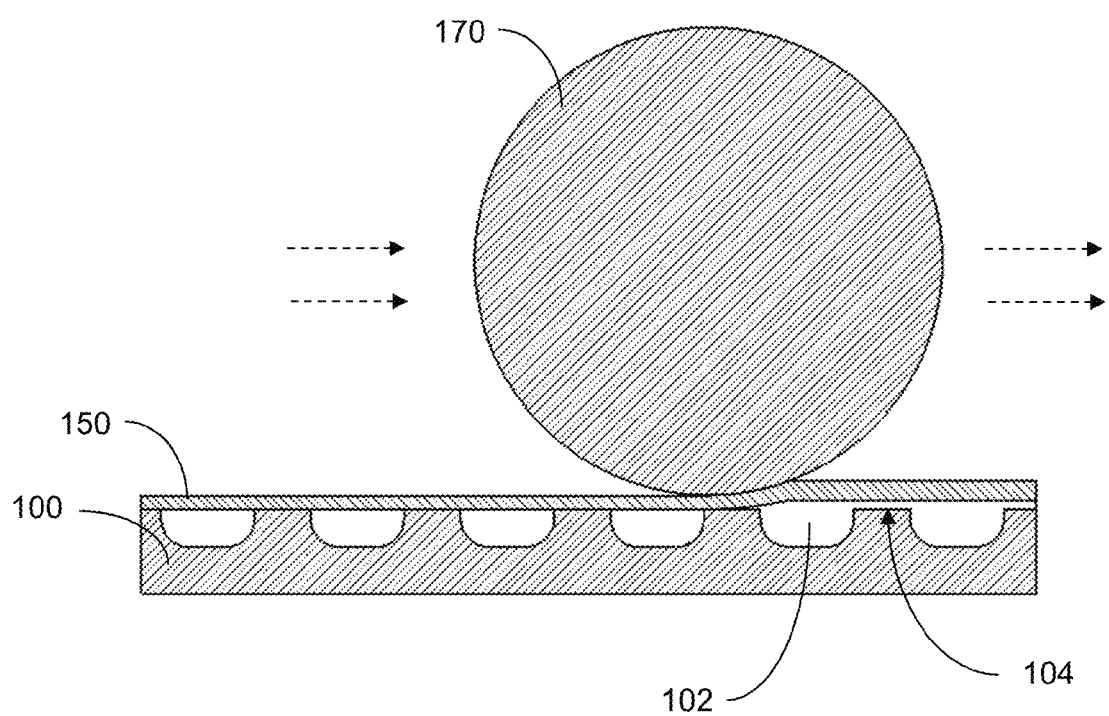

It can be appreciated that various aspects of sealing described herein are applicable for different applications, such as digital and non-digital PCR, and/or partitioning of channels into separate cavities. As shown in FIG. 23, the microfluidic device may also be compressed through the use of a roller. For example, a roller 170 may be provided so as to travel along the length of the channel(s) 104 (e.g., shown by the direction indicated by the dashed arrows) resulting in serial deformation of the sealing material and sealing of the channels 104 and cavities 102 connected by the channels. This method may be advantageous in that the roller would effectively function to progressively displace fluid from each cavity or channel being compressed into the next uncompressed cavity or out through the vent.

As illustrated in FIG. 23, as the roller 170 moves along and compresses the channel 104, excess material (e.g., fluid ingredient, air) that flows from the channel 104 and cavities 102 is displaced to neighboring cavities and channels until the excess material is vented or contained in an appropriate additional cavity and/or relief chamber. This sequential displacement would reduce the overall pressure that would otherwise arise in the cavities and channels due to the compression of the fluid ingredient, and would therefore result in stronger sealing of the channels.

Devices of the present disclosure may be useful for digital PCR and/or non-digital PCR. While devices illustrated by the figures are depicted to have relatively few cavities/aliquots, it can be appreciated that any appropriate number of cavities/aliquots may be implemented. For example, devices used for digital PCR may form 100-10,000 aliquots per sample input. In general, the greater the number of partitions for a digital PCR application, the larger the dynamic range and, hence, the better statistical precision of quantification of the sample.

The microfluidic device may provide any suitable volume for each cavity/aliquot. In some embodiments, a suitable range of volume per partition (e.g., forming reaction cavities) may be between 10 picoliters and 300 nanoliters, between 500 picoliters and 200 nanoliters, or between 1 nanoliter and 100 nanoliters. With the ability to produce a large number of aliquots, the volume of each individual aliquot can be lowered so as to reduce the amount of reagents needed and, hence, the overall cost.

Having thus described several aspects of at least one embodiment of this invention, it is to be appreciated various alterations, modifications, and improvements will readily occur to those skilled in the art. Such alterations, modification, and improvements are intended to be part of this disclosure, and are intended to be within the spirit and scope of the invention. Accordingly, the foregoing description and drawings are by way of example only.

What is claimed is:

1. A microfluidic device, comprising:
a first layer defining a first cavity;
a first channel arranged to provide fluid entry to the first cavity;
a second layer defining a second cavity;
a second channel arranged to provide fluid entry to the second cavity; and
at least one separating material located between the first layer and the second layer and providing fluid separation between the first cavity and the second cavity, the at least one separating material comprising at least one of plastic, polymer, polyethylene, ethylene-vinyl acetate, polycarbonate, PTFE, polypropylene, elastomer, silicone, silicone rubber, wax, paraffin wax and microcrystalline wax, wherein compression of the first and second layers relative to one another causes sealing of the first channel and the second channel resulting in obstruction of the first cavity and the second cavity from further fluid entry, and wherein manipulation of the at least one separating material causes removal of the fluid separation allowing for fluid communication between the first cavity and second cavity.

2. The microfluidic device of claim 1, wherein the first layer defines a plurality of first cavities and the second layer defines a plurality of second cavities, the plurality of first and second cavities corresponding to an array of chambers, and wherein each chamber is adapted to house a reaction upon removal of the fluid separation according to a combination of fluid ingredients provided by a plurality of fluid source reservoirs.

3. The microfluidic device of claim 1, wherein compression of the first and second layers relative to one another causes fluid isolation of the first and second cavities from adjacent first and second cavities.

4. The microfluidic device of claim 1, wherein compression of the first and second layers relative to one another causes substantial filling of the first and second channels with a sealing material.

5. The microfluidic device of claim 4, wherein the at least one separating material comprises the sealing material.

6. The microfluidic device of claim 5, wherein the at least one separating material and the sealing material comprise a single deformable film.

7. The microfluidic device of claim 4, wherein the at least one separating material is independent of the sealing material.

8. The microfluidic device of claim 7, wherein the first layer or the second layer comprises the sealing material.

9. The microfluidic device of claim 4, wherein compression of the first and second layers relative to one another causes plastic deformation of the sealing material.

10. The microfluidic device of claim 4, wherein heating of the sealing material promotes substantial filling of the first and second channels with the sealing material.

11. The microfluidic device of claim 1, wherein manipulation of the separating material causes irreversible removal of the fluid separation between the first cavity and second cavity.

12. The microfluidic device of claim 1, wherein tearing of the at least one separating material causes removal of the fluid separation between the first cavity and second cavity.

13. The microfluidic device of claim 12, wherein the at least one separating material is in a stressed or stretched state that, upon manipulation, promotes tearing of the at least one separating material.

14. The microfluidic device of claim 12, wherein the at least one separating material is in a scored or at least partially cut state that, upon manipulation, promotes tearing of the at least one separating material.

15. The microfluidic device of claim 1, wherein the at least one separating material is adapted to contract under application of heat.

16. The microfluidic device of claim 1, wherein manipulation of the at least one separating material comprises application of heat.

17. The microfluidic device of claim 1, wherein manipulation of the at least one separating material comprises application of at least one of a compressive force, a magnetically driven force, laser irradiation and centrifugation.

18. The microfluidic device of claim 1, further comprising at least one relief cavity fluidly connected to a corresponding cavity and adapted to receive an overflow of fluid from the corresponding cavity.

19. The microfluidic device of claim 18, wherein the at least one relief cavity is adapted to remain substantially filled with a volume of air upon supply of the corresponding cavity with fluid.

20. The microfluidic device of claim 4, further comprising at least one storage cavity adapted to prevent excess sealing material from filling the first cavity or the second cavity.

21. The microfluidic device of claim 1, in combination with a system arranged to perform polymerase chain reaction.

22. The microfluidic device of claim 1, wherein the first and second channels are substantially aligned with a plurality of protrusions extending from at least one of the first layer, the second layer and an additional layer.

23. A microfluidic device, comprising:
a first layer defining a first cavity;
a first channel arranged to provide fluid entry to the first cavity;
a second layer defining a second cavity;
a second channel arranged to provide fluid entry to the second cavity; and
at least one separating material providing fluid separation between the first cavity and the second cavity, wherein compression of the first and second layers relative to one another causes sealing of the first channel and the second channel resulting in obstruction of the first cavity and the second cavity from further fluid entry, and wherein manipulation of the at least one separating material causes removal of the fluid separation allowing for fluid communication between the first cavity and second cavity, wherein the at least one separating material comprises at least one of polycarbonate, PTFE, silicone, polypropylene and paraffin wax.

* * * * *